US011440874B2

(12) United States Patent
Xiang et al.

(10) Patent No.: US 11,440,874 B2
(45) Date of Patent: Sep. 13, 2022

(54) KETAMINE DERIVATIVES AND COMPOSITIONS THEREOF

(71) Applicant: XWPHARMA LTD., Grand Cayman (KY)

(72) Inventors: Jia-Ning Xiang, Wuhan (CN); Xuesong Xu, Wuhan (CN); Hao-Wei Shih, New Taipei (TW); Wai-Si Eng, Maple Glen, PA (US)

(73) Assignee: XWPHARMA LTD., Grand Cayman (KY)

( * ) Notice: Subject to any disclaimer, the term of this patent is extended or adjusted under 35 U.S.C. 154(b) by 0 days.

(21) Appl. No.: 17/067,968

(22) Filed: Oct. 12, 2020

(65) Prior Publication Data

US 2021/0032199 A1 Feb. 4, 2021

Related U.S. Application Data

(60) Continuation of application No. 16/838,633, filed on Apr. 2, 2020, now Pat. No. 10,836,714, which is a division of application No. 16/502,562, filed on Jul. 3, 2019, now Pat. No. 10,683,262, which is a continuation of application No. PCT/CN2019/070912, filed on Jan. 8, 2019.

(60) Provisional application No. 62/615,948, filed on Jan. 10, 2018.

(51) Int. Cl.
| | |
|---|---|
| C07C 271/24 | (2006.01) |
| C07D 305/06 | (2006.01) |
| A61K 9/00 | (2006.01) |
| C07C 211/35 | (2006.01) |
| C07D 213/80 | (2006.01) |
| C07D 309/08 | (2006.01) |
| C07D 317/68 | (2006.01) |
| A61K 31/165 | (2006.01) |
| A61K 31/166 | (2006.01) |
| C07D 207/16 | (2006.01) |
| C07D 207/28 | (2006.01) |
| C07D 211/62 | (2006.01) |
| C07C 271/56 | (2006.01) |

(52) U.S. Cl.
CPC .......... *C07C 271/24* (2013.01); *A61K 9/0053* (2013.01); *A61K 31/165* (2013.01); *A61K 31/166* (2013.01); *C07C 211/35* (2013.01); *C07D 213/80* (2013.01); *C07D 305/06* (2013.01); *C07D 309/08* (2013.01); *C07D 317/68* (2013.01); *C07C 271/56* (2013.01); *C07D 207/16* (2013.01); *C07D 207/28* (2013.01); *C07D 211/62* (2013.01)

(58) Field of Classification Search
CPC ... C07C 271/24; C07C 211/35; C07C 211/62; C07D 207/16; C07D 207/28; C07D 271/56; C07D 305/06; A61K 31/165; A61K 31/166
See application file for complete search history.

(56) References Cited

U.S. PATENT DOCUMENTS

| | | | | |
|---|---|---|---|---|
| 5,648,087 A | * | 7/1997 | Ovaert | A61P 39/02 |
| | | | | 424/423 |
| 5,837,730 A | * | 11/1998 | Javitt | A61P 43/00 |
| | | | | 514/551 |
| 6,248,789 B1 | | 6/2001 | Weg | |
| 11,110,070 B2 | * | 9/2021 | Brachman | A61P 25/24 |
| 2004/0248964 A1 | | 12/2004 | Crooks et al. | |
| 2014/0079740 A1 | | 3/2014 | Salama | |
| 2015/0259277 A1 | | 9/2015 | Sleigh et al. | |
| 2018/0098993 A1 | | 4/2018 | Wainer et al. | |
| 2018/0177744 A1 | * | 6/2018 | Jay | A61K 47/36 |
| 2018/0289637 A1 | | 10/2018 | Laufer et al. | |
| 2019/0240184 A1 | | 8/2019 | Hashimoto | |
| 2020/0306194 A1 | * | 10/2020 | Glue | A61K 9/2813 |

FOREIGN PATENT DOCUMENTS

| | | |
|---|---|---|
| CN | 104395283 | 3/2015 |
| CN | 111836798 | 10/2020 |
| EA | 201590697 | 9/2015 |
| JP | 2006-510618 | 3/2006 |
| JP | 2009-509982 | 3/2009 |
| JP | 2015-501302 | 1/2015 |
| JP | 2015-535847 | 12/2015 |
| WO | 97/07750 | 3/1997 |
| WO | 2004/045601 | 6/2004 |
| WO | 2008/134525 | 11/2008 |
| WO | 2011/109799 | 9/2011 |
| WO | 2013/019561 | 2/2013 |
| WO | 2013/056229 | 4/2013 |
| WO | 2013/170068 | 11/2013 |
| WO | 2014/057414 | 4/2014 |
| WO | 2014/205389 | 12/2014 |

(Continued)

OTHER PUBLICATIONS

Mayo Clinic, Depression (major depressive disorder), Mayo Foundation for Medical Education and Research, 5 pages, 1998-2021 (Year: 1998).*
Fawcett, J., et al., Anxiety syndromes and their relationship to depressive illness, Journal of clinical Psychiatry, 44 (8, sec. 2), pp. 8-11 (Year: 1983).*
Lahti, A. C., et al., Ketamine activates psychosis and alters limbic blood flow in schizophrenia, Clinical Neuroscience and Neuropathology, Neuro Report, vol. 6, No. 6, pp. 869-872 (Year: 1995).*

(Continued)

*Primary Examiner* — Yate' K Cutliff

(57) ABSTRACT

Ketamine derivatives and pharmaceutical compositions thereof are disclosed. When administered orally the ketamine derivatives provide increased bioavailability of ketamine in the systemic circulation. The ketamine derivatives can be used to treat neurological diseases, psychological diseases and pain.

18 Claims, No Drawings

(56) References Cited

FOREIGN PATENT DOCUMENTS

| WO | 2014/205393 | 12/2014 |
|---|---|---|
| WO | 2017/087388 | 5/2017 |
| WO | 2017/117529 | 7/2017 |
| WO | 2017/208031 | 12/2017 |
| WO | 2018/079693 | 5/2018 |

OTHER PUBLICATIONS

Liriano, Flex, et al., Ketamine as treatment for post-traumatic stress disorder: a review, Drugs in Context, 3:212305, pp. 1-7 (Year: 2019).*
Morgan C.J.A., et al., Is persistent ketamine use a valid model of the cognitive and oculomotor deficits in Schizophrenia?, Biol Psychiatry, 65, pp. 1099-1102 (Year: 2009).*
Zhao, X., et al., Simultaneous population pharmacokinetic modelling of ketamine and three major metabolites in patients with treatment-resistant bipolar depression, British Journal of Clinical Pharmacology, 74:2, pp. 304-314 (Year: 2012).*
Sanacora, G. et al., A consensus statement on the use of ketamine in the treatment of mood disorders, JAMA Psychiatry, Clinical Review & Education Special Communication, March, 24 pages (Year: 2017).*
Jose, J. et al., "Structure-activity relationships for ketamine esters as short-acting anaesthetics", Bioorganic & Medicinal Chemistry, Sep. 2013, vol. 21, Issue 17, p. 5098-5106.
Search Report for Australia Application No. 2019206950, dated Oct. 26, 2020, 7 pages.
Search Report for Russia Application No. 2020126393 dated Dec. 1, 2020, 2 pages.
International Search Report and Written Opinion for Application No. PCT/CN2018/090151, dated Feb. 20, 2019, 14 pages.
International Search Report and Written Opinion for Application No. PCT/CN2019/070912, dated Mar. 27, 2019, 11 pages.
International Search Report and Written Opinion for Application No. PCT/CN2019/090189, dated Sep. 18, 2019, 15 pages.
International Search Report and Written Opinion for Application No. PCT/CN2019/095144, dated Sep. 26, 2019, 11 pages.
Non-Final Office Action for U.S. Appl. No. 16/502,562, dated Nov. 5, 2019, 42 pages.
Registry RN 1430202-54-2, Oct. 21, 2013.
Ebert et al., "Norketamine, the main metabolite of ketamine, in a non-competitive NMDA receptor antagonist in the rat cortex and spinal cord", European Journal of Pharmacology, 1997, vol. 333, p. 99-104.
Search Report and Written Opinion for Singapore Application No. 11202006575T, dated Oct. 4, 2021, 12 pages.
Dakwar et al., "A Single Ketamine Infusion Combined with Motivational Enhancement Therapy for Alcohol Use Disorder: A Randomized Midazolam-Controlled Pilot Trial", American Journal Psychiatry, Feb. 2020, vol. 177, No. 2, p. 125-133.
Feder et al., "Efficacy of Intravenous Ketamine for Treatment of Chronic Posttraumatic Stress Disorder: A Randomized Clinical Trial", JAMA Psychiatry, vol. 71, No. 6, 2014, p. 681-688.
Feder et al., "A Randomized Controlled Trial of Repeated Ketamine Administration for Chronic Posttraumatic Stress Disorder", American Journal of Psychiatry, Feb. 2021, vol. 178, No. 2, pp. 193-202.
Mollaahmetoglu et al., "This Is Something That Changed My Life: A Qualitative Study of Patients' Experiences in a Clinical Trial of Ketamine Treatment for Alcohol Use Disorders", Frontiers in Psychiatry, Aug. 2021, vol. 12, Article 695335, 17 pages.
Nielsen et al., "Intraoperative S-ketamine for the reduction of opioid consumption and pain one year after spine surgery: A randomized clinical trial of opioid-dependent patients", Eur J Pain, Jul. 2018, 2019, vol. 23, pp. 455-460.
Rodriguez et al., "Randomized Controlled Crossover Trial of Ketamine in Obsessive-Compulsive Disorder: Proof-of-Concept", Neuropsychopharmacology, 2013, vol. 38, p. 2475-2483.
Taylor et al., "Ketamine for Social Anxiety Disorder: A Randomized, Placebo-Controlled Crossover Trial", Neuropsychopharmacology, 2018, vol. 43, p. 325-333.
Dimitrov et al., "Ketamine esters and amides as short-acting anaesthetics: Structure-activity relationships for the side-chain", Bioorganic & Medicinal Chemistry, 2019, vol. 27, pp. 1226-1231.

* cited by examiner

KETAMINE DERIVATIVES AND COMPOSITIONS THEREOF

This application is a continuation of U.S. application Ser. No. 16/838,633, filed on Apr. 2, 2020, now allowed, which is a division of U.S. application Ser. No. 16/502,562, filed on Jul. 3, 2019, which issued as U.S. Pat. No. 10,683,262, which claims the benefit under 35 U.S.C. § 120 of PCT International Application No. PCT/CN2019/070912 filed on Jan. 8, 2019, which claims priority under 35 U.S.C. § 119(e) to U.S. Provisional Application No. 62/615,948, filed on Jan. 10, 2018, each of which is incorporated by reference in its entirety.

FIELD

The present disclosure relates to ketamine derivatives and pharmaceutical compositions thereof. When administered orally the ketamine derivatives provide increased bioavailability of ketamine in the systemic circulation. The ketamine derivatives can be used to treat neurological diseases, psychological diseases and pain.

BACKGROUND

Ketamine is a cyclohexanone derivative with analgesic and anesthetic properties. Although its mechanism of action has been considered to be mainly a noncompetitive antagonism of the N-methyl-D-aspartic acid (NMDA) receptor ketamine also targets other receptors, such as α-amino-3-hydroxy-5-methyl-4-isoxazolepropionic acid (AMPA) receptors, and has additional acts as an agonist of the sigma 1 receptor. Ketamine is currently used for acute pain management, chronic pain management, for the treatment of major depression, bipolar disorder and suicidal behavior, and as an anti-inflammatory agent. The oral bioavailability of ketamine is low.

SUMMARY

According to the present invention, compounds have the structure of Formula (1):

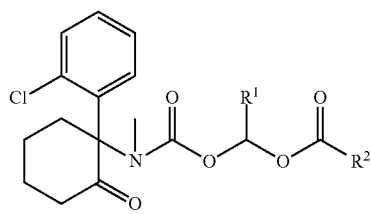

(1)

or a pharmaceutically acceptable salt thereof, wherein,
R$^1$ is selected from hydrogen and C$_{1-6}$ alkyl; and
R$^2$ is selected from a moiety of Formula (2), a moiety of Formula (3), a moiety of Formula (4), and a moiety of Formula (5):

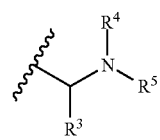

(2)

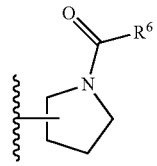

(3)

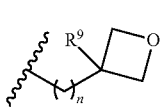

(4)

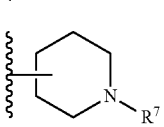

(5)

wherein,
R$^3$ is selected from hydrogen, C$_{1-6}$ alkyl, C$_{7-12}$ alkylarene, and substituted C$_{7-12}$ alkylarene;
R$^4$ is selected from hydrogen and C$_{1-6}$ alkyl;
R$^5$ is selected from hydrogen, C$_{1-6}$ alkyl, —C(=O)—R$^{10}$, and —C(=O)—O—R$^{10}$, wherein R$^{10}$ is selected from C$_{1-6}$ alkyl, C$_{3-6}$ cycloalkyl, and —CF$_3$;
R$^6$ is selected from C$_{1-6}$ alkyl and C$_{1-6}$ alkoxy;
n is an integer from 0 to 3;
R$^7$ is selected from hydrogen, C$_{1-6}$ alkyl, —C(=O)—R$^{11}$, and —C(=O)—O—R$^{10}$, wherein,
R$^{10}$ is selected from C$_{1-6}$ alkyl and C$_{3-6}$ cycloalkyl; and
R$^{11}$ is selected from —NH$_2$, —CF$_3$, C$_{1-6}$ alkyl, and C$_{3-6}$ cycloalkyl; and
R$^9$ is selected from hydrogen and C$_{1-3}$ alkyl.

According to the present invention, compounds have the structure of Formula (1):

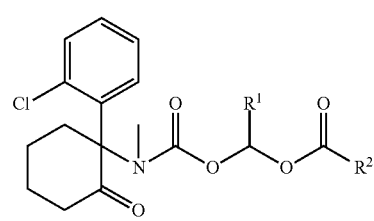

(1)

or a pharmaceutically acceptable salt thereof, wherein,
R$^1$ is selected from hydrogen and C$_{1-6}$ alkyl; and
R$^2$ is selected from a moiety of Formula (6):

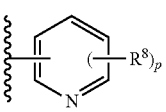

(6)

wherein,
p is an integer from 1 to 3; and
each R$^8$ is independently selected from hydrogen, C$_{1-6}$ alkyl, and —NH$_2$.

According to the present invention, pharmaceutical compositions comprise a compound according to the present invention or a pharmaceutically acceptable salt thereof.

According to the present invention, methods of providing a therapeutically effective amount of a ketamine in the systemic circulation of a patent comprise administering to the patient in need thereof, a compound according to the present invention or a pharmaceutically acceptable salt thereof.

According to the present invention, methods of treating a disease in a patient, wherein the disease is known to be treated by administering ketamine, comprise administering to a patient in need thereof, a pharmaceutically acceptable amount of a compound according to the present invention or a pharmaceutically acceptable salt thereof.

According to the present invention, methods of treating a disease in a patient, wherein the disease is known to be treated by administering ketamine, comprise administering to a patient in need thereof, a pharmaceutically acceptable amount of a pharmaceutical composition according to the present invention.

DETAILED DESCRIPTION

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, such as the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by chemical structure and/or by chemical name. Compounds are named using the ChemBioDraw Ultra 14.0.0.117 (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing "Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ".

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Metabolic intermediate" refers to a compound that is formed in vivo by metabolism of a parent compound and that further undergoes reaction in vivo to release an active agent. Compounds of Formula (1) are acyloxyalkyl derivatives of ketamine that are metabolized in vivo to provide the corresponding metabolic intermediates. Metabolic intermediates undergo nucleophilic cyclization to release ketamine and one or more reaction products. It is desirable that the reaction products or metabolites thereof not be toxic.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety typically via a functional group, to a drug. For example, referring to compounds of Formula (1), an acyloxyalkyl promoiety bonded to the drug ketamine, via the amide group of ketamine. Compounds of Formula (1) are prodrugs of ketamine that can be metabolized within a patient's body to release ketamine.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. Acyloxyalkyl derivatives provided by the present disclosure are prodrugs of ketamine. The acyloxyalkyl promoiety has the structure: For example, for a compound of Formula (1), an acyloxy promoiety has the structure:

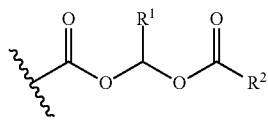

where $R^1$ and $R^2$ are defined as for Formula (1). The acyloxyalkyl promoiety is cleaved in vivo to release ketamine into the systemic circulation.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-5}$ alkyl. Each substituent can be independently selected from deuterio, halogen, —NH$_2$, —OH, $C_{1-3}$ alkoxy, and $C_{1-3}$ alkyl, trifluoromethyl, and trifluoromethyl. Each substituent can be independently selected from deuterio, —OH, methyl, ethyl, trifluoromethyl, methoxy, ethoxy, and trifluoromethoxy. Each substituent can be selected from deuterio, $C_{1-3}$ alkyl, =O, $C_{1-3}$ alkyl, $C_{1-3}$ alkoxy, and phenyl. Each substituent can be selected from deuterio, —OH, —NH$_2$, $C_{1-3}$ alkyl, and $C_{1-3}$ alkoxy.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made to certain compounds and methods. The disclosed embodiments are not intended to be limiting of the claims. To the contrary, the claims are intended to cover all alternatives, modifications, and equivalents.

Ketamine is currently used for acute pain management, chronic pain management, for the treatment of major depression, bipolar disorder and suicidal behavior, and as an anti-inflammatory agent. Ketamine has poor oral bioavailability. Compounds provided by the present disclosure are acyloxyalkyl prodrugs of ketamine. The ketamine acyloxyalkyl prodrugs exhibit enhanced oral bioavailability compared to ketamine. In the ketamine prodrugs a promoiety is bonded to the amide group. In vivo, the acyloxyalkyl is cleaved to release ketamine in the systemic circulation. Ketamine, 2-(2-chlorophenyl)-2-(methylamino)cyclohexan-1-one, has the structure:

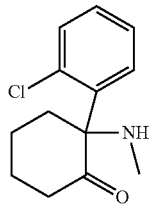

and both the (S)- and (R)-isomers are pharmacologically active. Ketamine has an oral bioavailability in humans of about 20% (% F). The ketamine prodrugs provided by the present disclosure can be used with controlled release and with sustained release oral dosage forms.

Compounds provided by the present disclosure are prodrugs of ketamine. Following oral administration, the compounds provide a therapeutically effective amount of ketamine in the systemic circulation of a patient. Ketamine derivatives provided by the present disclosure exhibit an oral bioavailability (% F) of ketamine greater orally administered ketamine and an improved pharmacokinetic profile.

Compounds provided by the present disclosure following oral administration can provide a therapeutically effective amount of a metabolite of ketamine in the systemic circulation of a patient. Metabolites of ketamine such as, for example, (S)-norketamine, (R)-norketamine, (2S,6S)-hydroxynorketamine, and (2R,6R)-hydroxynorketamine are considered to be therapeutically effective for treating certain diseases.

Ketamine derivatives provided by the present disclosure can have the structure of Formula (1):

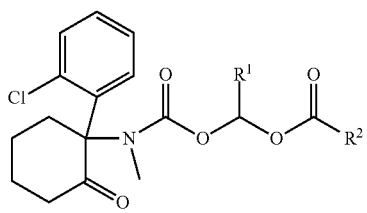
(1)

or a pharmaceutically acceptable salt thereof, wherein,
$R^1$ can be selected from hydrogen and $C_{1-6}$ alkyl; and
$R^2$ can be selected from a moiety of Formula (2), a moiety of Formula (3), a moiety of Formula (4), and a moiety of Formula (5):

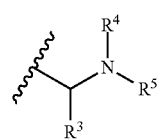
(2)

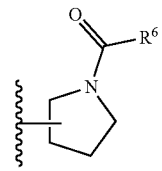
(3)

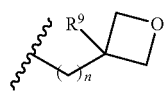
(4)

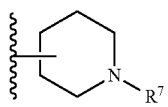
(5)

wherein,
$R^3$ can be selected from hydrogen, $C_{1-6}$ alkyl, and $C_{7-12}$ arylalkyl;
$R^4$ can be selected from hydrogen and $C_{1-6}$ alkyl;
$R^5$ can be selected from hydrogen, $C_{1-6}$ alkyl, —C(=O)—$R^{10}$, and —C(=O)—O—$R^{10}$, wherein
$R^1$ can be selected from $C_{1-6}$ alkyl and $C_{3-6}$ cycloalkyl;
$R^6$ can be selected from $C_{1-6}$ alkyl, $C_{1-6}$ alkoxy, and —$CF_3$;
n can be an integer from 0 to 3;
$R^7$ is selected from hydrogen, $C_{1-6}$ alkyl, —C(=O)—$R^{11}$, and —C(=O)—O—$R^{10}$, wherein,
$R^{10}$ is selected from $C_{1-6}$ alkyl and $C_{3-6}$ cycloalkyl; and
$R^{11}$ is selected from —$NH_2$, —$CF_3$, $C_{1-6}$ alkyl, and $C_{3-6}$ cycloalkyl; and
$R^9$ is selected from hydrogen and $C_{1-3}$ alkyl.

In compounds of Formula (1), the carbon atom to which $R^1$ is bonded is in the (S) configuration.

In compounds of Formula (1), the carbon atom to which $R^1$ is bonded is in the (R) configuration.

In compounds of Formula (1), $R^1$ can be hydrogen.

In compounds of Formula (1), $R^1$ can be selected from methyl, ethyl, n-propyl and iso-propyl.

In compounds of Formula (1), $R^2$ can be a moiety having the structure of Formula (2).

In moieties of Formula (2), $R^3$ can be hydrogen.

In moieties of Formula (2), $R^3$ can be $C_{1-6}$ alkyl.

In moieties of Formula (2), $R^3$ can be selected from methyl, ethyl, n-propyl, isopropyl, isobutyl and 2-methylpropyl.

In moieties of Formula (2), $R^3$ can be $C_{7-12}$ arylalkyl.

In moieties of Formula (2), $R^3$ can be selected from benzyl and phenethyl.

In moieties of Formula (2), the carbon atom to which $R^3$ is bonded is in the (S) configuration.

In moieties of Formula (2), the carbon atom to which $R^3$ is bonded is in the (R) configuration.

In moieties of Formula (2), $R^4$ can be hydrogen.

In moieties of Formula (2), $R^4$ can be $C_{1-6}$ alkyl.

In moieties of Formula (2), $R^4$ can be selected from methyl, ethyl, n-propyl, and isopropyl.

In moieties of Formula (2), $R^5$ can be $C_{1-6}$ alkyl.

In moieties of Formula (2), $R^5$ can be selected from methyl, ethyl, n-propyl, and isopropyl.

In moieties of Formula (2), $R^5$ can be hydrogen.

In moieties of Formula (2), $R^5$ can be —C(=O)—$R^{10}$, and $R^{10}$ can be selected from $C_{1-6}$ alkyl, and $C_{3-6}$ cycloalkyl.

In moieties of Formula (2), $R^5$ can be —C(=O)—$R^{10}$, $R^{10}$ can be —$CF_3$.

In moieties of Formula (2), $R^5$ can be —C(=O)—$R^{10}$, and $R^{10}$ can be $C_{1-6}$ alkyl.

In moieties of Formula (2), $R^5$ can be —C(=O)—$R^{10}$, and $R^{10}$ can be selected from methyl, ethyl, n-propyl, and isopropyl.

In moieties of Formula (2), $R^5$ can be —C(=O)—$R^{10}$, and $R^{10}$ can be $C_{3-6}$ cycloalkyl.

In moieties of Formula (2), $R^5$ can be —C(=O)—$R^{10}$, and $R^{10}$ can be selected from $C_{1-6}$ alkyl and $C_{3-6}$ cycloalkyl.

In moieties of Formula (2), $R^5$ can be —C(=O)—O—$R^{10}$, and $R^{10}$ can be $C_{1-6}$ alkyl.

In moieties of Formula (2), $R^5$ can be —C(=O)—O—$R^{10}$, and $R^{10}$ can be selected from methyl, ethyl, n-propyl, and isopropyl.

In moieties of Formula (2), $R^5$ can be —C(=O)—O—$R^{10}$, and $R^{10}$ can be $C_{3-6}$ cycloalkyl.

In moieties of Formula (2), $R^5$ can be —C(=O)—O—$R^{10}$, and $R^{10}$ can be —$CF_3$.

In moieties of Formula (2), $R^4$ can be hydrogen and $R^5$ can be $C_{1-6}$ alkyl.

In moieties of Formula (2), $R^4$ can be $C_{1-6}$ alkyl and $R^5$ can be $C_{1-6}$ alkyl.

In moieties of Formula (2), $R^4$ can be hydrogen and $R^5$ can be —C(=O)—$R^{10}$.

In moieties of Formula (2), $R^4$ can be $C_{1-6}$ alkyl and $R^5$ can be —C(=O)—$R^{10}$.

In moieties of Formula (2), $R^4$ can be hydrogen and $R^5$ can be —C(=O)—O—$R^{10}$.

In moieties of Formula (2), $R^4$ can be $C_{1-6}$ alkyl and $R^5$ can be —C(=O)—O—$R^{10}$.

In compounds of Formula (1), $R^2$ can be a moiety having the structure of Formula (3).

In moieties of Formula (3), $R^6$ can be $C_{1-6}$ alkyl.

In moieties of Formula (3), $R^6$ can be selected from methyl, ethyl, n-propyl, and isopropyl.

In moieties of Formula (3), $R^6$ can be $C_{1-6}$ alkoxy.

In moieties of Formula (3), $R^6$ can be selected from methoxy, ethoxy, n-propoxy, and isopropoxy.

In compounds of Formula (1), $R^2$ can be a moiety having the structure of Formula (4).

In moieties of Formula (4), n can be 0, 1, 2, or 3.

In moieties of Formula (4), n can be 0.

In moieties of Formula (4), n can be 1.

In moieties of Formula (4), $R^9$ can be hydrogen.

In moieties of Formula (4), $R^9$ can be selected from methyl, ethyl, n-propyl, and isopropyl.

In compounds of Formula (1), $R^2$ can be a moiety having the structure of Formula (5).

In moieties of Formula (5), $R^2$ can be piperidin-2-yl, piperidine-3-yl, and piperidin-4-yl.

In moieties of Formula (5), $R^7$ can be hydrogen.

In moieties of Formula (5), $R^7$ can be $C_{1-6}$ alkyl.

In moieties of Formula (5), $R^7$ can be —C(=O)—$R^{11}$, and $R^{11}$ can be selected from —$NH_2$, $C_{1-6}$ alkyl, and $C_{3-6}$ cycloalkyl.

In moieties of Formula (5), $R^7$ can be —C(=O)—$R^{11}$, and $R^{11}$ can be —$NH_2$.

In moieties of Formula (5), $R^7$ can be —C(=O)—$R^{11}$, and $R^{11}$ can be $C_{1-6}$ alkyl.

In moieties of Formula (5), $R^7$ can be —C(=O)—$R^{11}$, and $R^{11}$ can be selected from methyl, ethyl, n-propyl, and isopropyl.

In moieties of Formula (5), $R^7$ can be —C(=O)—$R^{11}$, and $R^{11}$ can be $C_{3-6}$ cycloalkyl.

In moieties of Formula (5), $R^7$ can be —C(=O)—O—$R^{10}$, and $R^{10}$ can be selected from $C_{1-6}$ alkyl and $C_{3-6}$ cycloalkyl.

In moieties of Formula (5), $R^7$ can be —C(=O)—O—$R^{10}$, and $R^{10}$ can be $C_{1-6}$ alkyl.

In moieties of Formula (5), $R^7$ can be —C(=O)—O—$R^{10}$, and $R^{10}$ can be selected from methyl, ethyl, n-propyl, and isopropyl.

In moieties of Formula (5), $R^7$ can be —C(=O)—O—$R^{10}$, and $R^{10}$ can be $C_{3-6}$ cycloalkyl.

A compound of Formula (1) can be the (R) isomer and can have the structure of Formula (1a):

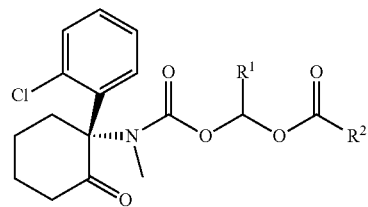

(1a)

A compound of Formula (1) can be the (S) isomer and can have the structure of Formula (1b):

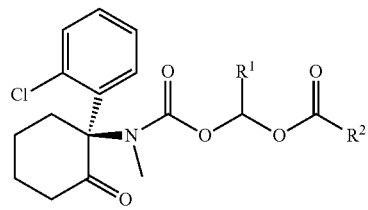

(1b)

A compound of Formula (1), a compound of Formula (1a), and a compound of Formula (1b) can be a pharmaceutically acceptable salt. For example, a compound of Formula (1) can be the hydrochloride salt.

A compound of Formula (1) can be a pharmaceutically acceptable salt of a compound of Formula (1), a hydrate thereof, or a solvate of any of the foregoing.

A compound of Formula (1) can be selected from:
1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl (tert-butoxycarbonyl)glycinate (4);
1-((((S)-1-(2-chlorophenyl)-2-oxocyclohexyl)(methyl)carbamoyl)oxy)ethyl (tert-butoxycarbonyl)-L-valinate (5);
1-((((S)-1-(2-chlorophenyl)-2-oxocyclohexyl)(methyl)carbamoyl)oxy)ethyl 2-(3-methyloxetan-3-yl)acetate (6);
1-((((S)-1-(2-chlorophenyl)-2-oxocyclohexyl)(methyl)carbamoyl)oxy)ethyl acetyl-L-alaninate (7);
1-((((S)-1-(2-chlorophenyl)-2-oxocyclohexyl)(methyl)carbamoyl)oxy)ethyl acetyl-L-valinate (8);
1-((((S)-1-(2-chlorophenyl)-2-oxocyclohexyl)(methyl)carbamoyl)oxy)ethyl-1-methylpiperidine-4-carboxylate (17);
1-((((S)-1-(2-chlorophenyl)-2-oxocyclohexyl)(methyl)carbamoyl)oxy)ethyl isobutyrylglycinate (19);
(S)-(((1-(2-chlorophenyl)-2-oxocyclohexyl)(methyl)carbamoyl)oxy)methyl 2-(3-methyloxetan-3-yl)acetate (22);

1-((((S)-1-(2-chlorophenyl)-2-oxocyclohexyl)(methyl)carbamoyl)oxy)propyl 2-(3-methyloxetan-3-yl)acetate (24);
1-((((S)-1-(2-chlorophenyl)-2-oxocyclohexyl)(methyl)carbamoyl)oxy)-2-methylpropyl 2-(3-methyloxetan-3-yl)acetate (26);
1-((((S)-1-(2-chlorophenyl)-2-oxocyclohexyl)(methyl)carbamoyl)oxy)propyl acetylglycinate (27);
1-((((S)-1-(2-chlorophenyl)-2-oxocyclohexyl)(methyl)carbamoyl)oxy)-2-methylpropyl acetylglycinate (28);
(S)-(((1-(2-chlorophenyl)-2-oxocyclohexyl)(methyl)carbamoyl)oxy)methyl acetylglycinate (31);
((((S)-1-(2-chlorophenyl)-2-oxocyclohexyl)(methyl)carbamoyl)oxy)methyl acetyl-L-valinate (32);
((((S)-1-(2-chlorophenyl)-2-oxocyclohexyl)(methyl)carbamoyl)oxy)methyl acetyl-L-alaninate (33);
(S)-(((1-(2-chlorophenyl)-2-oxocyclohexyl)(methyl)carbamoyl)oxy)methyl isobutyrylglycinate (34);
((((S)-1-(2-chlorophenyl)-2-oxocyclohexyl)(methyl)carbamoyl)oxy)methyl isobutyryl-L-alaninate (35);
((((S)-1-(2-chlorophenyl)-2-oxocyclohexyl)(methyl)carbamoyl)oxy)methyl isobutyryl-L-valinate (36);
((((S)-1-(2-chlorophenyl)-2-oxocyclohexyl)(methyl)carbamoyl)oxy)methyl L-valinate (37);
(S)-(((1-(2-chlorophenyl)-2-oxocyclohexyl)(methyl)carbamoyl)oxy)methyl glycinate (38);
((((S)-1-(2-chlorophenyl)-2-oxocyclohexyl)(methyl)carbamoyl)oxy)methyl dimethyl-L-valinate (39);
(S)-(((1-(2-chlorophenyl)-2-oxocyclohexyl)(methyl)carbamoyl)oxy)methyl N-acetyl-N-methylglycinate (40);
1-((((S)-1-(2-chlorophenyl)-2-oxocyclohexyl)(methyl)carbamoyl)oxy)ethyl N-acetyl-N-methylglycinate (41);
1-((((S)-1-(2-chlorophenyl)-2-oxocyclohexyl)(methyl)carbamoyl)oxy)ethyl propionylglycinate (42);
(S)-(((1-(2-chlorophenyl)-2-oxocyclohexyl)(methyl)carbamoyl)oxy)methyl propionylglycinate (43);
((((S)-1-(2-chlorophenyl)-2-oxocyclohexyl)(methyl)carbamoyl)oxy)methyl L-alaninate (44);
1-((((S)-1-(2-chlorophenyl)-2-oxocyclohexyl)(methyl)carbamoyl)oxy)ethyl (2,2,2-trifluoroacetyl)glycinate (45);
(S)-(((1-(2-chlorophenyl)-2-oxocyclohexyl)(methyl)carbamoyl)oxy)methyl (2,2,2-trifluoroacetyl)glycinate (46);
1-((((S)-1-(2-chlorophenyl)-2-oxocyclohexyl)(methyl)carbamoyl)oxy)ethyl dimethyl-L-alaninate (47);
((((S)-1-(2-chlorophenyl)-2-oxocyclohexyl)(methyl)carbamoyl)oxy)methyl (2,2,2-trifluoroacetyl)-L-valinate (48);
1-((((S)-1-(2-chlorophenyl)-2-oxocyclohexyl)(methyl)carbamoyl)oxy)propyl (2,2,2-trifluoroacetyl)glycinate (49);
((((S)-1-(2-chlorophenyl)-2-oxocyclohexyl)(methyl)carbamoyl)oxy)methyl (2,2,2-trifluoroacetyl)-L-alaninate (50);
1-((((S)-1-(2-chlorophenyl)-2-oxocyclohexyl)(methyl)carbamoyl)oxy)-2-methylpropyl (2,2,2-trifluoroacetyl)glycinate (51);
1-((((S)-1-(2-chlorophenyl)-2-oxocyclohexyl)(methyl)carbamoyl)oxy)ethyl (2,2,2-trifluoroacetyl)-L-valinate (52);
1-((((S)-1-(2-chlorophenyl)-2-oxocyclohexyl)(methyl)carbamoyl)oxy)ethyl (2,2,2-trifluoroacetyl)-L-alaninate (53);
1-((((S)-1-(2-chlorophenyl)-2-oxocyclohexyl)(methyl)carbamoyl)oxy)ethyl acetyl-L-leucinate (57);
((((S)-1-(2-chlorophenyl)-2-oxocyclohexyl)(methyl)carbamoyl)oxy)methyl acetyl-L-leucinate (58);
1-((((S)-1-(2-chlorophenyl)-2-oxocyclohexyl)(methyl)carbamoyl)oxy)ethyl acetyl-L-alloisoleucinate (59);
((((S)-1-(2-chlorophenyl)-2-oxocyclohexyl)(methyl)carbamoyl)oxy)methyl acetyl-L-alloisoleucinate (60);
1-((((R)-1-(2-chlorophenyl)-2-oxocyclohexyl)(methyl)carbamoyl)oxy)ethyl acetylglycinate (62);
1-((((R)-1-(2-chlorophenyl)-2-oxocyclohexyl)(methyl)carbamoyl)oxy)ethyl 2-(3-methyloxetan-3-yl)acetate (63);
1-((((R)-1-(2-chlorophenyl)-2-oxocyclohexyl)(methyl)carbamoyl)oxy)ethyl acetyl-L-alaninate (64);
1-((((R)-1-(2-chlorophenyl)-2-oxocyclohexyl)(methyl)carbamoyl)oxy)ethyl acetyl-L-valinate (65);
(R)-(((1-(2-chlorophenyl)-2-oxocyclohexyl)(methyl)carbamoyl)oxy)methyl 2-(3-methyloxetan-3-yl)acetate (66);
(((1-(2-chlorophenyl)-2-oxocyclohexyl)(methyl)carbamoyl)oxy)methyl acetylglycinate (68);
(((1-(2-chlorophenyl)-2-oxocyclohexyl)(methyl)carbamoyl)oxy)methyl acetyl-L-valinate (69);
(((1-(2-chlorophenyl)-2-oxocyclohexyl)(methyl)carbamoyl)oxy)methyl acetyl-L-alaninate (70);
((((R)-1-(2-chlorophenyl)-2-oxocyclohexyl)(methyl)carbamoyl)oxy)methyl acetyl-L-leucinate (71);
(((1-(2-chlorophenyl)-2-oxocyclohexyl)(methyl)carbamoyl)oxy)methyl acetyl-L-alloisoleucinate (72);
((((S)-1-(2-chlorophenyl)-2-oxocyclohexyl)(methyl)carbamoyl)oxy)methyl dimethyl-L-lloisoleucinate hydrogen chloride (74);
((((S)-1-(2-chlorophenyl)-2-oxocyclohexyl)(methyl)carbamoyl)oxy)methyl methyl-L-valinate hydrogen chloride (75);
((((S)-1-(2-chlorophenyl)-2-oxocyclohexyl)(methyl)carbamoyl)oxy)methyl dimethyl-L-leucinate hydrogen chloride (76);
((((S)-1-(2-chlorophenyl)-2-oxocyclohexyl)(methyl)carbamoyl)oxy)methyl diethyl-L-valinate hydrogen chloride (77);
((((S)-1-(2-chlorophenyl)-2-oxocyclohexyl)(methyl)carbamoyl)oxy)methyl methyl-L-alaninate 2,2,2-trifluoroacetic acid (78);
((((S)-1-(2-chlorophenyl)-2-oxocyclohexyl)(methyl)carbamoyl)oxy)methyl dipropyl-L-valinate (79);
((((S)-1-(2-chlorophenyl)-2-oxocyclohexyl)(methyl)carbamoyl)oxy)methyl L-leucinate hydrogen chloride (80);
((((S)-1-(2-chlorophenyl)-2-oxocyclohexyl)(methyl)carbamoyl)oxy)methyl isopropyl-L-valinate hydrogen chloride (81);
((((S)-1-(2-chlorophenyl)-2-oxocyclohexyl)(methyl)carbamoyl)oxy)methyl propyl-L-valinate hydrogen chloride (82);
((((S)-1-(2-chlorophenyl)-2-oxocyclohexyl)(methyl)carbamoyl)oxy)methyl ethyl-L-valinate (83);
(piperidine-4-carboxyloyloxy)methyl (S)-1-(2-chlorophenyl)-2-oxocyclohexylmethylcarbamate (86);
((((S)-1-(2-chlorophenyl)-2-oxocyclohexyl)(methyl)carbamoyl)oxy)methyl acetyl-D-prolinate (87);
((((S)-1-(2-chlorophenyl)-2-oxocyclohexyl)(methyl)carbamoyl)oxy)methyl acetyl-L-phenylalaninate (88) ((((S)-1-(2-chlorophenyl)-2-oxocyclohexyl)(methyl)carbamoyl)oxy)methyl acetyl-L-tyrosinate (89);
1-((((S)-1-(2-chlorophenyl)-2-oxocyclohexyl)(methyl)carbamoyl)oxy)ethyl dimethyl-L-valinate (90); and
a pharmaceutically acceptable salt of any of the foregoing.

A compound of Formula (1) can be 1-((((S)-1-(2-chlorophenyl)-2-oxocyclohexyl)(methyl)carbamoyl)oxy)ethyl 2-aminonicotinate.

A compound of Formula (1) can be selected from:
1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl 2-(3-methyloxetan-3-yl)acetate (6);

1-((((S)-1-(2-chlorophenyl)-2-oxocyclohexyl)(methyl)carbamoyl)oxy)ethyl acetyl-L-alaninate (7);
1-((((S)-1-(2-chlorophenyl)-2-oxocyclohexyl)(methyl)carbamoyl)oxy)ethyl isonicotinate (18);
1-((((S)-1-(2-chlorophenyl)-2-oxocyclohexyl)(methyl)carbamoyl)oxy)ethyl isobutyrylglycinate (19);
(S)-(((1-(2-chlorophenyl)-2-oxocyclohexyl)(methyl)carbamoyl)oxy)methyl 2-(3-methyloxetan-3-yl)acetate (22);
1-((((S)-1-(2-chlorophenyl)-2-oxocyclohexyl)(methyl)carbamoyl)oxy)propyl acetylglycinate (27);
1-((((S)-1-(2-chlorophenyl)-2-oxocyclohexyl)(methyl)carbamoyl)oxy)-2-methylpropyl acetylglycinate (28);
((((S)-1-(2-chlorophenyl)-2-oxocyclohexyl)(methyl)carbamoyl)oxy)methyl dimethyl-L-valinate (39);
((((S)-1-(2-chlorophenyl)-2-oxocyclohexyl)(methyl)carbamoyl)oxy)methyl acetyl-L-alloisoleucinate (60); and
a pharmaceutically acceptable salt of any of the foregoing.

A compound provided by the present disclosure can have the structure of Formula (1):

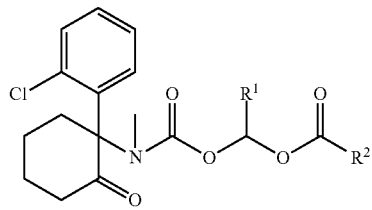

or a pharmaceutically acceptable salt thereof, wherein,
$R^1$ can be selected from hydrogen and $C_{1-6}$ alkyl; and
$R^2$ can be selected from a moiety of Formula (6):

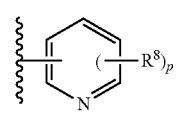

wherein,
p is an integer from 1 to 3; and
each $R^8$ is independently selected from hydrogen, $C_{1-6}$ alkyl, and $-NH_2$.

In compounds of Formula (1) in which $R^2$ is a moiety of Formula (6), the carbon atom to which $R^1$ can be bonded can be in the (S) configuration.

In compounds of Formula (1) in which $R^2$ is a moiety of Formula (6), the carbon atom to which $R^1$ can be bonded can be in the (R) configuration.

In compounds of Formula (1) in which $R^2$ is a moiety of Formula (6), $R^1$ can be hydrogen.

In compounds of Formula (1) in which $R^2$ is a moiety of Formula (6), $R^1$ can be $C_{1-6}$ alkyl.

In compounds of Formula (1) in which $R^2$ is a moiety of Formula (6, $R^1$ can be selected from methyl, ethyl, propyl, and isopropyl.

In moieties of Formula (6), p can be 1.
In moieties of Formula (6), p can be 2.
In moieties of Formula (6), p can be 3.
In moieties of Formula (6), each $R^8$ can be hydrogen.
In moieties of Formula (6), each R can independently be $C_{1-6}$ alkyl.

In moieties of Formula (6), each $R^8$ can independently be selected from methyl, ethyl, propyl, and isopropyl.

In moieties of Formula (6), each R can independently be $-NH_2$.

In compounds of Formula (1), in which $R^2$ is a moiety of Formula (6), the compound can be selected from:
1-((((S)-1-(2-chlorophenyl)-2-oxocyclohexyl)(methyl)carbamoyl)oxy)ethyl nicotinate (14);
1-((((S)-1-(2-chlorophenyl)-2-oxocyclohexyl)(methyl)carbamoyl)oxy)ethyl isonicotinate (18);
(S)-(((1-(2-chlorophenyl)-2-oxocyclohexyl)(methyl)carbamoyl)oxy)methyl nicotinate (29);
(S)-(((1-(2-chlorophenyl)-2-oxocyclohexyl)(methyl)carbamoyl)oxy)methyl 4-methylnicotinate (54);
(S)-(((1-(2-chlorophenyl)-2-oxocyclohexyl)(methyl)carbamoyl)oxy)methyl 2-methylnicotinate (55);
(S)-(((1-(2-chlorophenyl)-2-oxocyclohexyl)(methyl)carbamoyl)oxy)methyl 6-methylnicotinate (56);
(S)-(((1-(2-chlorophenyl)-2-oxocyclohexyl)(methyl)carbamoyl)oxy)methyl 2-aminonicotinate (61);
(R)-(((1-(2-chlorophenyl)-2-oxocyclohexyl)(methyl)carbamoyl)oxy)methyl nicotinate (67);
(R)-(((1-(2-chlorophenyl)-2-oxocyclohexyl)(methyl)carbamoyl)oxy)methyl 2-aminonicotinate (73); and
a pharmaceutically acceptable salt of any of the foregoing.

In compounds of Formula (1) in which $R^2$ is a moiety of Formula (6) the compound can be the (R)-isomer having the structure of Formula (1a):

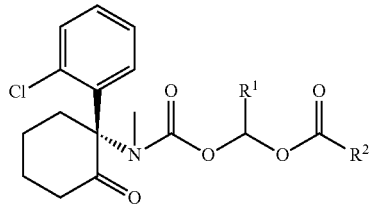

In compounds of Formula (1) in which $R^2$ is a moiety of Formula (6) the compound can be the (S)-isomer having the structure of Formula (1b):

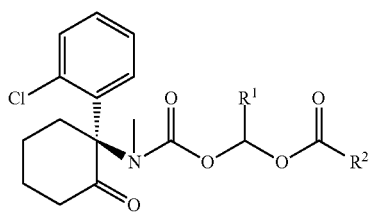

In compounds of Formula (1) in which $R^2$ is a moiety of Formula (6) the compound can comprise a hydrochloride salt.

Compounds of Formula (1) can have the structure of subgenus (1A), wherein,
$R^1$ can be selected from hydrogen and methyl;
$R^2$ can be a moiety of Formula (2);
$R^3$ can be selected from hydrogen and $C_{1-4}$ alkyl;
$R^4$ can be selected from hydrogen and $C_{1-3}$ alkyl; and
$R^5$ can be selected from $C_{1-3}$ alkyl and $-C(=O)-R^{10}$, where $R^{10}$ can be selected from $C_{1-3}$ alkyl.

In compounds of subgenus (1A), $R^1$ can be hydrogen.

In compounds of subgenus (1A), $R^1$ can be methyl.

In compounds of subgenus (1A), the carbon atom to which $R^1$ is bonded can be in the (S) configuration.

In compounds of subgenus (1A), the carbon atom to which $R^1$ is bonded can be in the (R) configuration.

In compounds of subgenus (1A), $R^3$ can be hydrogen.

In compounds of subgenus (1A), $R^3$ can be $C_{1-3}$ alkyl.

In compounds of subgenus (1A), the carbon atom to which $R^3$ is bonded can be in the (S) configuration.

In compounds of subgenus (1A), the carbon atom to which $R^3$ is bonded can be in the (R) configuration.

In compounds of subgenus (1A), $R^4$ can be hydrogen.

In compounds of subgenus (1A), $R^4$ can be $C_{1-3}$ alkyl.

In compounds of subgenus (1A), $R^5$ can be $C_{1-3}$ alkyl.

In compounds of subgenus (1A), $R^5$ can be —C(=O)—$R^{10}$.

Compounds of Formula (1) can have the structure of subgenus (4A), wherein, $R^1$ can be selected from hydrogen and methyl;
$R^2$ can be a moiety of Formula (4);
n can be 1; and
$R^9$ can be selected from $C_{1-3}$ alkyl.

In compounds of subgenus (4A), $R^1$ can be hydrogen.

In compounds of subgenus (4A), $R^1$ can be methyl.

In compounds of subgenus (4A), the carbon atom to which $R^1$ is bonded can be in the (S) configuration.

In compounds of subgenus (4A), the carbon atom to which $R^1$ is bonded can be in the (R) configuration.

In compounds of subgenus (4A), $R^3$ can be hydrogen.

In compounds of subgenus (4A), $R^3$ can be methyl.

Compounds of Formula (1) can have the structure of subgenus (5A), wherein, $R^1$ can be selected from hydrogen and methyl;
$R^2$ can be a moiety of Formula (5); and
$R^7$ can be selected from $C_{1-3}$ alkyl.

In compounds of subgenus (5A), $R^1$ can be hydrogen.

In compounds of subgenus (5A), $R^1$ can be methyl.

In compounds of subgenus (5A), the carbon atom to which $R^1$ is bonded can be in the (S) configuration.

In compounds of subgenus (5A), the carbon atom to which $R^1$ is bonded can be in the (R) configuration.

In compounds of subgenus (5A), $R^7$ can be methyl.

Compounds of Formula (1) can have the structure of subgenus (6A), wherein, $R^1$ can be selected from hydrogen and methyl;
$R^2$ can be a moiety of Formula (6); and
$R^8$ is selected from —$NH_2$.

In compounds of subgenus (6A), $R^1$ can be hydrogen.

In compounds of subgenus (6A), $R^1$ can be methyl.

In compounds of subgenus (6A), the carbon atom to which $R^1$ is bonded can be in the (S) configuration.

In compounds of subgenus (6A), the carbon atom to which $R^1$ is bonded can be in the (R) configuration.

Compounds of Formula (1) can be synthesized using methods known in the art. Reacting (S)-ketamine or (R)-ketamine with 1-chloroethyl carbonochloridate in the presence of a basic catalyst such as N,N-disisopropylethylamine (DIPEA) to provide the corresponding 1-chloroethyl (1-(2-chlorophenyl)-2-oxocyclohexyl)(methyl)carbamate, which is reacted with a substituted carboxylic acid in the presence of an amine catalyst to provide the corresponding ketamine prodrug. Specific synthetic reactions are provided in the experimental examples.

Pharmaceutical compositions provided by the present disclosure comprise a compound of Formula (1) or a pharmaceutically acceptable salt thereof. Pharmaceutical compositions provided by the present disclosure comprise a compound of Formula (1) or a pharmaceutically acceptable salt thereof and at least one pharmaceutically acceptable excipient. Pharmaceutically acceptable excipients are known.

Pharmaceutical compositions provided by the present disclosure can be formulated for oral administration. The compositions may be in the form, for example, of a solution, a suspension, a tablet, or a lozenge.

An oral dosage form can comprise a therapeutically effective amount of a compound of Formula (1).

An oral dosage form can comprise a sustained release oral dosage form.

Following oral administration to a patient the compound of Formula (1) is absorbed by the gastrointestinal tract into the systemic circulation where the promoiety is cleaved to provide a systemic circulation of ketamine.

A compound of Formula (1) may be incorporated into pharmaceutical compositions to be administered orally. Oral administration of such pharmaceutical compositions results in uptake of the compound of Formula (1) throughout or in a portion of the gastrointestinal tract and entry into the systemic circulation.

An oral dosage form provided by the present disclosure may be a controlled release dosage form. Controlled delivery technologies can improve the absorption of a drug in a particular region or regions of the gastrointestinal tract.

Controlled drug delivery systems may be designed to deliver a drug in such away that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution-controlled systems, diffusion-controlled systems, ion exchange resins, osmotically controlled systems, erodable matrix systems, pH independent formulations, and gastric retention systems.

Regardless of the specific type of controlled release oral dosage form used, a compound of Formula (1) may be released from an orally administered dosage form over a sufficient period of time to provide prolonged therapeutic concentrations of the compound of Formula (1) in the plasma and/or blood of a patient. Following oral administration, a dosage form comprising a compound of Formula (1) may provide a therapeutically effective concentration of the corresponding drug in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of the drug is maintained may be the same or different. The continuous period of time during which a therapeutically effective plasma concentration of the drug is maintained may begin shortly after oral administration or following a time interval.

Following oral administration, and absorption of a compound of Formula (1) into the systemic circulation, dosage forms comprising a compound of Formula (1) can provide a therapeutic or prophylactic concentration of ketamine in the plasma and/or blood of a patient for a time period of at least about 4 hours, for at least about 8 hours, for at least about 12 hours, for at least about 16 hours, for at least about 20 hours, or for at least about 24 hours following oral administration of the dosage form to the patient.

Regardless of the specific form of sustained release oral dosage form used, a compound of Formula (1) may be released from a dosage form such as an orally administered dosage form, over a sufficient period of time to provide prolonged therapeutic concentrations of a compound of Formula (1) in the blood of a patient enabling administration of the dosage form on only a once or twice per day basis.

Pharmaceutical compositions provided by the present disclosure may be practiced with dosage forms adapted to provide sustained release of a compound of Formula (1) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Sustained release oral dosage forms provided by the present disclosure can release a compound of Formula (1) from the dosage form to facilitate the ability of the compound of Formula (1) to be absorbed from an appropriate region of the gastrointestinal tract, for example, in the small intestine or in the colon. Sustained release oral dosage forms may release a compound of Formula (1) from the dosage form over a period of at least about 4 hours, at least about 8 hours, at least about 12 hours, at least about 16 hours, at least about 20 hours, and in certain embodiments, at least about 24 hours. Sustained release oral dosage forms may release a compound of Formula (1) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 24 hours; where wt % refers to the percent of the total weight of the compound in the dosage form. Sustained release oral dosage forms may release a compound of Formula (1) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 20 hours. Sustained release oral dosage forms may release a compound of Formula (1) from the dosage form in a delivery pattern corresponding to about 0 wt % to about 20 wt % in about 0 to about 2 hours; about 20 wt % to about 50 wt % in about 0 to about 4 hours; about 55 wt % to about 85 wt % in about 0 to about 7 hours; and about 80 wt % to about 100 wt % in about 0 to about 8 hours.

Sustained release oral dosage forms comprising a compound of Formula (1) may provide a concentration of the corresponding drug in the plasma, blood, cerebrospinal fluid, or tissue of a patient over time, following oral administration to the patient. The concentration profile of the drug may exhibit an AUC that is proportional to the dose of the corresponding compound of Formula (1).

The appropriate oral dosage form for a particular pharmaceutical composition provided by the present disclosure may depend, at least in part, on the gastrointestinal absorption properties of a compound of Formula (1), the stability of a compound of Formula (1) in the gastrointestinal tract, the pharmacokinetics of a compound of Formula (1), and the intended therapeutic profile. An appropriate controlled or sustained release oral dosage form may be selected for a particular compound of Formula (1). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

A therapeutically effective concentration of a compound of Formula (1) in the blood or plasma of a patient can be less than an amount that causes unacceptable adverse effects including adverse effects to homeostasis. A therapeutically effective concentration of a compound of Formula (1) in the blood or plasma of a patient can be an amount sufficient to restore and/or maintain homeostasis in the patient. For example, following administration of a therapeutically effective dose of a compound of Formula (1), a therapeutically effective amount of ketamine can be maintained for greater than 1 hour, greater than 2 hours, greater than 3 hours, greater than 4 hours, greater than 5 hours, greater than 6 hours, greater than 7 hours, or greater than 8 hours. For example, following administration of a therapeutically effective dose of a compound of Formula (1), a therapeutically effective amount of ketamine can be maintained, for example, from 1 hour to 10 hours, from 2 hours to 8 hours, from 2 hours to 6 hours, or from 2 hours to 4 hours.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a ketamine derivative may exhibit a high therapeutic index. The data obtained from these cell culture assays and animal studies may be used in formulating a dosage range that is not toxic for use in humans. A dose of a ketamine derivative provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Pharmaceutical compositions provided by the present disclosure may further comprise one or more pharmaceutically active compounds in addition to a compound of Formula (1). Such compounds may be provided to treat the disease being treated with ketamine or to treat a disease, disorder, or condition other than the infectious disease being treated with the compound of Formula (1).

A compound of Formula (1) may be used in combination with at least one other therapeutic agent. A compound of Formula (1) may be administered to a patient together with another compound for treating infectious disease in the patient. The at least one other therapeutic agent may be a second compound encompassed by compounds of Formula (1). A compound of Formula (1) and the at least one other therapeutic agent may act additively or, and in certain embodiments, synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating an infectious disease or a different disease, disorder or condition than the infectious disease. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug and/or to enhance treatment efficacy. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a patient. A pharmaceutical composition comprising a compound of Formula (1) may be co-administered with an active agent having pharmacological effects that enhance the therapeutic efficacy of the compound of Formula (1).

A compound of Formula (1) or a pharmaceutical composition comprising a compound of Formula (1) may be administered in conjunction with an agent known or believed to be effective in treating the disease being treated with ketamine.

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. A kit for use in treating a bacterial infection in a patient comprises a compound of Formula (1) or a pharmaceutically acceptable salt thereof, a pharmaceutically acceptable vehicle for administering the compound, and instructions for administering the compound to a patient. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds of Formula (1) and pharmaceutical compositions thereof can be used to treat a disease known to be or determined to be treated by ketamine.

Compounds of Formula (1) and pharmaceutical compositions thereof can be used to treat a disease known to be or determined to be treated by ketamine and one or more additional therapeutic agents.

For example, compounds of Formula (1) and pharmaceutical compositions thereof can be used to treat a neurological disease, a psychological disease, or pain.

Compounds of Formula (1) and pharmaceutical compositions thereof can be used to treat a neurological disease such as a neurological disease of the central nervous system.

Examples of neurological diseases include Alzheimer's disease; amyotrophic lateral sclerosis; back pain; Bell's palsy; birth defects of the brain and spinal cord; brain aneurysm; brain injury; brain tumor; cerebral palsy; chronic fatigue syndrome; concussion; dementia; disk disease of neck and lower back; dizziness; dystonia; epilepsy; Guillain-Barré syndrome; headache—cluster; headache—tension; migraine; motor neuron disease amyotrophic lateral sclerosis; multiple sclerosis; muscular dystrophy; neuralgia; neurofibromatosis; neuropathy; neuromuscular and related diseases; Parkinson's disease; progressive supranuclear palsy; psychiatric conditions (severe depression, obsessive-compulsive disorder); sciatica; scoliosis; seizures; shingles; spinal cord injury; spinal deformity; spinal disorder (subacute combined degeneration); spine tumor; stroke; traumatic brain injury; and vertigo.

Compounds of Formula (1) and pharmaceutical compositions thereof can be used to treat a neurological disease such as a psychiatric disease.

Example of psychiatric diseases include alcohol or substance use disorder; anxiety disorders including generalized anxiety disorder, panic disorder, phobias, and social anxiety disorder; adult attention deficit/hyperactivity disorder; bipolar disorder including major depressive episode, hypomanic episode, manic episode, and mixed specifier (formerly mixed episode); depression including postpartum depression and seasonal affective disorder; eating disorders; obsessive-compulsive disorder; opioid use disorder symptoms; post-traumatic stress disorder; schizophrenia; dissociative disorders; feeding and eating disorders; sexual and paraphilic disorders; sleep and wake disorders; childhood mental disorders including autism spectrum disorder (formerly Asperger's, autistic disorder, and Rett's), attention deficit/hyperactivity disorder, and autism; personality disorders including antisocial personality disorder, avoidant personality disorder, borderline personality disorder, dependent personality disorder, histrionic personality disorder, multiple personality disorder, see dissociative identity disorder, narcissistic personality disorder, obsessive-compulsive personality disorder, paranoid personality disorder, schizoid personality disorder, and schizotypal personality disorder; and other mental disorders including acute stress disorder, Alzheimer's disease, Parkinson's disease, and psychotic disorder Compounds of Formula (1) and pharmaceutical compositions thereof can be used to treat pain. Examples of pain include acute pain, addiction, advanced prostate cancer, AIDs-related pain, ankylosing spondylitis, arachnoiditis, arthritis, arthrofibrosis, ataxic cerebral palsy, autoimmune atrophic gastritis, autoimmune diseases, avascular necrosis, back pain, Behcet's disease (syndrome), breakthrough pain, burning mouth syndrome, bursitis, cadasil, cancer pain, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pain, chronic pancreatitis, coccyx, collapsed lung (pneumothorax), complementary and alternative medicine, complex regional pain syndrome (rsd), corneal neuropathic pain, Crohn's disease, degenerative disc disease, dependence (physical), depression, Dercum's disease, dermatomyositis, diabetic peripheral neuropathy, dystonia, Ehlers-Danlos syndrome, endometriosis, eosinophilia-myalgia syndrome, erythromelalgia, failed back surgery syndrome, fibromyalgia, gout, growing pains, headaches, herniated disc, hydrocephalus, intercostal neuraligia, interstitial cystitis, irritable bowel syndrome, juvenile dermatositis, knee injury, leg pain, loin pain-haematuria syndrome, lupus, Lyme disease, medullary sponge kidney, meralgia paresthetica, mesothelioma, migraine, mitochondrial disorders, multiple sclerosis, musculoskeletal pain, myofascial pain, myositis, neck pain, neuropathic pain, NSAIDs, occipital neuralgia, osteoarthritis, Paget's disease, parsonage turner syndrome, patient rights, pelvic pain, peripheral neuropathy, phantom limb pain, pinched nerve, polycystic kidney disease, polymyalgia rhuematica, polymyositis, porphyria, post herniorraphy pain syndrome, post mastectomy pain syndrome, post stroke pain, post thorocotomy pain syndrome, postherpetic neuralgia (shingles), post-polio health international, post-polio syndrome, post-traumatic stress disorder, primary lateral sclerosis, psoriatic arthritis, pudendal neuralgia, radiculopathy, Raynaud's disease, restless leg syndrome, rheumatoid arthritis, sacroiliac joint dysfunction, sarcoidosis, Scheuemann's kyphosis disease, sciatica, scoliosis, shingles (herpes zoster), sickle cell, Sjogren's syndrome, sleep apnea, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, TMJ, tolerance, transverse myelitis, trigeminal neuralgia, trigger points, ulcerative colitis, vascular pain, vulvodynia, whiplash.

Ketamine is an NMDA (N-methyl-D-aspartate) receptor antagonist. Thus, compounds provided by the present disclosure which following oral administration, release ketamine into the systemic circulation will be useful in treating diseases for which ketamine and other NMDA receptor antagonists are useful in treating.

NMDA receptor antagonists are known to be useful in treating or are believed to be useful in treating, for example, acute pain, acute traumatic pain, alcohol use disorder, Alzheimer's disease, anxiety disorders, anxious depression, autism spectrum disorder, bipolar depression, bipolar I disorder, bipolar II disorder, chronic pain, cancer pain, cognitive symptom, cortical spreading depolarization, cortical spreading depression, violent/aggressive behavior, depression, fracture pain, head and neck cancer, headache, Huntington's disease, intractable pain, major depression disorder, migraine, mood disorders, neuropathic pain, obsessive compulsive disorder, obstructive sleep apnea syndrome, pancreatic cancer pain, Parkinson's disease, perinatal depression, post-operative cognitive dysfunction, postoperative pain, postpartum depression, post-traumatic stress disorder, pressure ulcer, psychotic-like symptoms, refractory cancer pain, Rett syndrome, schizophrenia, sleep apnea, social anxiety disorder, stress disorders, subarachnoid hemorrhage, substance use disorders, suicide, suicidal ideation, systemic lupus erythematosus, traumatic brain injury, treatment resistant depression, and unipolar depression.

Compounds provided by the present disclosure can be used to treat a disease for which the etiology of the disease is associated with the NMDA.

Method provided by the present disclosure include providing a therapeutically effective amount of ketamine in the systemic circulation of a patient comprising administering to a patient a compound of Formula (1) or a pharmaceutically acceptable salt thereof, or a pharmaceutical composition thereof.

Compounds provided by the present disclosure can be co-administered with other NMDA receptor antagonists including, for example, competitive antagonists such as AP5 (APV, R-2-amino-5-phosphonopentanoate), AP7 (2-amino-7-phosphonoheptanoic acid), copene (3-[(R)-2-carboxypiperazin-4-yl]-prop-2-enyl-1-phosphonic acid), selfotel, and aspartame; uncompetitive channel blockers including minocycline, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ketamine, magnesium, memantine, methoxetamine, nitromemantine, nitrous oxide, PD-137889, phencyclidine, rolicyclidine, tenocyclidine, methoxydine, tiletamine, neramexane, eliprodil, etoxadrol, dexoxadrol, WMS-2539, NEFA, remacemide, delucemine, and 8A-PDHQ, non-competitive antagonists such as aptiganel, HU-211, huperzine A, ibogaine, remacemide, rhynchophylline, and gabapentin; glycine antagonists such as apastinel, NRX-1074, 7-chlorokynurenic acid, 4-chlorokynurenine, 5,7-dichlorokynurenic acid, kynurenic acid, TK-40, 1-aminocyclopropanecarboxylic acid, 1-phenylalanine, and xenon; or a combination of any of the foregoing.

Compounds and compositions provided by the present disclosure can be administered orally.

Compounds provided by the present disclosure, when orally administered, provide an enhanced oral bioavailability of ketamine compared to the oral bioavailability of orally administered ketamine.

In humans, orally administered (50 mg tablet) (S)-ketamine and (R)-ketamine have an oral bioavailability of about 18% with a $C_{max}$ of about 41 ng/mL, a $T_{max}$ of about 31 min, and an $AUC_{0 \to \infty}$ ng×h/mL. Yanagihara et al., *Biopharmaceutics & Drug Disposition,* 24, p. 37-43 (2003).

For example, compounds of Formula (1) can exhibit a ketamine oral bioavailability (% F) of at least 10%, at least 20%, at least 30%, at least 40%, at least 50%, or at least 60%. Compounds of Formula (1) can provide a ketamine oral availability, for example, from 5% to 90% from, 10% to 80%, from 15% to 70%, or from 20% to 60%.

Pharmaceutical compositions provided by the present disclosure may further comprise one or more pharmaceutically active compounds in addition to a compound of Formula (1). Such compounds may be provided to treat the disease being treated with the compound of Formula (1) or to treat a disease, disorder, or condition other than that being treated with the compound of Formula (1).

A compound of Formula (1) may be used in combination with at least one other therapeutic agent. A compound of Formula (1) may be administered to a patient together with another compound for treating a bacterial infection in the patient. The at least one other therapeutic agent may be a different compound encompassed by Formula (1). A compound of Formula (1) and the at least one other therapeutic agent may act additively or synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating a different disease, disorder or condition other than the disease being treated with ketamine. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a patient. A pharmaceutical composition comprising a compound of Formula (1) may be co-administered with an active agent having pharmacological effects that enhances the therapeutic efficacy of the compound of Formula (1).

ASPECTS OF THE INVENTION

The invention is further defined by the following aspects.
Aspect 1. A compound of Formula (1):

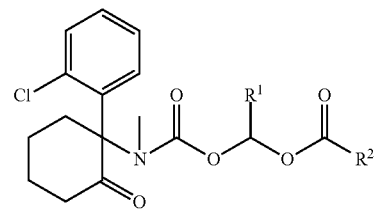

or a pharmaceutically acceptable salt thereof, wherein,
$R^1$ is selected from hydrogen and $C_{1-6}$ alkyl; and
$R^2$ is selected from a moiety of Formula (2), a moiety of Formula (3), a moiety of Formula (4), and a moiety of Formula (5):

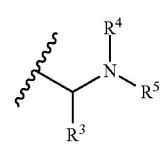

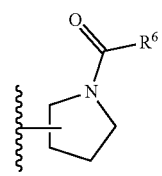

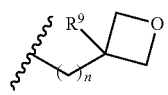

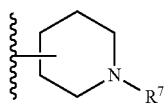

wherein,
$R^3$ is selected from hydrogen, $C_{1-6}$ alkyl, $C_{7-12}$ alkylarene, and substituted $C_{7-12}$ alkylarene;
$R^4$ is selected from hydrogen and $C_{1-6}$ alkyl;
$R^5$ is selected from hydrogen, $C_{1-6}$ alkyl, —C(=O)—$R^{10}$, and —C(=O)—O—$R^{10}$, wherein $R^{10}$ is selected from $C_{1-6}$ alkyl, $C_{3-6}$ cycloalkyl, and —$CF_3$;
$R^6$ is selected from $C_{1-6}$ alkyl and $C_{1-6}$ alkoxy;
n is an integer from 0 to 3;
$R^7$ is selected from hydrogen, $C_{1-6}$ alkyl, —C(=O)—$R^{11}$, and —C(=O)—O—$R^{10}$, wherein,
$R^{10}$ is selected from $C_{1-6}$ alkyl and $C_{3-6}$ cycloalkyl; and
$R^{11}$ is selected from —$NH_2$, —$CF_3$, $C_{1-6}$ alkyl, and $C_{3-6}$ cycloalkyl; and
$R^9$ is selected from hydrogen and $C_{1-3}$ alkyl.

Aspect 2. The compound of aspect 1, wherein the carbon atom to which $R^1$ is bonded is in the (S) configuration.

Aspect 3. The compound of aspect 1, wherein the carbon atom to which $R^1$ is bonded is in the (R) configuration.

Aspect 4. The compound of any one of aspects 1 to 3, wherein $R^1$ is hydrogen.

Aspect 5. The compound of any one of aspects 1 to 3, wherein $R^1$ is $C_{1-6}$ alkyl.

Aspect 6. The compound of any one of aspects 1 to 3, wherein $R^1$ is selected from methyl, ethyl, propyl, and isopropyl.

Aspect 7. The compound of any one of aspects 1 to 6, wherein $R^2$ is a moiety of Formula (2):

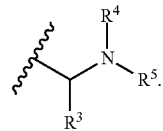
(2)

Aspect 8. The compound of aspect 7, wherein $R^3$ is hydrogen.

Aspect 9. The compound of aspect 7, wherein $R^3$ is $C_{1-6}$ alkyl.

Aspect 10. The compound of aspect 7, wherein $R^3$ is selected from methyl, ethyl, isopropyl, isobutyl, and sec-isobutyl.

Aspect 11. The compound of aspect 7, wherein $R^3$ is $C_{7-12}$ alkylarene.

Aspect 12. The compound of aspect 7, wherein $R^3$ is selected from benzyl, 4-methylphenol, and 3-methyl-2H-indole.

Aspect 13. The compound of any one of aspects 7 to 12, wherein the carbon atom to which $R^3$ is bonded is in the (S) configuration.

Aspect 14. The compound of any one of aspects 7 to 12, wherein the carbon atom to which $R^3$ is bonded is in the (R) configuration.

Aspect 15. The compound of any one of aspects 7 to 14, wherein $R^4$ is hydrogen.

Aspect 16. The compound of any one of aspects 7 to 14, wherein $R^4$ is $C_{1-6}$ alkyl.

Aspect 17. The compound of any one of aspects 7 to 14, wherein $R^4$ is $C_{1-4}$ alkyl.

Aspect 18. The compound of any one of aspects 7 to 14, wherein $R^4$ is selected from methyl, ethyl, propyl and isopropyl.

Aspect 19. The compound of any one of aspects 7 to 18, wherein $R^5$ is $C_{1-4}$ alkyl.

Aspect 20. The compound of any one of aspects 7 to 18, wherein $R^5$ is selected from methyl, ethyl, propyl, and isopropyl.

Aspect 21. The compound of any one of aspects 7 to 18, wherein $R^5$ is $-C(=O)-R^{10}$.

Aspect 22. The compound of aspect 21, wherein $R^{10}$ is $-NH_2$.

Aspect 23. The compound of aspect 21, wherein $R^{10}$ is $C_{1-6}$ alkyl.

Aspect 24. The compound of aspect 21, wherein $R^{10}$ is selected from methyl, ethyl, propyl, and isopropyl.

Aspect 25. The compound of aspect 21, wherein $R^{10}$ is $C_{3-6}$ cycloalkyl.

Aspect 26. The compound of aspect 21, wherein $R^{10}$ is $-CF_3$.

Aspect 27. The compound of any one of aspects 7 to 18, wherein $R^5$ is $-C(=O)-O-R^{10}$.

Aspect 28. The compound of aspect 27, wherein $R^{10}$ is $C_{1-6}$ alkyl.

Aspect 29. The compound of aspect 27, wherein $R^{10}$ is $C_{3-6}$ cycloalkyl.

Aspect 30. The compound of any one of aspects 1 to 6, wherein $R^2$ is a moiety of Formula (3):

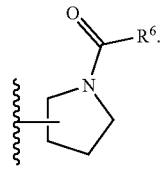
(3)

Aspect 31. The compound of aspect 30, wherein $R^6$ is selected from $C_{1-6}$ alkyl.

Aspect 32. The compound of aspect 30, wherein $R^6$ is selected from methyl, ethyl, propyl, and isopropyl.

Aspect 33. The compound of aspect 30, wherein $R^6$ is selected from $C_{1-6}$ alkoxy.

Aspect 34. The compound of aspect 30, wherein $R^6$ is selected from methoxy, ethoxy, n-propoxy, and isopropoxy.

Aspect 35. The compound of any one of aspects 1 to 6, wherein the moiety of Formula (3) has the structure of Formula (3a):

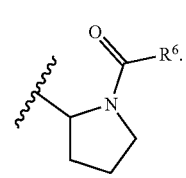
(3a)

Aspect 36. The compound of any one of aspects 1 to 6, wherein $R^2$ is a moiety of Formula (4):

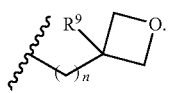
(4)

Aspect 37. The compound of aspect 36, wherein n is 0.
Aspect 38. The compound of aspect 36, wherein n is 1.
Aspect 39. The compound of aspect 36, wherein n is 2.
Aspect 40. The compound of any one of aspects 36 to 39, wherein $R^9$ is hydrogen.
Aspect 41. The compound of any one of aspects 36 to 39, wherein $R^9$ is selected from methyl, ethyl propyl, and isopropyl.
Aspect 42. The compound of any one of aspects 1 to 6, wherein $R^2$ is a moiety of Formula (5):

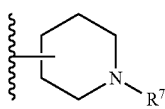
(5)

Aspect 43. The compound of aspect 42, wherein $R^7$ is hydrogen.
Aspect 44. The compound of aspect 42, wherein $R^7$ is $C_{1-6}$ alkyl.
Aspect 45. The compound of aspect 42, wherein $R^7$ is selected from methyl, ethyl, propyl, and isopropyl.
Aspect 46. The compound of aspect 42, wherein $R^7$ is $-C(=O)-R^{11}$.

Aspect 47. The compound of aspect 46, wherein $R^{11}$ is —$NH_2$.

Aspect 48. The compound of aspect 46, wherein $R^{11}$ is $C_{1-6}$ alkyl.

Aspect 49. The compound of aspect 46, wherein $R^{11}$ is $C_{3-6}$ cycloalkyl.

Aspect 50. The compound of aspect 42, wherein $R^7$ is —C(=O)—O—$R^{10}$.

Aspect 51. The compound of aspect 50, wherein $R^1$ is $C_{1-6}$ alkyl.

Aspect 52. The compound of aspect 50, wherein $R^1$ is $C_{3-6}$ cycloalkyl.

Aspect 53. The compound of aspect 42, wherein the moiety of Formula (5) is 1-substituted-4-methylpiperidine.

Aspect 54. The compound of any one of aspects 1 to 53, wherein the compound is the (R)-isomer having the structure of Formula (1a):

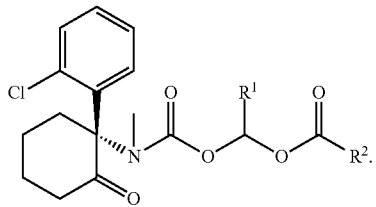

(1a)

Aspect 55. The compound of any one of aspects 1 to 53, wherein the compound is the (S)-isomer having the structure of Formula (1b):

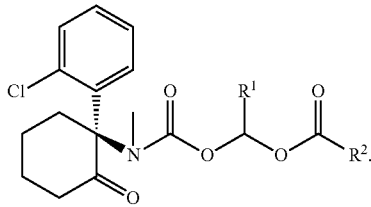

(1b)

Aspect 56. The compound of any one of aspects 1 to 53, wherein the compound comprises a hydrochloride salt.

Aspect 57. The compound of aspect 1, wherein the compound is selected from:

1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl (tert-butoxycarbonyl)glycinate (4);
1-((((S)-1-(2-chlorophenyl)-2-oxocyclohexyl)(methyl)carbamoyl)oxy)ethyl (tert-butoxycarbonyl)-L-valinate (5);
1-((((S)-1-(2-chlorophenyl)-2-oxocyclohexyl)(methyl)carbamoyl)oxy)ethyl 2-(3-methyloxetan-3-yl)acetate (6);
1-((((S)-1-(2-chlorophenyl)-2-oxocyclohexyl)(methyl)carbamoyl)oxy)ethyl acetyl-L-alaninate (7);
1-((((S)-1-(2-chlorophenyl)-2-oxocyclohexyl)(methyl)carbamoyl)oxy)ethyl acetyl-L-valinate (8);
1-((((S)-1-(2-chlorophenyl)-2-oxocyclohexyl)(methyl)carbamoyl)oxy)ethyl 1-methylpiperidine-4-carboxylate (17);
1-((((S)-1-(2-chlorophenyl)-2-oxocyclohexyl)(methyl)carbamoyl)oxy)ethyl isobutyrylglycinate (19);
(S)-(((1-(2-chlorophenyl)-2-oxocyclohexyl)(methyl)carbamoyl)oxy)methyl 2-(3-methyloxetan-3-yl)acetate (22);
1-((((S)-1-(2-chlorophenyl)-2-oxocyclohexyl)(methyl)carbamoyl)oxy)propyl 2-(3-methyloxetan-3-yl)acetate (24);
1-((((S)-1-(2-chlorophenyl)-2-oxocyclohexyl)(methyl)carbamoyl)oxy)-2-methylpropyl 2-(3-methyloxetan-3-yl)acetate (26);
1-((((S)-1-(2-chlorophenyl)-2-oxocyclohexyl)(methyl)carbamoyl)oxy)propyl acetylglycinate (27);
1-((((S)-1-(2-chlorophenyl)-2-oxocyclohexyl)(methyl)carbamoyl)oxy)-2-methylpropyl acetylglycinate (28);
(S)-(((1-(2-chlorophenyl)-2-oxocyclohexyl)(methyl)carbamoyl)oxy)methyl acetylglycinate (31);
((((S)-1-(2-chlorophenyl)-2-oxocyclohexyl)(methyl)carbamoyl)oxy)methyl acetyl-L-valinate (32);
((((S)-1-(2-chlorophenyl)-2-oxocyclohexyl)(methyl)carbamoyl)oxy)methyl acetyl-L-alaninate (33);
(S)-(((1-(2-chlorophenyl)-2-oxocyclohexyl)(methyl)carbamoyl)oxy)methyl isobutyrylglycinate (34);
((((S)-1-(2-chlorophenyl)-2-oxocyclohexyl)(methyl)carbamoyl)oxy)methyl isobutyryl-L-alaninate (35);
((((S)-1-(2-chlorophenyl)-2-oxocyclohexyl)(methyl)carbamoyl)oxy)methyl isobutyryl-L-valinate (36);
((((S)-1-(2-chlorophenyl)-2-oxocyclohexyl)(methyl)carbamoyl)oxy)methyl L-valinate (37);
(S)-(((1-(2-chlorophenyl)-2-oxocyclohexyl)(methyl)carbamoyl)oxy)methyl glycinate (38);
((((S)-1-(2-chlorophenyl)-2-oxocyclohexyl)(methyl)carbamoyl)oxy)methyl dimethyl-L-valinate (39);
(S)-(((1-(2-chlorophenyl)-2-oxocyclohexyl)(methyl)carbamoyl)oxy)methyl N-acetyl-N-methylglycinate (40);
1-((((S)-1-(2-chlorophenyl)-2-oxocyclohexyl)(methyl)carbamoyl)oxy)ethyl N-acetyl-N-methylglycinate (41);
1-((((S)-1-(2-chlorophenyl)-2-oxocyclohexyl)(methyl)carbamoyl)oxy)ethyl propionylglycinate (42);
(S)-(((1-(2-chlorophenyl)-2-oxocyclohexyl)(methyl)carbamoyl)oxy)methyl propionylglycinate (43);
((((S)-1-(2-chlorophenyl)-2-oxocyclohexyl)(methyl)carbamoyl)oxy)methyl L-alaninate (44);
1-((((S)-1-(2-chlorophenyl)-2-oxocyclohexyl)(methyl)carbamoyl)oxy)ethyl (2,2,2-trifluoroacetyl)glycinate (45);
(S)-(((1-(2-chlorophenyl)-2-oxocyclohexyl)(methyl)carbamoyl)oxy)methyl (2,2,2-trifluoroacetyl)glycinate (46);
1-((((S)-1-(2-chlorophenyl)-2-oxocyclohexyl)(methyl)carbamoyl)oxy)ethyl dimethyl-L-alaninate (47);
((((S)-1-(2-chlorophenyl)-2-oxocyclohexyl)(methyl)carbamoyl)oxy)methyl (2,2,2-trifluoroacetyl)-L-valinate (48);
1-((((S)-1-(2-chlorophenyl)-2-oxocyclohexyl)(methyl)carbamoyl)oxy)propyl (2,2,2-trifluoroacetyl)glycinate (49);
((((S)-1-(2-chlorophenyl)-2-oxocyclohexyl)(methyl)carbamoyl)oxy)methyl (2,2,2-trifluoroacetyl)-L-alaninate (50);
1-((((S)-1-(2-chlorophenyl)-2-oxocyclohexyl)(methyl)carbamoyl)oxy)-2-methylpropyl (2,2,2-trifluoroacetyl)glycinate (51);
1-((((S)-1-(2-chlorophenyl)-2-oxocyclohexyl)(methyl)carbamoyl)oxy)ethyl (2,2,2-trifluoroacetyl)-L-valinate (52);
1-((((S)-1-(2-chlorophenyl)-2-oxocyclohexyl)(methyl)carbamoyl)oxy)ethyl (2,2,2-trifluoroacetyl)-L-alaninate (53);
1-((((S)-1-(2-chlorophenyl)-2-oxocyclohexyl)(methyl)carbamoyl)oxy)ethyl acetyl-L-leucinate (57);
((((S)-1-(2-chlorophenyl)-2-oxocyclohexyl)(methyl)carbamoyl)oxy)methyl acetyl-L-leucinate (58);
1-((((S)-1-(2-chlorophenyl)-2-oxocyclohexyl)(methyl)carbamoyl)oxy)ethyl acetyl-L-alloisoleucinate (59);
((((S)-1-(2-chlorophenyl)-2-oxocyclohexyl)(methyl)carbamoyl)oxy)methyl acetyl-L-alloisoleucinate (60);

1-((((R)-1-(2-chlorophenyl)-2-oxocyclohexyl)(methyl)carbamoyl)oxy)ethyl acetylglycinate (62);
1-((((R)-1-(2-chlorophenyl)-2-oxocyclohexyl)(methyl)carbamoyl)oxy)ethyl 2-(3-methyloxetan-3-yl)acetate (63);
1-((((R)-1-(2-chlorophenyl)-2-oxocyclohexyl)(methyl)carbamoyl)oxy)ethyl acetyl-L-alaninate (64);
1-((((R)-1-(2-chlorophenyl)-2-oxocyclohexyl)(methyl)carbamoyl)oxy)ethyl acetyl-L-valinate (65);
(R)-(((1-(2-chlorophenyl)-2-oxocyclohexyl)(methyl)carbamoyl)oxy)methyl 2-(3-methyloxetan-3-yl)acetate (66);
(((1-(2-chlorophenyl)-2-oxocyclohexyl)(methyl)carbamoyl)oxy)methyl acetylglycinate (68);
(((1-(2-chlorophenyl)-2-oxocyclohexyl)(methyl)carbamoyl)oxy)methyl acetyl-L-valinate (69);
(((1-(2-chlorophenyl)-2-oxocyclohexyl)(methyl)carbamoyl)oxy)methyl acetyl-L-alaninate (70);
((((R)-1-(2-chlorophenyl)-2-oxocyclohexyl)(methyl)carbamoyl)oxy)methyl acetyl-L-leucinate (71);
(((1-(2-chlorophenyl)-2-oxocyclohexyl)(methyl)carbamoyl)oxy)methyl acetyl-L-alloisoleucinate (72);
((((S)-1-(2-chlorophenyl)-2-oxocyclohexyl)(methyl)carbamoyl)oxy)methyl dimethyl-L-lloisoleucinate hydrogen chloride (74);
((((S)-1-(2-chlorophenyl)-2-oxocyclohexyl)(methyl)carbamoyl)oxy)methyl methyl-L-valinate hydrogen chloride (75);
((((S)-1-(2-chlorophenyl)-2-oxocyclohexyl)(methyl)carbamoyl)oxy)methyl dimethyl-L-leucinate hydrogen chloride (76);
((((S)-1-(2-chlorophenyl)-2-oxocyclohexyl)(methyl)carbamoyl)oxy)methyl diethyl-L-valinate hydrogen chloride (77);
((((S)-1-(2-chlorophenyl)-2-oxocyclohexyl)(methyl)carbamoyl)oxy)methyl methyl-L-alaninate 2,2,2-trifluoroacetic acid (78);
((((S)-1-(2-chlorophenyl)-2-oxocyclohexyl)(methyl)carbamoyl)oxy)methyl dipropyl-L-valinate (79);
((((S)-1-(2-chlorophenyl)-2-oxocyclohexyl)(methyl)carbamoyl)oxy)methyl L-leucinate hydrogen chloride (80);
((((S)-1-(2-chlorophenyl)-2-oxocyclohexyl)(methyl)carbamoyl)oxy)methyl isopropyl-L-valinate hydrogen chloride (81);
((((S)-1-(2-chlorophenyl)-2-oxocyclohexyl)(methyl)carbamoyl)oxy)methyl propyl-L-valinate hydrogen chloride (82);
((((S)-1-(2-chlorophenyl)-2-oxocyclohexyl)(methyl)carbamoyl)oxy)methyl ethyl-L-valinate (83);
(piperidine-4-carboxyloyloxy)methyl (S)-1-(2-chlorophenyl)-2-oxocyclohexylmethylcarbamate (86);
((((S)-1-(2-chlorophenyl)-2-oxocyclohexyl)(methyl)carbamoyl)oxy)methyl acetyl-D-prolinate (87);
((((S)-1-(2-chlorophenyl)-2-oxocyclohexyl)(methyl)carbamoyl)oxy)methyl acetyl-L-phenylalaninate (88);
((((S)-1-(2-chlorophenyl)-2-oxocyclohexyl)(methyl)carbamoyl)oxy)methyl acetyl-L-tyrosinate (89);
1-((((S)-1-(2-chlorophenyl)-2-oxocyclohexyl)(methyl)carbamoyl)oxy)ethyl dimethyl-L-valinate (90); and
a pharmaceutically acceptable salt of any of the foregoing.

Aspect 58. The compound of aspect 1, wherein the compound is selected from:
1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl 2-(3-methyloxetan-3-yl)acetate (6);
1-((((S)-1-(2-chlorophenyl)-2-oxocyclohexyl)(methyl)carbamoyl)oxy)ethyl acetyl-L-alaninate (7);
1-((((S)-1-(2-chlorophenyl)-2-oxocyclohexyl)(methyl)carbamoyl)oxy)ethyl isonicotinate (18);
1-((((S)-1-(2-chlorophenyl)-2-oxocyclohexyl)(methyl)carbamoyl)oxy)ethyl isobutyrylglycinate (19);
(S)-(((1-(2-chlorophenyl)-2-oxocyclohexyl)(methyl)carbamoyl)oxy)methyl 2-(3-methyloxetan-3-yl)acetate (22);
1-((((S)-1-(2-chlorophenyl)-2-oxocyclohexyl)(methyl)carbamoyl)oxy)propyl acetylglycinate (27);
1-((((S)-1-(2-chlorophenyl)-2-oxocyclohexyl)(methyl)carbamoyl)oxy)-2-methylpropyl acetylglycinate (28);
((((S)-1-(2-chlorophenyl)-2-oxocyclohexyl)(methyl)carbamoyl)oxy)methyl dimethyl-L-valinate (39);
((((S)-1-(2-chlorophenyl)-2-oxocyclohexyl)(methyl)carbamoyl)oxy)methyl acetyl-L-(60); and
a pharmaceutically acceptable salt of any of the foregoing.

Aspect 59. A compound of Formula (1):

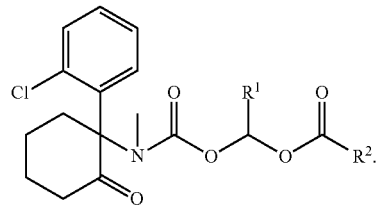

or a pharmaceutically acceptable salt thereof, wherein,
R$^1$ is selected from hydrogen and C$_{1-6}$ alkyl; and
R$^2$ is a moiety of Formula (6):

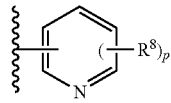

wherein
p is an integer from 1 to 3; and
each R$^8$ is independently selected from C$_{1-6}$ alkyl and —NH$_2$.

Aspect 60. The compound of aspect 59, wherein the carbon atom to which R$^1$ is bonded is in the (S) configuration.

Aspect 61. The compound of aspect 59, wherein the carbon atom to which R$^1$ is bonded is in the (R) configuration.

Aspect 62. The compound of any one of aspects 59 to 61, wherein R$^1$ is hydrogen.

Aspect 63. The compound of any one of aspects 59 to 61, wherein R$^1$ is C$_{1-6}$ alkyl.

Aspect 64. The compound of any one of aspects 59 to 61, wherein R$^1$ is selected from methyl, ethyl, propyl, and isopropyl.

Aspect 65. The compound of any one of aspects 59 to 64, wherein p is 1.

Aspect 66. The compound of any one of aspects 59 to 64, wherein p is 2.

Aspect 67. The compound of any one of aspects 59 to 66, wherein each R is interpedently selected from C$_{1-6}$ alkyl.

Aspect 68. The compound of any one of aspects 59 to 66, wherein each R is independently selected from methyl, ethyl, propyl, and isopropyl.

Aspect 69. The compound of any one of aspects 59 to 66, wherein R$^8$ is —NH$_2$.

Aspect 70. The compound of aspect 59, wherein the compound is selected from:
1-((((S)-1-(2-chlorophenyl)-2-oxocyclohexyl)(methyl)carbamoyl)oxy)ethyl nicotinate (14);
1-((((S)-1-(2-chlorophenyl)-2-oxocyclohexyl)(methyl)carbamoyl)oxy)ethyl isonicotinate 4 (18);
(S)-(((1-(2-chlorophenyl)-2-oxocyclohexyl)(methyl)carbamoyl)oxy)methyl nicotinate (29);
(S)-(((1-(2-chlorophenyl)-2-oxocyclohexyl)(methyl)carbamoyl)oxy)methyl 4-methylnicotinate (54);
(S)-(((1-(2-chlorophenyl)-2-oxocyclohexyl)(methyl)carbamoyl)oxy)methyl 2-methylnicotinate (55);
(S)-(((1-(2-chlorophenyl)-2-oxocyclohexyl)(methyl)carbamoyl)oxy)methyl 6-methylnicotinate (56);
(S)-(((1-(2-chlorophenyl)-2-oxocyclohexyl)(methyl)carbamoyl)oxy)methyl 2-aminonicotinate (61);
(R)-(((1-(2-chlorophenyl)-2-oxocyclohexyl)(methyl)carbamoyl)oxy)methyl nicotinate (67);
(R)-(((1-(2-chlorophenyl)-2-oxocyclohexyl)(methyl)carbamoyl)oxy)methyl 2-aminonicotinate (73); and
a pharmaceutically acceptable salt of any of the foregoing.

Aspect 71. The compound of any one of aspects 59 to 70, wherein the compound is the (R)-isomer having the structure of Formula (1a):

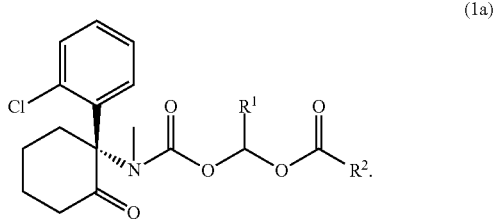

(1a)

Aspect 72. The compound of any one of aspects 59 to 71, wherein the compound is the (S)-isomer having the structure of Formula (1b):

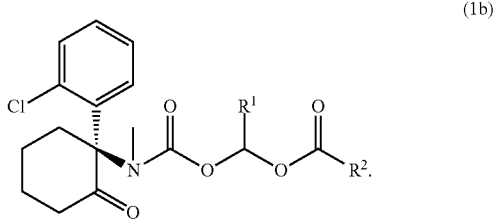

(1b)

Aspect 73. The compound of any one of aspects 59 to 72, wherein the compound comprises a hydrochloride salt.

Aspect 74. The compound of aspect 1, wherein,
$R^1$ is selected from hydrogen and methyl;
$R^2$ is a moiety of Formula (2);
$R^3$ is selected from hydrogen and $C_{1-4}$ alkyl;
$R^4$ is selected from hydrogen and $C_{1-3}$ alkyl; and
$R^5$ is selected from $C_{1-3}$ alkyl and —C(=O)—$R^{10}$, where $R^{10}$ is selected from $C_{1-3}$ alkyl.

Aspect 75. The compound of aspect 74, wherein $R^1$ is hydrogen.

Aspect 76. The compound of aspect 74, wherein $R^1$ is methyl.

Aspect 77. The compound of any one of aspects 74 to 76, wherein the carbon atom to which $R^1$ is bonded is in the (S) configuration.

Aspect 78. The compound of any one of aspects 74 to 76, wherein the carbon atom to which $R^1$ is bonded is in the (R) configuration.

Aspect 79. The compound of any one of aspects 74 to 78, wherein $R^3$ is hydrogen.

Aspect 80. The compound of any one of aspects 74 to 78, wherein $R^3$ is $C_{1-3}$ alkyl.

Aspect 81. The compound of any one of aspects 74 to 80, wherein the carbon atom to which $R^3$ is bonded is in the (S) configuration.

Aspect 82. The compound of any one of aspects 74 to 80, wherein the carbon atom to which $R^3$ is bonded is in the (R) configuration.

Aspect 83. The compound of any one of aspects 74 to 82, wherein $R^4$ is hydrogen.

Aspect 84. The compound of any one of aspects 74 to 82, wherein $R^4$ is $C_{1-3}$ alkyl.

Aspect 85. The compound of any one of aspects 74 to 84, wherein $R^5$ is $C_{1-3}$ alkyl.

Aspect 86. The compound of any one of aspects 74 to 84, wherein $R^5$ is —C(=O)—$R^{10}$.

Aspect 87. The compound of aspect 1, wherein,
$R^1$ is selected from hydrogen and methyl;
$R^2$ is a moiety of Formula (4);
n is 1; and
$R^9$ is selected from $C_{1-3}$ alkyl.

Aspect 88. The compound of aspect 87, wherein $R^1$ is hydrogen.

Aspect 89. The compound of aspect 87, wherein $R^1$ is methyl.

Aspect 90. The compound of any one of aspects 87 to 89, wherein the carbon atom to which $R^1$ is bonded is in the (S) configuration.

Aspect 91. The compound of any one of aspects 87 to 89, wherein the carbon atom to which $R^1$ is bonded is in the (R) configuration.

Aspect 92. The compound of any one of aspects 87 to 91, wherein $R^3$ is hydrogen.

Aspect 93. The compound of any one of aspects 87 to 91, wherein $R^3$ is methyl.

Aspect 94. The compound of aspect 1, wherein,
$R^1$ is selected from hydrogen and methyl;
$R^2$ is a moiety of Formula (5); and
$R^7$ is selected from $C_{1-3}$ alkyl.

Aspect 95. The compound of aspect 94, wherein $R^1$ is hydrogen.

Aspect 96. The compound of aspect 94, wherein $R^1$ is methyl.

Aspect 97. The compound of any one of aspects 94 to 96, wherein the carbon atom to which $R^1$ is bonded is in the (S) configuration.

Aspect 98. The compound of any one of aspects 94 to 96, wherein the carbon atom to which $R^1$ is bonded is in the (R) configuration.

Aspect 99. The compound of any one of aspects 94 to 98, wherein $R^7$ is methyl.

Aspect 100. The compound of aspect 59, wherein,
$R^1$ is selected from hydrogen and methyl;
$R^2$ is a moiety of Formula (6); and
$R^8$ is selected from —$NH_2$.

Aspect 101. The compound of aspect 100, wherein $R^1$ is hydrogen.

Aspect 102. The compound of aspect 100, wherein $R^1$ is methyl.

Aspect 103. The compound of any one of aspects 100 to 102, wherein the carbon atom to which $R^1$ is bonded is in the (S) configuration.

Aspect 104. The compound of any one of aspects 100 to 102, wherein the carbon atom to which R¹ is bonded is in the (R) configuration.

Aspect 105. A pharmaceutical composition comprising the compound of any one of aspects 1 to 104 or a pharmaceutically acceptable salt thereof.

Aspect 106. The pharmaceutical composition of aspect 105, wherein the pharmaceutical composition comprises an oral dosage formulation.

Aspect 107. The pharmaceutical composition of any one of aspects 105 to 106, wherein the pharmaceutical composition comprises an oral dosage form.

Aspect 108. The pharmaceutical composition of aspect 107, wherein the oral dosage form comprises a controlled release oral dosage form, a sustained release oral dosage form, or a combination thereof.

Aspect 109. The pharmaceutical composition of any one of aspects 107 to 108, wherein the oral dosage form comprises a therapeutically effective amount of the compound of any one of aspects 1 to 104 for treating a neurological disease of the central nervous system of a patient, a psychiatric disease of a patient, or pain of a patient.

Aspect 110. The pharmaceutical composition of any one of aspects 107 to 109, wherein the oral dosage form comprises a therapeutically effective amount of the compound of any one of aspects 1 to 104 for treating depression of a patient.

Aspect 111. A method of providing a therapeutically effective amount of a ketamine in the systemic circulation of a patent comprising administering to the patient in need thereof, the compound of any one of aspects 1 to 104 or a pharmaceutically acceptable salt thereof.

Aspect 112. The method of aspect 111, wherein administering comprises orally administering.

Aspect 113. A method of treating a disease in a patient, wherein the disease is known to be treated by administering ketamine, comprising administering to a patient in need thereof, a pharmaceutically acceptable amount of the compound of any one of aspects 1 to 104 or a pharmaceutically acceptable salt thereof.

Aspect 114. The method of aspect 113, wherein the disease is a neurological disease of the central nervous system.

Aspect 115. The method of aspect 113, wherein the disease is a psychiatric disease.

Aspect 116. The method of aspect 113, wherein the psychiatric disease is depression.

Aspect 117. The method of aspect 113, wherein the psychiatric disease is pain.

Aspect 118. The method of any one of aspects 113 to 117, wherein administering comprises orally administering.

Aspect 119. The method of any one of aspects 113 to 118, wherein administering comprises administering an oral dosage form.

Aspect 120. The method of aspect 119, wherein the oral dosage form comprises a controlled release oral dosage form, a sustained release oral dosage form, or a combination thereof.

Aspect 121. The method of any one of aspects 113 to 120, wherein the method further comprises administering to the patient at least one additional therapeutic agent for treating the disease.

Aspect 122. The method of any one of aspects 113 to 121, wherein, following administration, the compound provides a therapeutically effective amount of (R)-ketamine, (S)-ketamine, a metabolite of any of the foregoing, or a combination of any of the foregoing in the systemic circulation of the patient for treating the disease.

Aspect 123. A method of treating a disease in a patient, wherein the disease is known to be treated by administering ketamine, comprising administering to a patient in need thereof, a pharmaceutically acceptable amount of the pharmaceutical composition of any one of aspects 105 to 110.

Aspect 124. The method of aspect 123, wherein the disease is a neurological disease of the central nervous system.

Aspect 125. The method of aspect 123, wherein the disease is a psychiatric disease.

Aspect 126. The method of aspect 123, wherein the psychiatric disease is depression.

Aspect 127. The method of aspect 123, wherein the psychiatric disease is pain.

Aspect 128. The method of any one of aspects 123 to 127, wherein administering comprises orally administering.

Aspect 129. The method of any one of aspects 123 to 128, wherein administering comprises administering an oral dosage form.

Aspect 130. The method of aspect 129, wherein the oral dosage form comprises a controlled release oral dosage form, a sustained release oral dosage form, or a combination thereof.

Aspect 131. The method of any one of aspects 123 to 130, wherein the method further comprises administering to the patient at least one additional therapeutic agent for treating the disease.

Aspect 132. The method of any one of aspects 123 to 131, wherein, following administration, the pharmaceutical composition provides a therapeutically effective amount of (R)-ketamine, (S)-ketamine, a metabolite of any of the foregoing, or a combination of any of the foregoing in the systemic circulation of the patient for treating the disease.

EXAMPLES

The following examples describe in detail the synthesis of compounds of Formula (1), the characterization of compounds of Formula (1), and uses of compounds of Formula (1). It will be apparent to those skilled in the art that many modifications, both to materials and methods, may be practiced without departing from the scope of the disclosure.

Example 1

Synthesis of 1-((((S)-1-(2-chlorophenyl)-2-oxocyclohexyl)(methyl)carbamoyl)oxy)ethyl 3-hydroxy-2-(hydroxymethyl)-2-methylpropanoate (1)

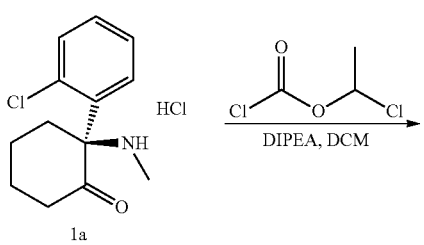

37

-continued

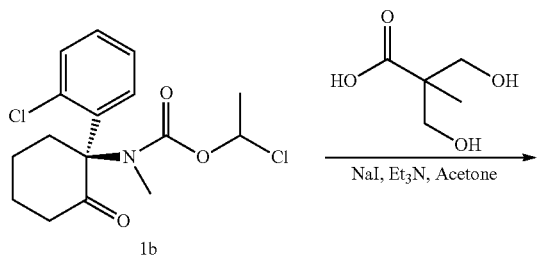

To a solution of S-ketamine hydrochloride 1a (274 mg, 1.0 mmol) and N,N-disisopropylethylamine (DIPEA) (260 mg, 1.0 mmol) in DCM (10 mL) was added 1-chloroethyl carbonochloridate (172 mg, 1.2 mmol) slowly at 0° C. The reaction was stirred at 25° C. for 1.5 h. The reaction was diluted with DCM (10 mL) and washed with water (10 mL) and brine (10 mL). The organic layer was dried over MgSO$_4$, filtered and concentrated to provide an oil, which was purified on silica gel column eluting with Hexane/EA (1/1 to 5/1) to afford 276 mg (79% yield) of 1b as a white solid. $^1$H NMR (500 MHz, CDCl$_3$): δ 1.60-1.96 (m, 6H), 1.99-2.10 (m, 1H), 2.32-2.56 (m, 1H), 2.57-2.63 (m, 1H), 2.67-2.84 (m, 1H), 3.01 and 3.07 (two s, total 3H), 3.22-3.40 (m, 1H), 6.48-6.60 (m, 1H), 6.91-7.04 (m, 1H), 7.22-7.30 (m, 2H), 7.43-7.49 (m, 1H).

To a solution of 1b (150 mg, 0.44 mmol), NaI (65 mg, 0.44 mmol) and 3-hydroxy-2-(hydroxymethyl)-2-methyl-propanoic acid (292 mg, 2.18 mmol) in acetone (1.7 mL) was added triethylamine (0.31 mL, 2.18 mmol). The reaction was stirred at 25° C. for 5 h. The reaction was concentrated and re-dissolved in EA (20 mL), washed with H$_2$O (8 mL), NaHCO$_{3(sat)}$ (2 mL) and brine (5 mL). The organic layer was dried over MgSO$_4$, filtered and concentrated to provide an oil, which was purified on silica gel column eluting with Hexane/EA (1/0 to 4/6) to afford 95 mg (49% yield) of the title compound the title compound 1 as a colorless oil. $^1$H NMR (DMSO-d$_6$, 500 MHz): δ 7.46 (m, 1H), 7.30 (m, 2H), 6.96 (d, J=7.1 Hz, 1H), 6.61 (q, J=5.4 Hz, 1H), 4.72 (m, 2H), 3.44-3.52 (m, 4H), 3.10-3.18 (m, 1H), 2.95 (d, J=9.0 Hz, 3H), 2.50-2.65 (m, 1H), 2.26-2.37 (m, 2H), 1.99 (bs, 1H), 1.68 (bs, 3H), 1.46 (bs, 3H), 1.02 (bs, 3H). LCMS (ESI): m/z calculated for [C$_{21}$H$_{28}$ClNO$_7$+H]$^+$ 442.16, found 442.20 [M+H]$^+$.

38

Example 2

Synthesis of 1-((((S)-1-(2-chlorophenyl)-2-oxocy-clohexyl)(methyl)carbamoyl)oxy)ethyl (2S)-5-oxopyrrolidine-2-carboxylate (2)

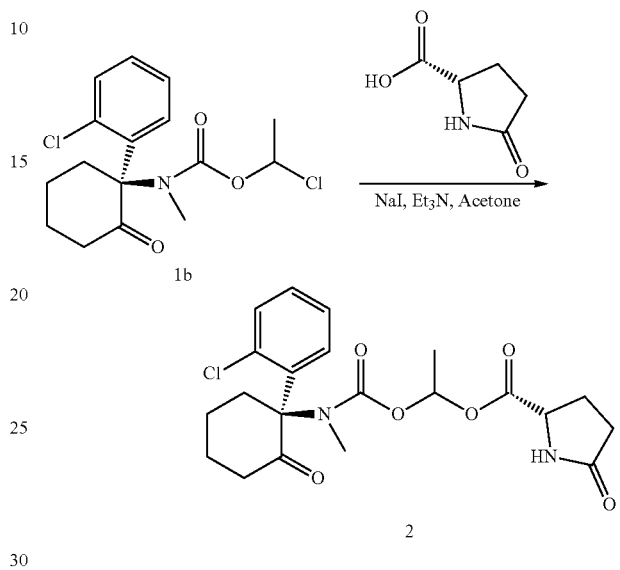

To a solution of 1b (100 mg, 0.29 mmol), NaI (43 mg, 0.29 mmol) and (S)-5-oxopyrrolidine-2-carboxylic acid (188 mg, 1.46 mmol) in acetone (1.2 mL) was added triethylamine (0.20 mL, 1.46 mmol). The reaction was stirred at 25° C. for 5 h and then concentrated. The mixture was diluted with EA (20 mL) and filtered. The filtrate was concentrated and then purified on silica gel column eluting with Hexane/EA (1/0 to 4/6) to afford 50 mg (39% yield) of the title compound 2 as a white foam. $^1$H NMR (CDCl$_3$, 500 MHz): δ 7.44 (m, 1H), 7.23-7.27 (m, 2H), 6.97 (bs, 1H), 6.73-6.79 (m, 1H), 6.22-6.57 (m, 1H), 4.19-4.25 (m, 1H), 3.29-3.33 (m, 1H), 3.02 (bs, 3H), 2.66-2.71 (m, 1H), 2.54-2.59 (m, 1H), 2.27-2.44 (m, 5H), 2.01 (m, 1H), 1.88 (bs, 1H), 1.73 (m, 2H), 1.48 (bs, 3H). LCMS (ESI): m/z calculated for [C$_{21}$H$_{25}$ClN$_2$O$_6$+H]$^+$ 437.14, found 437.21 [M+H]$^+$.

Example 3

Synthesis of 1-((((S)-1-(2-chlorophenyl)-2-oxocy-clohexyl)(methyl)carbamoyl)oxy)ethyl acetylglyci-nate

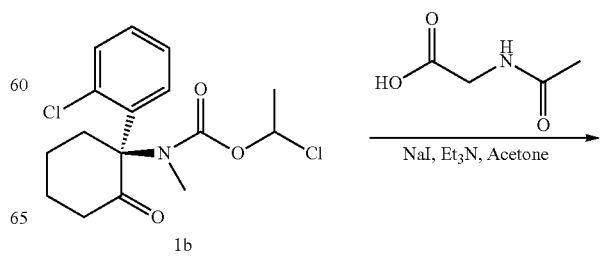

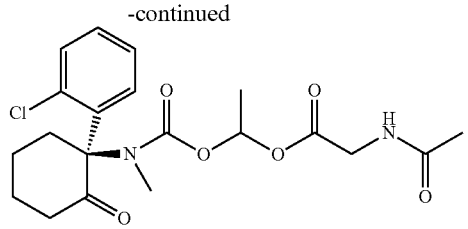

3

To a solution of 1b (172 mg, 0.5 mmol), NaI (75 mg, 0.5 mmol) and acetylglycine (176 mg, 1.5 mmol) in acetone (6 mL) was added triethylamine (0.35 mL, 2.5 mmol). The reaction was heated to 70° C. for 16 h. The reaction was concentrated and re-dissolved in DCM (10 mL), washed with NaHCO$_{3(sat)}$ (10 mL) and brine (10 mL). The organic layer was dried over MgSO$_4$, filtered and concentrated to provide an oil, which was purified on silica gel column eluting with Hexane/EA (1/0 to 1/2) to afford 110 mg (35% yield) of the title compound 3 as a white foam. $^1$H NMR (500 MHz, methanol-d$_4$): 1.51 (br, 3H), 1.77-1.83 (m, 3H), 2.01 (m, 3H), 2.05 (m, 1H), 2.33-2.46 (m, 2H), 2.67-2.82 (m, 1H), 3.03 and 3.05 (two s, total 3H), 3.36 (m, 1H), 3.87-3.97 (m, 2H), 6.76 (m, 1H), 7.04 (m, 1H), 7.30 (m, 2H), 7.45 (m, 1H). LCMS (ESI): m/z calculated for [C$_{20}$H$_{25}$ClN$_2$O$_6$+H]$^+$ 425.14, found 425.30 [M+H]$^+$.

Example 4

Synthesis of 1-((((S)-1-(2-chlorophenyl)-2-oxocyclohexyl)(methyl)carbamoyl)oxy)ethyl (tert-butoxycarbonyl)glycinate (4)

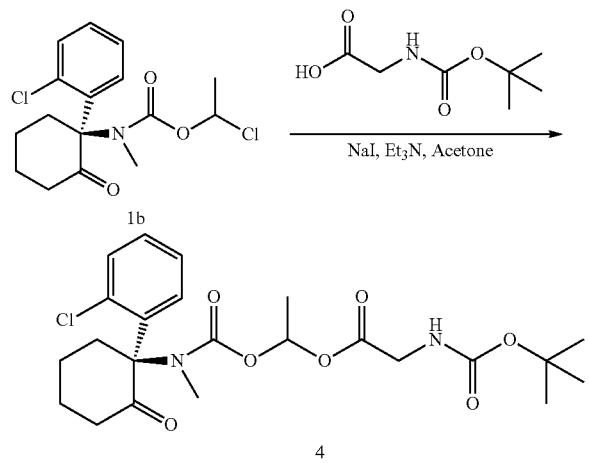

To a solution of 1b (86 mg, 0.25 mmol), NaI (37 mg, 0.25 mmol) and (tert-butoxycarbonyl)glycine (131 mg, 0.75 mmol) in acetone (1 mL) was added triethylamine (0.18 mL, 1.25 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 5/1) to afford 86 mg (71% yield) of the title compound 4 as a white foam. $^1$H NMR (500 MHz, CDCl$_3$): 1.46 (m, 12H), 1.76 (m, 2H), 1.89 (m, 1H), 2.06 (m, 1H), 2.36 (m, 1H), 2.56-2.60 (m, 1H), 2.71 (m, 1H), 3.00 and 3.05 (two s, total 3H), 3.83-3.99 (m, 2H), 5.04 (br, 1H), 6.79-6.84 (m, 1H), 6.98 (m, 1H), 7.25 (m, 2H), 7.45 (m, 1H). LCMS (ESI): m/z calculated for [C$_{23}$H$_{31}$ClN$_2$O$_7$+H]$^+$ 483.18, found 483.13 [M+H]$^+$.

Example 5

Synthesis of 1-((((S)-1-(2-chlorophenyl)-2-oxocyclohexyl)(methyl)carbamoyl)oxy)ethyl (tert-butoxycarbonyl)-L-valinate (5)

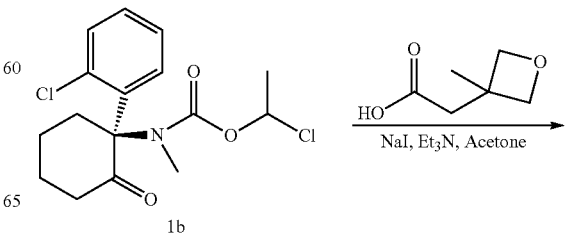

To a solution of 1b (86 mg, 0.25 mmol), NaI (37 mg, 0.25 mmol) and (tert-butoxycarbonyl)-L-valine (163 mg, 0.75 mmol) in acetone (1 mL) was added triethylamine (0.18 mL, 1.25 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 5/1) to afford 109 mg (83% yield) of the title compound 5 as a white foam. $^1$H NMR (500 MHz, CDCl$_3$): 0.78-0.93 (m, 6H), 1.43-1.44 (m, 11H), 1.72 (m, 3H), 1.87 (m, 1H), 2.03-2.09 (m, 1H), 2.36-2.39 (m, 1H), 2.56-2.59 (m, 1H), 2.64-2.74 (m, 1H), 2.98 and 3.00 (two s, total 3H), 3.25-3.35 (m, 1H), 4.20 (m, 1H), 5.00 (m, 1H), 6.80 (m, 1H), 6.96 (m, 1H), 7.23 (m, 2H), 7.42 (m, 1H). LCMS (ESI): m/z calculated for [C$_{26}$H$_{37}$ClN$_2$O$_7$+H]$^+$ 525.23, found 525.17 [M+H]$^+$.

Example 6

Synthesis of 1-((((S)-1-(2-chlorophenyl)-2-oxocyclohexyl)(methyl)carbamoyl)oxy)ethyl 2-(3-methyloxetan-3-yl)acetate (6)

-continued

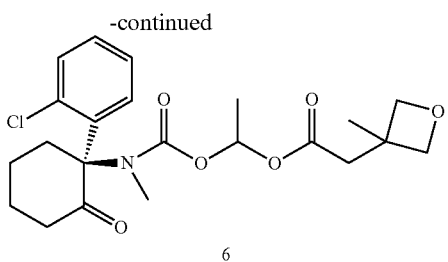

6

To a solution of 1b (262 mg, 0.76 mmol), NaI (114 mg, 0.76 mmol) and 2-(3-methyloxetan-3-yl)acetic acid (296 mg, 2.28 mmol) in acetone (9 mL) was added triethylamine (0.53 mL, 3.8 mmol). The reaction was heated to 70° C. for 3 h. The reaction was concentrated and redissolved in DCM (5 mL), washed with H$_2$O (5 mL) and brine (5 mL). The organic layer was dried over MgSO$_4$, filtered and concentrated to provide an oil, which was purified on silica gel column eluting with Hexane/EA (1/0 to 3/1) to afford a yellow oil. Ether (3 mL) was added, filtered and the solid was washed with cold ether to afford 102 mg (31% yield) of the title compound 6 as a white solid. $^1$H NMR (500 MHz, methanol-d$_4$): 1.38 (s, 3H), 1.48 (br, 3H), 1.76-1.84 (m, 3H), 2.05 (m, 1H), 2.36 (d, J=15.2 Hz, 1H), 2.46 (d, J=13.5 Hz, 1H), 2.70 (m, 1H), 2.73 (s, 2H), 3.04 (s, 3H), 3.36 (m, 1H), 4.36 (m, 2H), 4.59 (m, 2H), 6.70 (m, 1H), 7.07 (m, 1H), 7.29 (m, 2H), 7.45 (m, 1H). LCMS (ESI): m/z calculated for [C$_{22}$H$_{28}$ClNO$_6$+H]$^+$ 438.16, found 438.39 [M+H]$^+$.

The filtrate was concentrated to provide an oil and stored at −20° C. to get a sticky solid. The mixture was diluted with ether (2 mL) and collected the filtrate. The filtrate was concentrated to afford 40 mg (12% yield) of the 6 (S)-isomer as a colorless oil. $^1$H NMR (500 MHz, methanol-d$_4$): 1.32-1.40 (m, 3H), 1.49 (br, 3H), 1.72-1.92 (m, 3H), 2.05 (m, 1H), 2.41 (d, J=11.8 Hz, 1H), 2.49 (d, J=11.7 Hz, 1H), 2.63-2.74 (m, 2H), 2.75-2.84 (m, 1H), 3.03 (s, 3H), 3.36 (m, 1H), 4.36 (m, 2H), 4.59 (m, 2H), 6.73 (m, 1H), 7.04 (m, 1H), 7.30 (m, 2H), 7.46 (m, 1H).

Example 7

Synthesis of 1-((((S)-1-(2-chlorophenyl)-2-oxocyclohexyl)(methyl)carbamoyl)oxy)ethyl acetyl-L-alaninate (7)

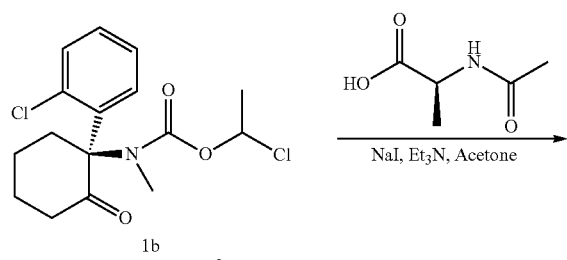

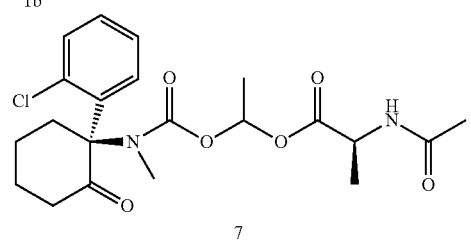

7

To a solution of 1b (172 mg, 0.5 mmol), NaI (150 mg, 1.0 mmol) and (S)-2-acetamidopropanoic acid (328 mg, 2.5 mmol) in acetone (6 mL) was added triethylamine (0.35 mL, 2.5 mmol). The reaction was heated to 70° C. for 16 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/1) to afford 149 mg (68% yield) of the title compound 7 as a white foam. $^1$H NMR (600 MHz, DMSO-d$_6$): δ 1.16-1.28 (m, 3H), 1.32-1.60 (m, 3H), 1.60-1.76 (m, 3H), 1.81-1.85 (m, 3H), 1.93-2.01 (m, 1H), 2.26-2.36 (m, 2H), 2.54-2.72 (m, 1H), 2.95 and 2.98 (two s, total 3H), 3.05-3.19 (m, 1H), 4.14-4.25 (m, 1H), 6.59-6.67 (m, 1H), 6.91-6.99 (m, 1H), 7.30-7.36 (m, 2H), 7.43-7.49 (m, 1H), 8.25-8.35 (m, 1H). LCMS (ESI): m/z calculated for [C$_{21}$H$_{27}$ClN$_2$O$_6$+H]$^+$ 439.16, found 439.29 [M+H]$^+$.

Example 8

Synthesis of 1-((((S)-1-(2-chlorophenyl)-2-oxocyclohexyl)(methyl)carbamoyl)oxy)ethyl acetyl-L-valinate (8)

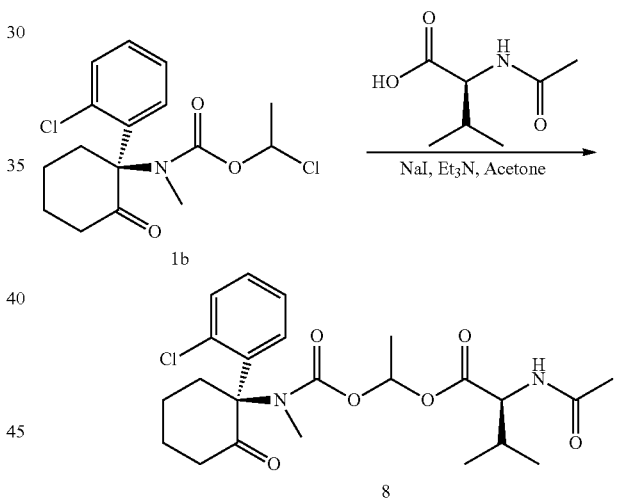

8

To a solution of 1b (172 mg, 0.5 mmol), NaI (150 mg, 1.0 mmol) and (S)-2-acetamido-3-methylbutanoic acid (239 mg, 1.5 mmol) in acetone (6 mL) was added triethylamine (0.35 mL, 2.5 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered concentrated to provide an oil, which was purified on silica gel column eluting with Hexane/EA (1/0 to 1/1) to afford 159 mg (68% yield) of the title compound 8 as a white foam. $^1$H NMR (500 MHz, DMSO-d$_6$): δ 0.70-0.95 (m, 6H), 1.30-1.55 (m, 3H), 1.60-1.79 (m, 3H), 1.88 (s, 3H), 1.90-2.08 (m, 1H), 2.22-2.41 (m, 2H), 2.55-2.70 (m, 1H), 2.95 and 2.97 (two s, total 3H), 3.05-3.20 (m, 2H), 4.10-4.25 (m, 1H), 6.55-6.78 (m, 1H), 6.92-7.05 (m, 1H), 7.25-7.43 (m, 2H), 7.45-7.55 (m, 1H), 8.10-8.35 (m, 1H). LCMS (ESI): m/z calculated for [C$_{23}$H$_{31}$ClN$_2$O$_6$+H]$^+$ 467.19, found 467.29 [M+H]$^+$.

Example 9

Synthesis of 1-((((S)-1-(2-chlorophenyl)-2-oxocyclohexyl)(methyl)carbamoyl)oxy)ethyl 3-hydroxy-2-(hydroxymethyl)propanoate (9)

Example 10

Synthesis of 1-((((S)-1-(2-chlorophenyl)-2-oxocyclohexyl)(methyl)carbamoyl)oxy)ethyl 2-(((3-methyloxetan-3-yl)methyl)sulfinyl)acetate (10)

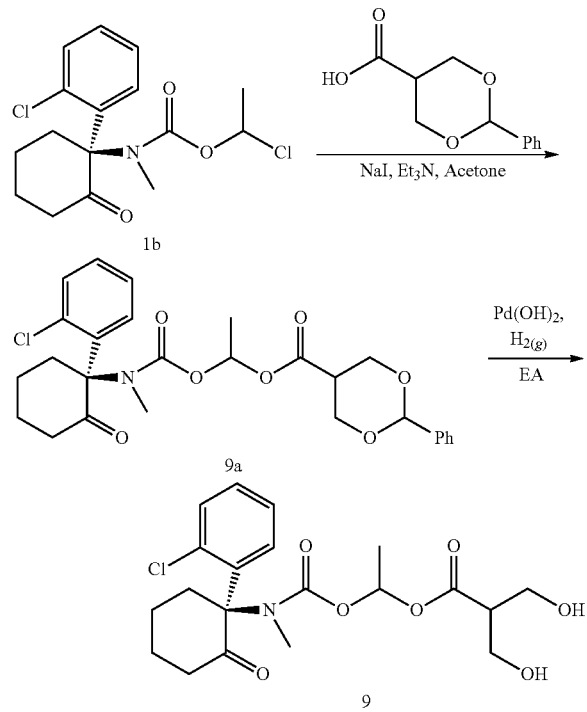

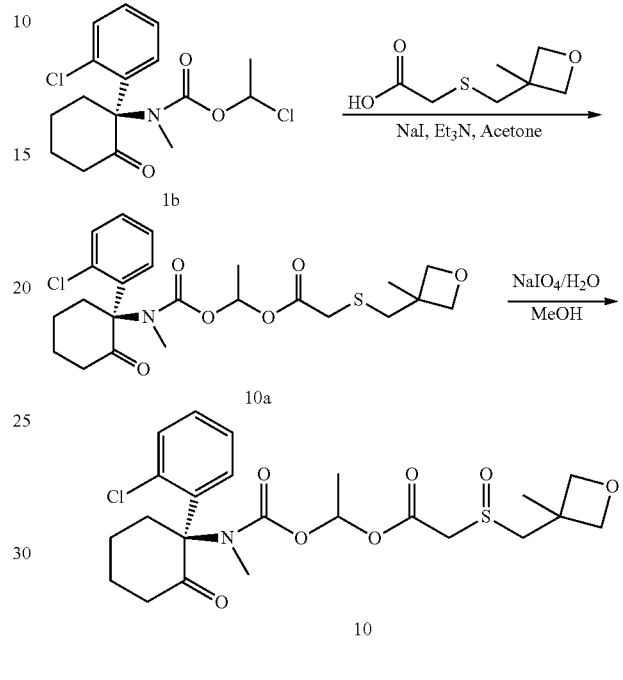

To a solution of 1b (172 mg, 0.5 mmol), NaI (75 mg, 0.5 mmol) and 2-phenyl-1,3-dioxane-5-carboxylic acid (520 mg, 2.5 mmol) in acetone (6 mL) was added triethylamine (0.35 mL, 2.5 mmol). The reaction was heated to 70° C. for 16 h. The reaction was concentrated and redissolved in DCM (10 mL), washed with NaHCO$_{3(sat)}$ (10 mL) and brine (10 mL). The organic layer was dried over MgSO$_4$, filtered and concentrated to provide an oil, which was purified on silica gel column eluting with Hexane/EA (1/0 to 4/1) to afford 175 mg (68% yield) of 9a as a white foam. $^1$H NMR (500 MHz, methanol-d$_4$): δ1.51 (br, 3H), 1.76-1.81 (m, 3H), 2.07 (m, 1H), 2.35-2.50 (m, 2H), 2.70-2.81 (m, 1H), 3.08 (m, 4H), 3.36 (m, 1H), 4.00 (m, 2H), 4.37 (m, 2H), 5.42 (s, 1H), 6.70 (m, 1H), 7.06 (m, 1H), 7.29-7.35 (m, 5H), 7.42-7.47 (m, 3H). LCMS (ESI): m/z calculated for [C$_{27}$H$_{30}$ClNO$_7$+H]$^+$ 516.17, found 516.25 [M+H]$^+$.

To a solution of 9a (100 mg, 0.19 mmol) in EA (10 mL) was added Pd(OH)$_2$/C (11 mg). The reaction was stirred at 25° C. under H$_{2(g)}$ (1 atm) for 50 min. The reaction was filtered through a pad of celite and concentrated to provide an oil, which was purified on silica gel column eluting with Hexane/EA (1/0 to 1/4) to afford 40 mg (49% yield) of the title compound 9 as a white foam. $^1$H NMR (500 MHz, acetone-d$_6$): δ1.47 (br, 3H), 1.76-1.80 (m, 3H), 2.38 (m, 2H), 2.71 (m, 2H), 2.87 and 3.02 (two s, total 3H), 3.23-3.34 (m, 1H), 3.77-3.83 (m, 5H), 6.73 (m, 1H), 7.10 (m, 1H), 7.28-7.34 (m, 2H), 7.44 (m, 1H). LCMS (ESI): m/z calculated for [C$_{20}$H$_{26}$ClNO$_7$+H]$^+$ 428.14, found 428.06 [M+H]$^+$.

To a solution of 1b (172 mg, 0.5 mmol), NaI (75 mg, 0.5 mmol) and 2-(((3-methyloxetan-3-yl)-methyl)thio)acetic acid (264 mg, 1.5 mmol) in acetone (6 mL) was added triethylamine (0.35 mL, 2.5 mmol). The reaction was heated to 70° C. for 2 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 2/1) to afford 180 mg (74% yield) of 10a as a yellow oil. $^1$H NMR (500 MHz, Acetone-d$_6$): δ 1.20-1.35 (m, 3H), 1.40-1.65 (m, 3H), 1.70-1.90 (m, 3H), 2.30-2.60 (m, 3H), 2.65-2.80 (m, 1H), 2.95-3.00 (m, 2H), 3.04 and 3.07 (two s, total 3H), 3.20-3.45 (m, 3H), 4.20-4.30 (m, 2H), 4.35-4.50 (m, 2H), 6.75-6.85 (m, 1H), 7.05-7.15 (m, 1H), 7.25-7.40 (m, 2H), 7.45-7.50 (m, 1H). LCMS (ESI): m/z calculated for [C$_{23}$H$_{30}$ClNO$_6$S+H]$^+$ 484.15, found 484.10 [M+H]$^+$.

To a solution of 10a (140 mg, 0.29 mmol) in MeOH (1.4 mL) was added a solution of NaIO$_4$ (62 mg, 0.29 mmol) in H$_2$O (0.7 mL) dropwise at 0° C. The reaction was stirred at 25° C. for 16 h, filtered and collected the filtrate. The filtrate was concentrated and purified on silica gel column eluting with DCM/MeOH (1/0 to 98/2) to afford 38 mg (26% yield) of the title compound 10 as a white foam. $^1$H NMR (500 MHz, DMSO-d$_6$): δ 1.43-1.51 (m, 6H), 1.68 (m, 3H), 1.98 (m, 1H), 2.30 (m, 2H), 2.60 (m, 1H), 2.96 (m, 3H), 3.01 (m, 1H), 3.14 (m, 1H), 3.42 (m, 1H), 3.98 (m, 1H), 4.10 (m, 1H), 4.21 (m, 1H), 4.28 (m, 1H), 4.48 (m, 1H), 4.59 (m, 1H), 6.70 (m, 1H), 6.98 (m, 1H), 7.33 (m, 2H), 7.46 (m, 1H). LCMS (ESI): m/z calculated for [C$_{23}$H$_{30}$ClNO$_7$S+H]$^+$ 500.14, found 500.1 [M+H]$^+$.

Example 11

Synthesis of 1-(((((S)-1-(2-chlorophenyl)-2-oxocyclohexyl)(methyl)carbamoyl)oxy)ethyl 2-(((3-methyloxetan-3-yl)methyl)sulfonyl)acetate (11)

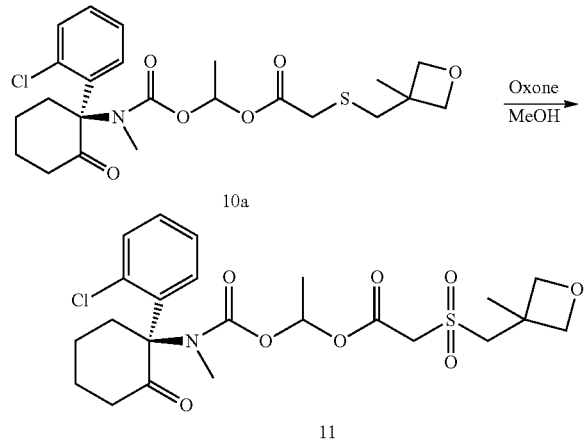

To a solution of 10a (141 mg, 0.29 mmol) in MeOH (1.1 mL) was added a solution of Oxone (356 mg, 0.58 mmol) in H$_2$O (0.9 mL) dropwise at 0° C. The reaction was stirred at 25° C. for 16 h. The reaction was concentrated and re-dissolved in DCM (5 mL), washed with H$_2$O (5 mL). The organic layer was dried over MgSO$_4$, filtered concentrated to provide an oil, which was purified on silica gel column eluting with Hexane/EA (1/0 to 1/1) to afford 42 mg (29% yield) of the title compound 11 as a white foam. $^1$H NMR (500 MHz, acetone-d$_6$): δ 1.25-1.36 (m, 1H), 1.41-1.68 (m, 7H), 1.70-1.88 (m, 4H), 2.34-2.56 (m, 2H), 3.04 and 3.07 (two s, total 3H), 3.16-3.38 (m, 1H), 3.74-3.88 (m, 2H), 4.20-4.36 (m, 3H), 4.58-4.70 (m, 1H), 6.77-6.88 (m, 1H), 7.06-7.15 (m, 1H), 7.27-7.40 (m, 2H), 7.41-7.50 (m, 1H). LCMS (ESI): m/z calculated for [C$_{23}$H$_{30}$ClNO$_8$S+H]$^+$ 516.14, found 516.24 [M+H]$^+$.

Example 12

Synthesis of 1-((((S)-1-(2-chlorophenyl)-2-oxocyclohexyl)(methyl)carbamoyl)oxy)ethyl (2R)-2-hydroxypropanoate (12)

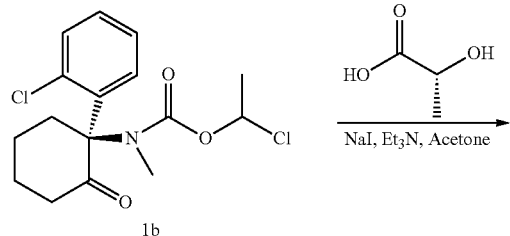

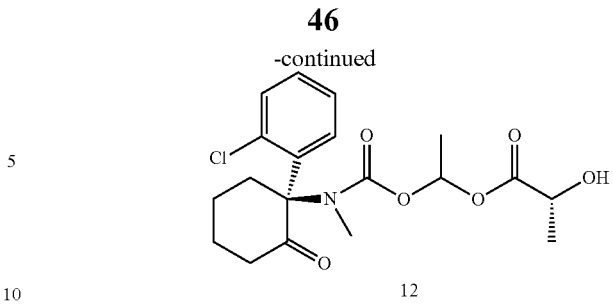

To a solution of 1b (172 mg, 0.5 mmol), NaI (75 mg, 0.5 mmol) and R-lactic acid (227 mg, 2.5 mmol) in acetone (6 mL) was added triethylamine (0.35 mL, 2.5 mmol). The reaction was heated to 70° C. for 3.5 h. The reaction was concentrated and re-dissolved in DCM (10 mL), washed with H$_2$O (10 mL) and brine (10 mL). The organic layer was dried over MgSO$_4$, filtered and concentrated to provide an oil, which was purified on silica gel column eluting with Hexane/EA (1/0 to 2/1) to afford 100 mg (50% yield) of the title compound 12 as a white foam. $^1$H NMR (500 MHz, DMSO-d$_6$): δ 1.24 (m, 3H), 1.46 (m, 3H), 1.68 (m, 3H), 1.98 (br, 1H), 2.32 (m, 2H), 2.58 (m, 1H), 2.96 (m, 3H), 3.13 (m, 1H), 4.11 (m, 1H), 5.47-5.56 (m, 1H), 6.64 (m, 1H), 6.94 (m, 1H), 7.32 (m, 2H), 7.46 (m, 1H). LCMS (ESI): m/z calculated for [C$_{19}$H$_{24}$ClNO$_6$+H]$^+$ 398.13, found 398.13 [M+H]$^+$.

Example 13

Synthesis of 1-((((S)-1-(2-chlorophenyl)-2-oxocyclohexyl)(methyl)carbamoyl)oxy)ethyl (2R)-2-acetoxypropanoate (13)

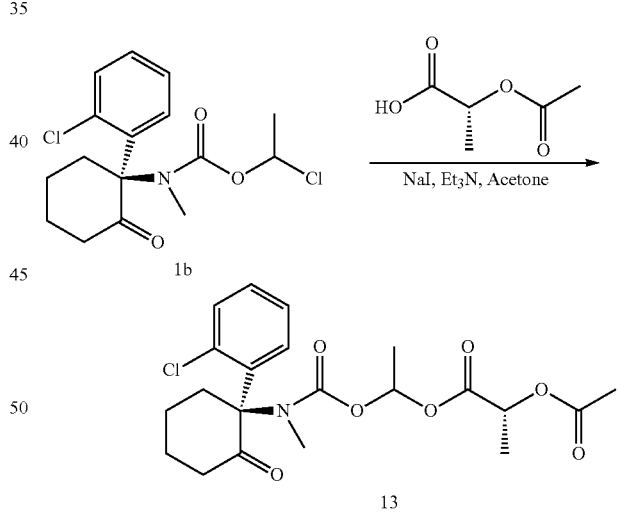

To a solution of 1b (172 mg, 0.5 mmol), NaI (79 mg, 0.525 mmol) and (R)-2-acetoxypropanoic acid (172 mg, 0.5 mmol) in acetone (6 mL) was added triethylamine (0.35 mL, 2.5 mmol). The reaction was heated to 70° C. for 16 h. The reaction was concentrated and dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 65/35) to afford 204 mg (93% yield) of the title compound 13 as a white foam. $^1$H NMR (500 MHz, DMSO-d$_6$): δ 1.20-1.55 (m, 6H), 1.56-1.69 (m, 4H), 2.06-2.10 (m, 3H), 2.25-2.42 (m, 2H), 2.55-2.65 (m, 1H), 2.97 (d, J=6.4 Hz, 3H), 3.05-3.21 (m, 1H), 4.85-5.02 (m, 1H), 6.60-6.70 (m, 1H), 6.90-7.05 (m, 1H), 7.21-7.39 (m, 2H), 7.41-7.48 (m, 1H). LCMS (ESI): m/z calculated for $[C_{21}H_{26}ClNO_7+H]^+$ 440.14, found 440.0 $[M+H]^+$.

Example 14

Synthesis of 1-((((S)-1-(2-chlorophenyl)-2-oxocyclohexyl)(methyl)carbamoyl)oxy)ethyl nicotinate (14)

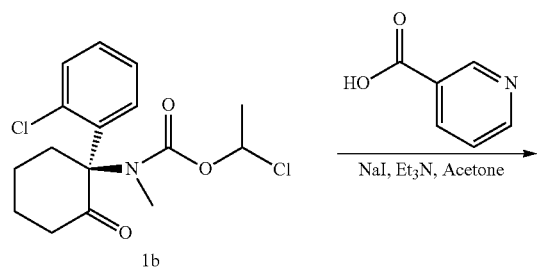

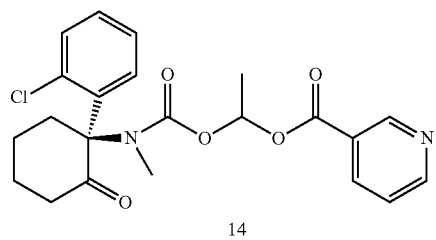

To a solution of 1b (86 mg, 0.25 mmol), NaI (75 mg, 0.5 mmol) and nicotinic acid (92 mg, 0.75 mmol) in acetone (3 mL) was added triethylamine (0.18 mL, 1.25 mmol). The reaction was heated to 70° C. for 3 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 3/1) to afford 47 mg (47% yield) of the title compound 14 as a white solid. $^1H$ NMR (500 MHz, acetone-$d_6$): δ 1.46-1.88 (m, 6H), 2.28-2.62 (m, 3H), 2.66-2.78 (m, 1H), 3.07 and 3.11 (two s, total 3H), 3.18-3.38 (m, 1H), 6.94-7.06 (m, 1H), 7.08-7.18 (m, 1H), 7.22-7.36 (m, 2H), 7.40-7.50 (m, 1H), 7.54-7.62 (m, 1H), 8.18-8.40 (m, 1H), 8.78-8.88 (m, 1H), 9.04-9.24 (m, 1H). LCMS (ESI): m/z calculated for $[C_{22}H_{23}ClN_2O_5+H]^+$ 431.13, found 431.16 $[M+H]^+$.

Example 15

Synthesis of 1-((((S)-1-(2-chlorophenyl)-2-oxocyclohexyl)(methyl)carbamoyl)oxy)ethyl 3-benzylbenzoate (15)

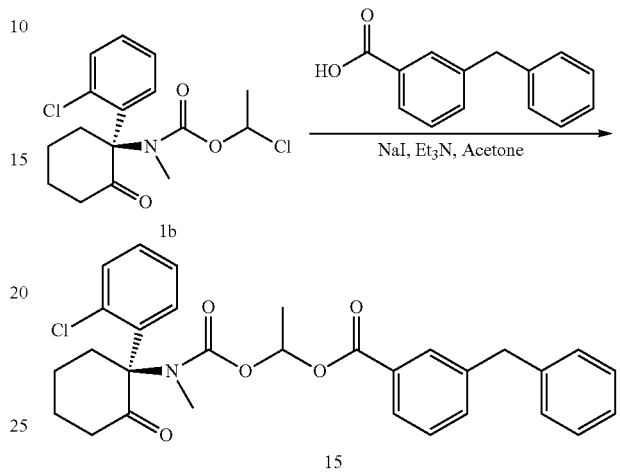

To a solution of 1b (54 mg, 0.16 mmol), NaI (25 mg, 0.17 mmol) and 3-benzylbenzoic acid (100 mg, 0.47 mmol) in acetone (2 mL) was added triethylamine (0.11 mL, 0.785 mmol). The reaction was heated to 70° C. for 16 h. The reaction was concentrated and dissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 4/1) to afford 60 mg (74% yield) of the title compound 15 as a colorless solid. $^1H$ NMR (500 MHz, methanol-$d_4$): δ 1.51-1.69 (m, 2H), 1.70-1.88 (m, 3H), 1.97-2.12 (m, 1H), 2.29-2.48 (m, 2H), 2.68-2.80 (m, 1H), 3.05 (d, J=12.9 Hz, 3H), 3.24-3.30 (m, 1H), 3.32-3.44 (m, 1H), 4.05 (d, J=4.3 Hz, 2H), 6.92-6.97 (m, 1H), 7.01-7.08 (m, 1H), 7.13-7.22 (m, 4H), 7.23-7.33 (m, 3H), 7.35-7.45 (m, 2H), 7.46-7.51 (m, 1H), 7.76-7.92 (m, 2H). LCMS (ESI): m/z calculated for $[C_{30}H_{30}ClNO_5+H]^+$ 520.18, found 520.42 $[M+H]^+$.

Example 16

Synthesis of 1-((((S)-1-(2-chlorophenyl)-2-oxocyclohexyl)(methyl)carbamoyl)oxy)ethyl benzo[d][1,3]dioxole-5-carboxylate (16)

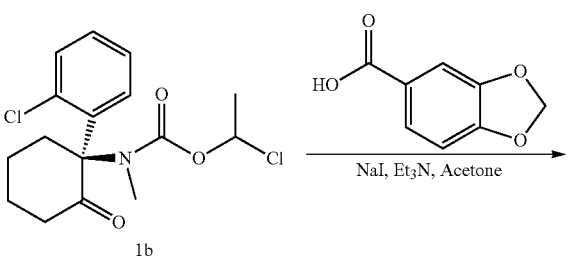

-continued

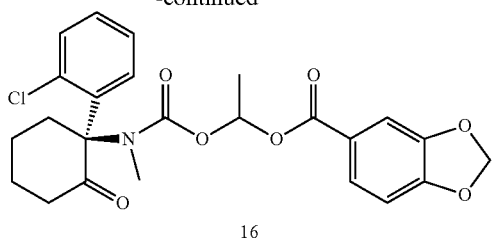

16

To a solution of 1b (86 mg, 0.25 mmol), NaI (39 mg, 0.26 mmol) and benzo[d][1,3]dioxole-5-carboxylic acid (125 mg, 0.75 mmol) in acetone (3 mL) was added triethylamine (0.18 mL, 1.25 mmol). The reaction was heated to 70° C. for 16 h. The reaction was concentrated and dissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 7/3) to afford 110 mg (93% yield) of the title compound 16 as a white solid. $^1$H NMR (500 MHz, methanol-$d_4$): δ 1.43-1.70 (m, 3H), 1.71-1.90 (m, 3H), 2.03-2.15 (m, 1H), 2.28-2.52 (m, 2H), 2.65-2.87 (m, 1H), 3.07 (d, J=15.4 Hz, 3H), 3.34-3.45 (m, 2H), 6.08 (s, 2H), 6.87-6.96 (m, 2H), 7.02-7.12 (m, 1H), 7.22-7.33 (m, 2H), 7.34-7.50 (m, 2H), 7.57-7.72 (m, 1H). LCMS (ESI): m/z calculated for $[C_{24}H_{24}ClNO_7+H]^+$ 474.12, found 474.3 $[M+H]^+$.

Example 17

Synthesis of 1-((((S)-1-(2-chlorophenyl)-2-oxocyclohexyl)(methyl)carbamoyl)oxy)ethyl 1-methylpiperidine-4-carboxylate (17)

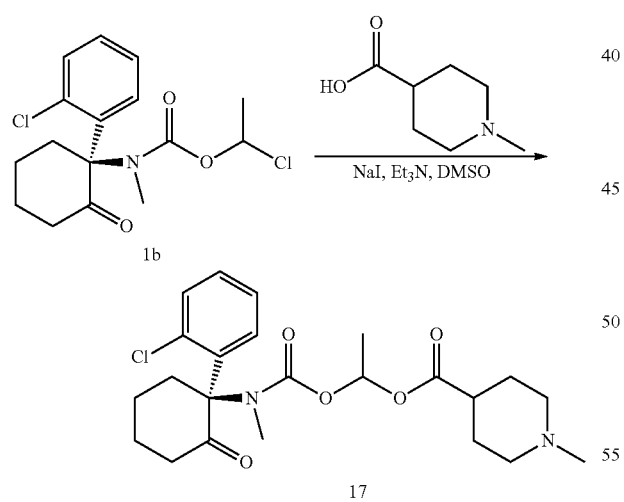

17

To a solution of 1b (86 mg, 0.25 mmol), NaI (75 mg, 0.5 mmol) and 1-methylpiperidine-4-carboxylic acid (117 mg, 0.82 mmol) in DMSO (1 mL) was added triethylamine (0.18 mL, 1.25 mmol). The reaction was stirred at 25° C. for 3 h. The reaction was concentrated and then purified on silica gel column eluting with DCM/MeOH (1/0 to 95/5) to afford 23 mg (20% yield) of the title compound 17 as a yellow oil. $^1$H NMR (600 MHz, methanol-$d_4$): δ 1.38-1.66 (m, 3H), 1.72-1.90 (m, 5H), 1.92-2.02 (m, 2H), 2.06-2.12 (m, 1H), 2.28-2.62 (m, 8H), 2.68-2.82 (m, 1H), 2.86-3.14 (m, 2H), 3.05 and 3.07 (two s, total 3H), 3.31-3.40 (m, 1H), 6.68-6.77 (m, 1H), 6.98-7.08 (m, 1H), 7.26-7.37 (m, 2H), 7.44-7.50 (m, 1H). LCMS (ESI): m/z calculated for $[C_{23}H_{31}ClN_2O_5+H]^+$ 451.19, found 451.2 $[M+H]^+$.

Example 18

Synthesis of 1-((((S)-1-(2-chlorophenyl)-2-oxocyclohexyl)(methyl)carbamoyl)oxy)ethyl isonicotinate (18)

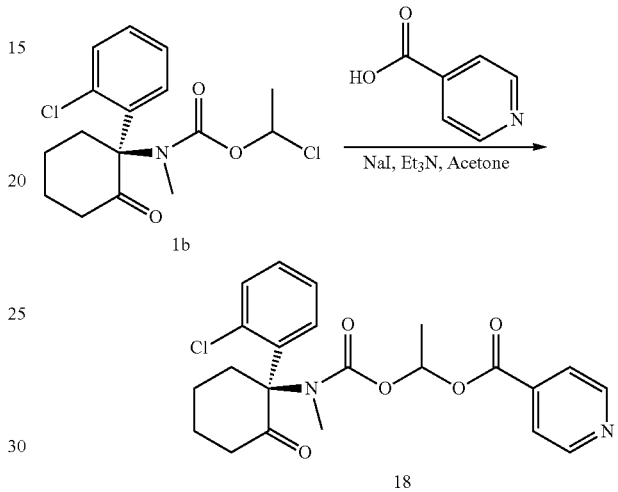

18

To a solution of 1b (86 mg, 0.25 mmol), NaI (75 mg, 0.5 mmol) and isonicotinic acid (92 mg, 0.75 mmol) in acetone (3 mL) was added triethylamine (0.18 mL, 1.25 mmol). The reaction was heated to 70° C. for 3 h. The reaction was concentrated and dissolved in DCM (5 mL), washed with $NaHCO_{3\ (sat)}$ (5 mL) and brine (5 mL). The organic layer was dried over $MgSO_4$, filtered and concentrated to provide an oil, which was purified on silica gel column eluting with Hexane/EA (1/0 to 8/2) to afford 50 mg (46% yield) of the title compound 18 as a white solid. $^1$H NMR (500 MHz, acetone-$d_6$): δ 1.50-1.87 (m, 6H), 2.32-2.54 (m, 3H), 2.65-2.78 (m, 1H), 3.04-3.13 (m, 3H), 3.17-3.35 (m, 1H), 6.96-7.04 (m, 1H), 7.07-7.17 (m, 1H), 7.23-7.36 (m, 2H), 7.39-7.48 (m, 1H), 7.77-7.92 (m, 2H), 8.78-8.86 (m, 2H). LCMS (ESI): m/z calculated for $[C_{22}H_{23}ClN_2O_5+H]^+$ 431.13, found 430.8 $[M+H]^+$.

Example 19

Synthesis of 1-((((S)-1-(2-chlorophenyl)-2-oxocyclohexyl)(methyl)carbamoyl)oxy)ethyl isobutyrylglycinate (19)

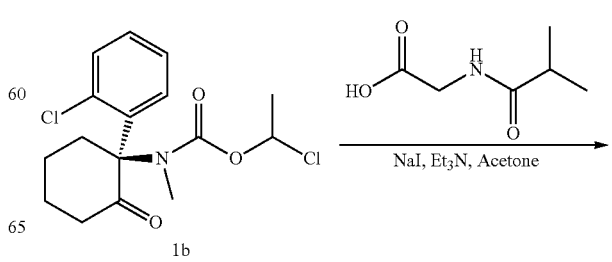

-continued

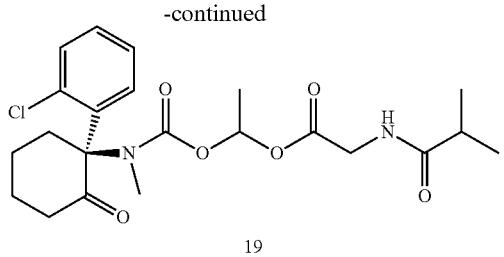

19

To a solution of 1b (86 mg, 0.25 mmol), NaI (75 mg, 0.5 mmol) and 2-isobutyramido)acetic acid (109 mg, 0.75 mmol) in acetone (3 mL) was added triethylamine (0.18 mL, 1.25 mmol). The reaction was heated to 70° C. for 16 h. The reaction was concentrated and dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/1) to afford 57 mg (50% yield) of the title compound 19 as a white solid. $^1$H NMR (500 MHz, methanol-d$_4$): δ 1.12-1.16 (m, 6H), 1.52 (s, 2H), 1.72-1.89 (m, 3H), 2.03-2.12 (m, 1H), 2.32-2.56 (m, 3H), 2.66-2.85 (m, 1H), 3.00-3.08 (m, 3H), 3.25-3.40 (m, 2H), 3.84-4.01 (m, 2H), 6.70-6.78 (m, 1H), 7.01-7.10 (m, 1H), 7.26-7.35 (m, 2H), 7.44-7.47 (m, 1H). LCMS (ESI): m/z calculated for [C$_{22}$H$_{29}$ClN$_2$O$_6$+H]$^+$ 453.17, found 452.6 [M+H]$^+$.

Example 20

Synthesis of 1-((((S)-1-(2-chlorophenyl)-2-oxocyclohexyl)(methyl)carbamoyl)oxy)ethyl 3-acetamidopropanoate (20)

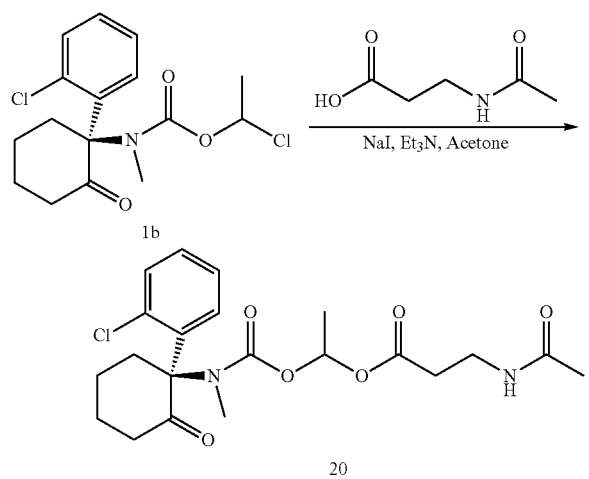

20

To a solution of 1b (86 mg, 0.25 mmol), NaI (75 mg, 0.5 mmol) and 3-acetamidopropanoic acid (98 mg, 0.75 mmol) in acetone (3 mL) was added triethylamine (0.18 mL, 1.25 mmol). The reaction was heated to 70° C. for 22 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/2) to afford 20 mg (18% yield) of the title compound 20 as a light-yellow oil. $^1$H NMR (600 MHz, DMSO-d$_6$): δ 1.30-1.75 (m, 7H), 1.78 (d, J=2.4 Hz, 3H), 1.90-2.05 (m, 1H), 2.20-2.45 (m, 3H), 2.55-2.65 (m, 1H), 2.95 and 2.97 (two s, total 3H), 3.00-3.25 (m, 3H), 6.55-6.70 (m, 1H), 6.90-7.10 (m, 1H), 7.25-7.60 (m, 3H), 7.80-7.90 (m, 1H). LCMS (ESI): m/z calculated for [C$_{21}$H$_{27}$ClN$_2$O$_6$+H]$^+$ 439.16, found 438.9 [M+H]$^+$.

Example 21

Synthesis of 1-((((S)-1-(2-chlorophenyl)-2-oxocyclohexyl)(methyl)carbamoyl)oxy)ethyl 4-acetamidobutanoate (21)

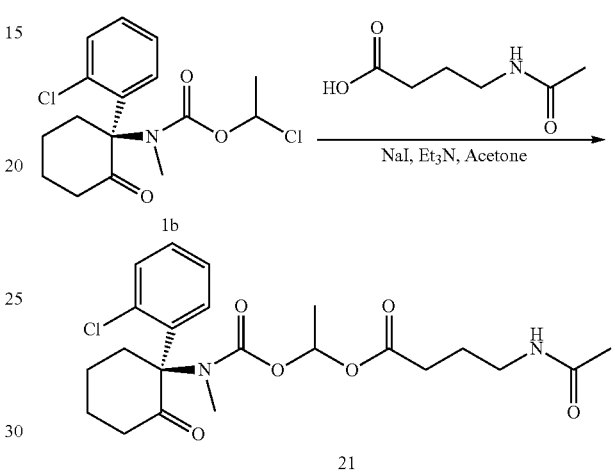

21

To a solution of 1b (86 mg, 0.25 mmol), NaI (75 mg, 0.5 mmol) and 4-acetamidobutanoic acid (109 mg, 0.75 mmol) in acetone (3 mL) was added triethylamine (0.18 mL, 1.25 mmol). The reaction was heated to 70° C. for 22 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/2) to afford 72 mg (64% yield) of the title compound 21 as a white foam. $^1$H NMR (600 MHz, DMSO-d$_6$): δ 1.30-1.55 (m, 3H), 1.56-1.76 (m, 5H), 1.78 (d, J=2.7 Hz, 3H), 1.94-2.04 (m, 1H), 2.23-2.40 (m, 4H), 2.54-2.65 (m, 1H), 2.95 and 2.97 (two s, total 3H), 2.99-3.07 (m, 2H), 3.09-3.19 (m, 1H), 6.58-6.66 (m, 1H), 6.92-7.00 (m, 1H), 7.28-7.36 (m, 2H), 7.44-7.49 (m, 1H), 7.80-7.88 (m, 1H). LCMS (ESI): m/z calculated for [C$_{22}$H$_{29}$ClN$_2$O$_6$+H]$^+$ 453.17, found 452.9 [M+H]$^+$.

Example 22

Synthesis of (S)-(((1-(2-chlorophenyl)-2-oxocyclohexyl)(methyl)carbamoyl)oxy)methyl 2-(3-methyloxetan-3-yl)acetate (22)

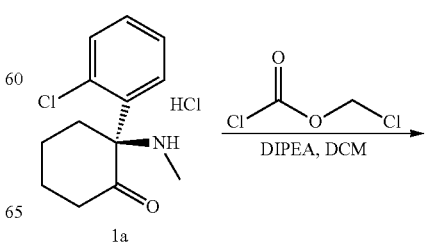

1a

53

-continued

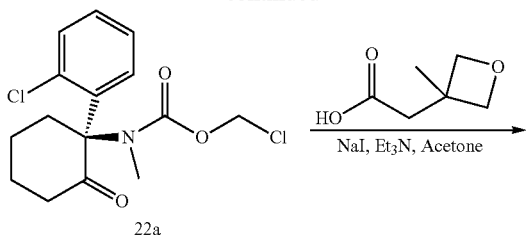

22a

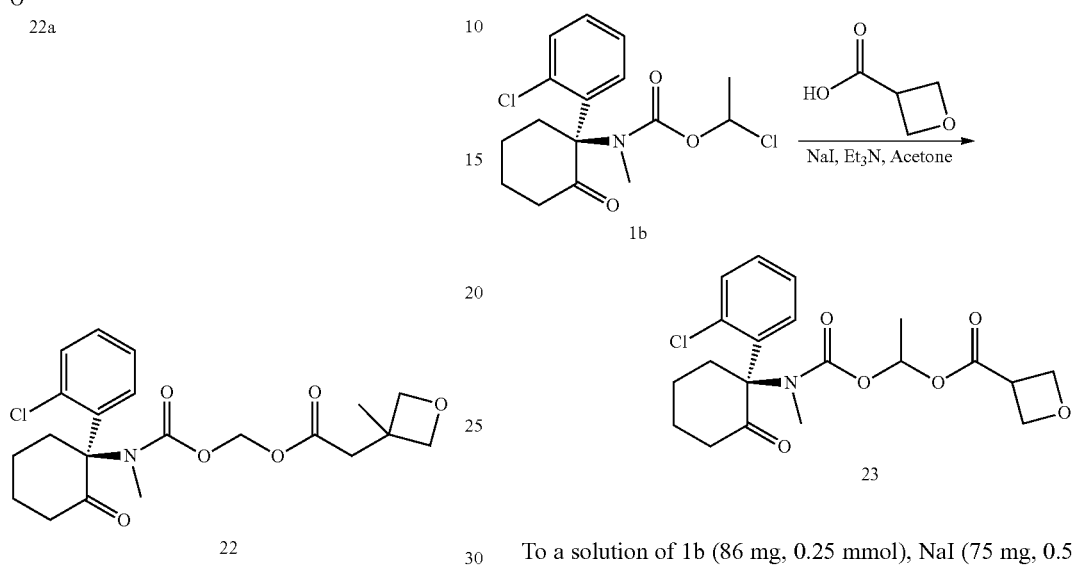

22

To a solution of S-ketamine hydrochloride 1a (102 mg, 0.375 mmol) and DIPEA (97 mg, 0.75 mmol) in DCM (3.75 mL) was added chloromethyl chloroformate (121 mg, 0.94 mmol) slowly at 0° C. The reaction was stirred at 25° C. for 24 h. The reaction was diluted with DCM (5 mL) and washed with water (5 mL) and brine (5 mL). The organic layer was dried over MgSO4, filtered and concentrated to provide an oil, which was purified on silica gel column eluting with Hexane/EA (1/0 to 9/1) to afford 93 mg (75% yield) of 22a as a white solid. $^1$H NMR (500 MHz, acetone-$d_6$): δ 1.68-1.90 (m, 4H), 2.42-2.49 (m, 1H), 2.50-2.59 (m, 1H), 2.65-2.75 (m, 1H), 3.07 (s, 3H), 3.20-3.33 (m, 1H), 5.88 (s, 2H), 7.05-7.13 (m, 1H), 7.28-7.36 (m, 2H), 7.43-7.50 (m, 1H). LCMS (ESI): m/z calculated for $[C_{15}H_{17}Cl_2N_1O_3+H]^+$ 330.06, found 330.2 $[M+H]^+$.

To a solution of 22a (82 mg, 0.25 mmol), NaI (75 mg, 0.5 mmol) and 2-(3-methyloxetan-3-yl)acetic acid (98 mg, 0.75 mmol) in acetone (3 mL) was added $K_2CO_3$ (173 mg, 1.25 mmol). The reaction was heated to 70° C. for 2 h. The reaction was concentrated and re-dissolved in DCM (5 mL), washed with $NaHCO_{3(sat)}$ (5 mL) and brine (5 mL). The organic layer was dried over MgSO4, filtered and concentrated to provide an oil, which was purified on silica gel column eluting with Hexane/EA (1/0 to 1/2) to afford 84 mg (80% yield) of the title compound 22 as a white solid. $^1$H NMR (500 MHz, acetone-$d_6$): δ 1.39 (s, 3H), 1.68-1.88 (m, 3H), 1.98-2.09 (m, 1H), 2.41-2.53 (m, 2H), 2.65-2.73 (m, 1H), 2.77 (s, 2H), 3.03 (s, 3H), 3.19-3.32 (m, 1H), 4.28 (d, J=5.85 Hz, 2H), 4.50 (d, J=5.85 Hz, 2H), 5.66-5.86 (m, 2H), 7.05-7.11 (m, 1H), 7.28-7.35 (m, 2H), 7.42-7.48 (m, 1H). LCMS (ESI): m/z calculated for $[C_{21}H_{26}ClNO_6+H]^+$ 424.14, found 424.5 $[M+H]^+$.

54

Example 23

Synthesis of 1-((((S)-1-(2-chlorophenyl)-2-oxocyclohexyl)(methyl)carbamoyl)oxy)ethyl oxetane-3-carboxylate (23)

To a solution of 1b (86 mg, 0.25 mmol), NaI (75 mg, 0.5 mmol) and oxetane-3-carboxylic acid (77 mg, 0.75 mmol) in acetone (3 mL) was added triethylamine (0.18 mL, 1.25 mmol). The reaction was heated to 70° C. for 16 h. The reaction was concentrated and re-dissolved in DCM (5 mL), washed with $NaHCO_{3(sat)}$ (5 mL) and brine (5 mL). The organic layer was dried over MgSO4, filtered and concentrated to provide an oil, which was purified on silica gel column eluting with Hexane/EA (7/3) to afford 40 mg (49% yield) of the title compound 26 as a light yellow oil. $^1$H NMR (600 MHz, acetone-$d_6$): δ 1.33-1.64 (m, 3H), 1.68-1.90 (m, 4H), 2.34-2.53 (m, 2H), 2.65-2.77 (m, 1H), 3.05 and 3.06 (two s, total 3H), 3.20-3.34 (m, 1H), 3.82-3.94 (m, 1H), 4.55-4.82 (m, 4H), 6.75-6.82 (m, 1H), 7.02-7.11 (m, 1H), 7.26-7.36 (m, 2H), 7.41-7.48 (m, 1H). LCMS (ESI): m/z calculated for $[C_{20}H_{24}ClNO_6+H]^+$ 410.13, found 409.9 $[M+H]^+$.

Example 24

Synthesis of 1-((((S)-1-(2-chlorophenyl)-2-oxocyclohexyl)(methyl)carbamoyl)oxy)propyl 2-(3-methyloxetan-3-yl)acetate (24)

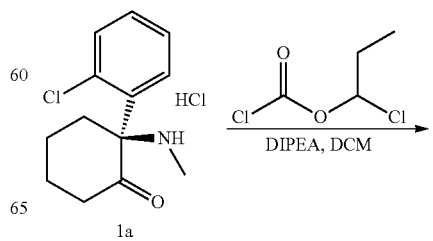

-continued

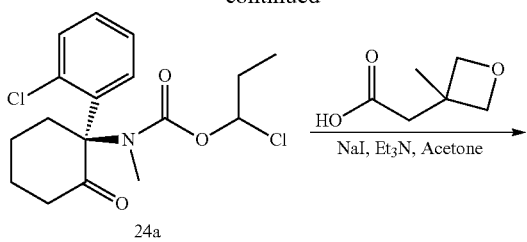

24a

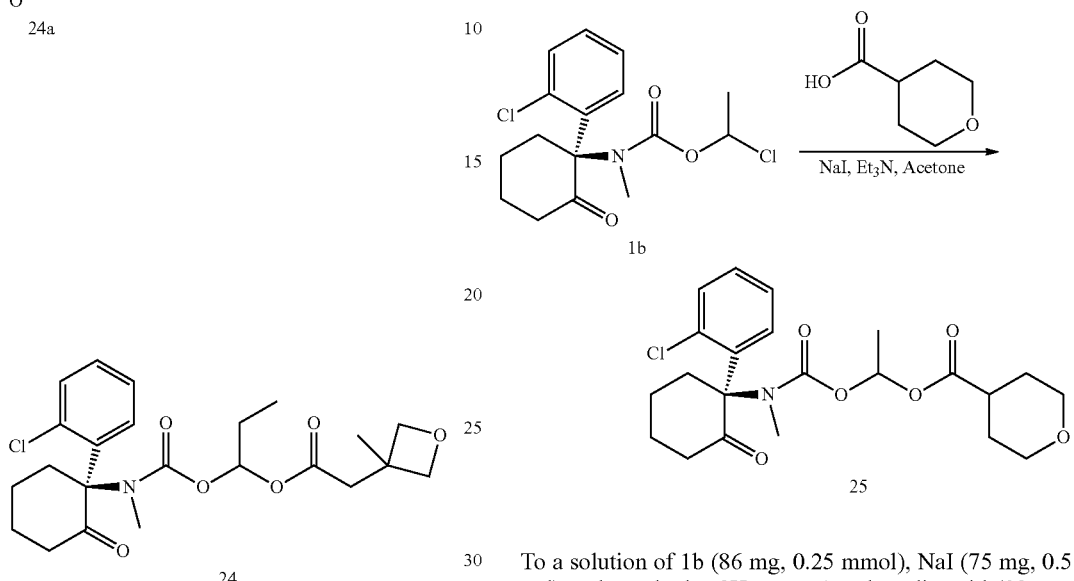

To a solution of S-ketamine hydrochloride 1a (137 mg, 0.5 mmol) and DIPEA (130 mg, 1.0 mmol) in DCM (5 mL) was added 1-chloroethyl carbonochloridate (94 mg, 0.6 mmol) slowly at 0° C. The reaction was stirred at 25° C. for 16 h. The reaction was diluted with DCM (5 mL) and washed with water (5 mL) and brine (5 mL). The organic layer was dried over MgSO$_4$, filtered and concentrated to provide an oil, which was purified on silica gel column eluting with Hexane/EA (1/0 to 10/1) to afford 133 mg (74% yield) of 24a as a colorless oil. $^1$H NMR (600 MHz, CDCl$_3$): δ 1.05 (br, 3H), 1.75-1.89 (m, 4H), 2.04 (m, 2H), 2.37-2.50 (br, 1H), 2.58 (m, 1H), 2.71 (m, 1H), 3.01 and 3.08 (two s, total 3H), 3.27-3.35 (br, 1H), 6.39 (m, 1H), 6.94-7.00 (m, 1H), 7.24 (m, 2H), 7.44 (m, 1H).

To a solution of 24a (90 mg, 0.25 mmol), NaI (37 mg, 0.25 mmol), and 2-(3-methyloxetan-3-yl)acetic acid (98 mg, 0.75 mmol) in acetone (1 mL) was added triethylamine (0.18 mL, 1.25 mmol). The reaction was heated to 70° C. for 10 h. The reaction was concentrated and re-dissolved in DCM (5 mL), washed with NaHCO$_3$(sat) (5 mL) and brine (5 mL). The organic layer was dried over MgSO$_4$, filtered and concentrated to provide an oil, which was purified on silica gel column eluting with Hexane/EA (1/0 to 2/1) to afford 32 mg (28% yield) of the title compound 24 as a yellow oil. $^1$H NMR (600 MHz, acetone-d$_6$): δ 0.89-1.04 (m, 3H), 1.38-1.41 (m, 3H), 1.88-1.78 (m, 5H), 2.41-2.55 (m, 2H), 2.67-2.84 (m, 4H), 3.06 and 3.09 (two s, total 3H), 3.20-3.37 (m, 1H), 4.29-4.31 (m, 2H), 4.50-4.54 (m, 2H), 6.63-6.67 (m, 1H), 7.09-7.014 (m, 1H), 7.32-7.35 (m, 2H), 7.49-7.46 (m, 1H). LCMS (ESI): m/z calculated for [C$_{23}$H$_{30}$ClNO$_6$+H]$^+$ 452.18, found 452.03 [M+H]$^+$.

Example 25

Synthesis of 1-((((S)-1-(2-chlorophenyl)-2-oxocyclohexyl)(methyl)carbamoyl)oxy)ethyl tetrahydro-2H-pyran-4-carboxylate (25)

To a solution of 1b (86 mg, 0.25 mmol), NaI (75 mg, 0.5 mmol) and tetrahydro-2H-pyran-4-carboxylic acid (98 mg, 0.75 mmol) in acetone (3 mL) was added triethylamine (0.18 mL, 1.25 mmol). The reaction was heated to 70° C. for 16 h. The reaction was concentrated and dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (7/3) to afford 72 mg (66% yield) of the title compound 25 as a white foam. $^1$H NMR (500 MHz, methanol-d$_4$): δ 1.51 (s, 3H), 1.61-1.91 (m, 7H), 2.03-2.12 (m, 1H), 2.32-2.52 (m, 2H), 2.56-2.65 (m, 1H), 2.67-2.83 (m, 1H), 3.05 (d, J=11.5 Hz, 3H), 3.32-3.39 (m, 1H), 3.40-3.50 (m, 2H), 3.81-3.94 (m, 2H), 6.69-6.75 (m, 1H), 6.99-7.08 (m, 1H), 7.26-7.32 (m, 2H), 7.43-7.48 (m, 1H). LCMS (ESI): m/z calculated for [C$_{22}$H$_{28}$ClNO$_6$+H]$^+$ 438.16, found 438.1 [M+H]$^+$.

Example 26

Synthesis of 1-((((S)-1-(2-chlorophenyl)-2-oxocyclohexyl)(methyl)carbamoyl)oxy)-2-methylpropyl 2-(3-methyloxetan-3-yl)acetate (26)

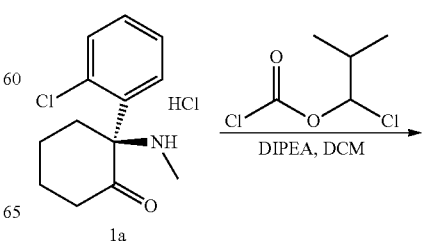

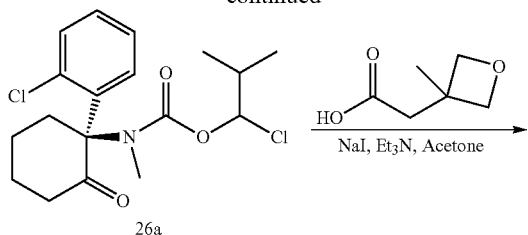

26a

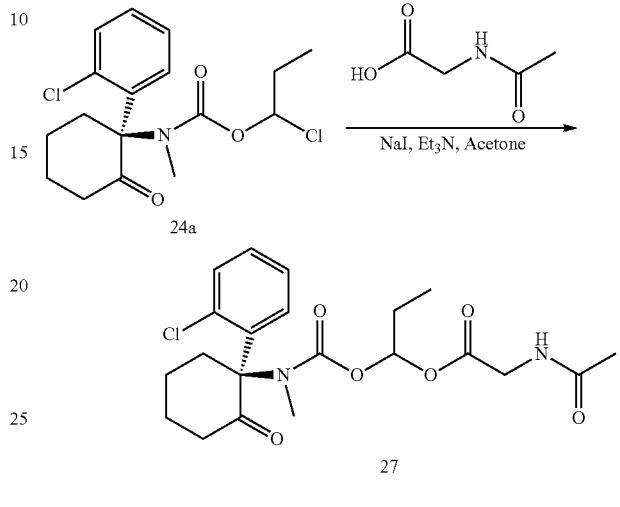

24a

27

To a solution of S-ketamine hydrochloride 1a (200 mg, 0.73 mmol) and DIPEA (0.25 mL, 1.46 mmol) in DCM (8 mL) was added 1-chloro-2-methylpropyl chloroformate (312 mg, 1.83 mmol) slowly at 0° C. and then stirred at 25° C. for 1 h. The reaction was diluted with DCM (5 mL) and washed with water (5 mL) and brine (5 mL). The organic layer was dried over MgSO$_4$, filtered and concentrated to provide an oil, which was purified on silica gel column eluting with Hexane/EA (1/0 to 9/1) to afford 230 mg (85% yield) of 26a as a white solid. $^1$H NMR (600 MHz, acetone-d$_6$): δ 0.75-1.27 (m, 6H), 1.68-1.90 (m, 3H), 2.38-2.58 (m, 2H), 2.65-2.77 (m, 1H), 2.83-2.85 (m, 2H), 3.08 and 3.12 (two s, total 3H), 3.18-3.36 (m, 1H), 6.35 (d, J=4.26 Hz, 1H), 7.01-7.11 (m, 1H), 7.28-7.35 (m, 2H), 7.44-7.49 (m, 1H). LCMS (ESI): m/z calculated for [C$_8$H$_{23}$Cl$_2$NO$_3$+H]$^+$ 372.11, found 371.8 [M+H]$^+$.

To a solution of 26a (93 mg, 0.25 mmol), NaI (75 mg, 0.5 mmol) and 2-(3-methyloxetan-3-yl)acetic acid (98 mg, 0.75 mmol) in acetone (3 mL) was added triethylamine (0.18 mL, 1.25 mmol). The reaction was heated to 70° C. for 5 h. The reaction was concentrated and dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (7/3) to afford 15 mg (13% yield) of the title compound 26 as a white foam. $^1$H NMR (500 MHz, methanol-d$_4$): δ 1.01 (s, 6H), 1.40 (s, 3H), 1.72-1.90 (m, 3H), 1.99-2.16 (m, 2H), 2.32-2.52 (m, 2H), 2.64-2.88 (m, 3H), 3.05 (d, J=20.2 Hz, 3H), 3.33-3.43 (m, 1H), 4.38 (dd, J=1.8, 1.7 Hz, 2H), 4.6 (d, J=5.8 Hz, 2H), 6.50 (dd, J=5.0, 4.9 Hz, 1H), 7.01-7.10 (m, 1H), 7.27-7.32 (m, 2H), 7.43-7.48 (m, 1H). LCMS (ESI): m/z calculated for [C$_{24}$H$_{32}$ClNO$_6$+H]$^+$ 466.19, found 466.1 [M+H]$^+$.

Example 27

Synthesis of 1-((((S)-1-(2-chlorophenyl)-2-oxocyclohexyl)(methyl)carbamoyl)oxy)propyl acetylglycinate (27)

To a solution of 24a (90 mg, 0.25 mmol), NaI (37 mg, 0.25 mmol), and acetylglycine (88 mg, 0.75 mmol) in acetone (1 mL) was added triethylamine (0.18 mL, 1.25 mmol). The reaction was heated to 70° C. for 10 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/2) to afford 18 mg (16% yield) of the title compound 27 as a white solid. $^1$H NMR (600 MHz, acetone-d$_6$) δ 0.86-1.04 (m, 3H), 1.74-1.84 (m, 4H), 1.94-1.95 (m, 3H), 2.06-2.07 (m, 3H), 2.37-2.49 (m, 2H), 2.67-2.79 (m, 1H), 3.03 and 3.07 (two s, total 3H), 3.21-3.34 (m, 1H), 3.85-3.94 (m, 1H), 3.99-4.05 (m, 1H), 6.62-6.66 (m, 1H), 7.06-7.09 (m, 1H), 7.28-7.35 (m, 2H), 7.45-7.44 (m, 1H). LCMS (ESI): m/z calculated for [C$_{21}$H$_{27}$ClN$_2$O$_6$+H]$^+$ 439.16, found 439.00 [M+H]$^+$.

Example 28

Synthesis of 1-((((S)-1-(2-chlorophenyl)-2-oxocyclohexyl)(methyl)carbamoyl)oxy)-2-methylpropy acetylglycinate (28)

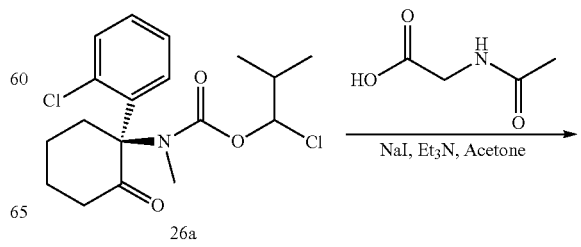

26a

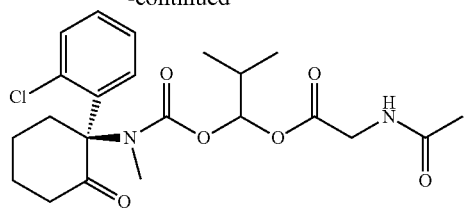

28

To a solution of 26a (93 mg, 0.25 mmol), NaI (75 mg, 0.5 mmol) and acetylglycine (88 mg, 0.75 mmol) in acetone (3 mL) was added triethylamine (0.18 mL, 1.25 mmol). The reaction was heated to 70° C. for 16 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (2/3) to afford 29 mg (28% yield) of the title compound 28 as a colorless oil. $^1$H NMR (600 MHz, DMSO-d$_6$): δ 0.76-1.11 (m, 6H), 1.60-1.78 (m, 3H), 1.86 (d, J=2.0 Hz, 3H), 1.95-2.05 (m, 1H), 2.26-2.40 (m, 2H), 2.52-2.68 (m, 1H), 2.65 and 2.98 (two s, total 3H), 3.04-3.20 (m, 1H), 3.71-3.97 (m, 3H), 6.38-6.47 (m, 1H), 6.89-6.99 (m, 1H), 7.28-7.36 (m, 2H), 7.43-7.49 (m, 1H), 8.33-8.43 (m, 1H). LCMS (ESI): m/z calculated for [C$_{22}$H$_{29}$ClN$_2$O$_6$+H]$^+$ 453.17, found 453.3 [M+H]$^+$.

Example 29

Synthesis of (S)-(((1-(2-chlorophenyl)-2-oxocyclohexyl)(methyl)carbamoyl)oxy)methyl nicotinate (29)

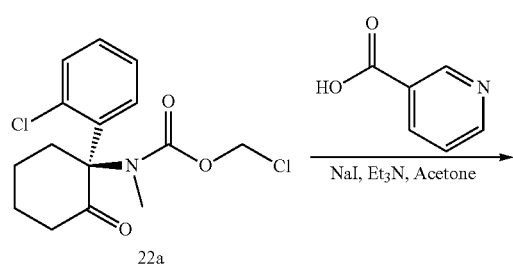

To a solution of 22a (82 mg, 0.25 mmol), NaI (75 mg, 0.5 mmol) and nicotinic acid (92 mg, 0.75 mmol) in acetone (3 mL) was added triethylamine (0.18 mL, 1.25 mmol). The reaction was heated to 70° C. for 2 h. The reaction was concentrated and re-dissolved in DCM (5 mL), washed with NaHCl$_{3(sat)}$ (5 mL) and brine (5 mL). The organic layer was dried over MgSO$_4$, filtered and concentrated to provide an oil, which was purified on silica gel column eluting with Hexane/EA (3/2) to afford 32 mg (31% yield) of the title compound 29 as a white solid. $^1$H NMR (600 MHz, acetone-d$_6$): δ 1.66-1.87 (m, 3H), 1.97-2.20 (m, 1H), 2.36-2.55 (m, 2H), 2.67-2.75 (m, 1H), 3.07 (s, 3H), 3.20-3.32 (m, 1H), 5.86-6.18 (m, 2H), 7.07-7.13 (m, 1H), 7.21-7.32 (m, 2H), 7.40-7.46 (m, 1H), 7.56-7.62 (m, 1H), 8.30-8.39 (m, 1H), 8.82-8.89 (m, 1H), 9.12-9.20 (m, 1H). LCMS (ESI): m/z calculated for [C$_{21}$H$_{21}$ClN$_2$O$_5$+H]$^+$ 417.11, found 416.9 [M+H]$^+$.

Example 30

Synthesis of 2-(2-chlorophenyl)-2-(methyl(methyl-d3)amino)cyclohexan-1-one (30)

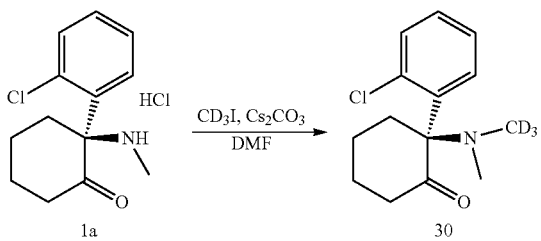

To a solution of S-ketamine hydrochloride 1a (68 mg, 0.25 mmol) and iodomethane-d$_3$ (109 mg, 0.75 mmol) and Cesium carbonate (163 mg, 0.5 mmol) in DMF (5 mL). The reaction was stirred at 25° C. for 4 h. The reaction was diluted with DCM (5 mL) and washed with water (5 mL) and brine (5 mL). The organic layer was dried over MgSO$_4$, filtered and concentrated to provide an oil, which was purified on silica gel column eluting with Hexane/EA (0 to 3/1) to afford 16 mg (23% yield) of the title compound 30 as a yellow solid. $^1$H NMR (500 MHz, methanol-d$_4$) δ 1.58-1.48 (m, 1H), 1.80-1.62 (m, 3H), 2.03-1.95 (m, 1H), 2.19 (s, 3H), 2.51-2.40 (m, 1H), 2.66-2.56 (m, 1H), 3.20-3.09 (m, 1H), 7.41-7.35 (m, 1H), 7.52-7.43 (m, 2H), 7.62-7.56 (m, 1H). LCMS (ESI): m/z calculated for [C$_{27}$H$_{31}$N$_3$O$_5$+H]$^+$ 255.12, found 255.00 [M+H]$^+$.

Example 31

Synthesis of (S)-(((1-(2-chlorophenyl)-2-oxocyclohexyl)(methyl)carbamoyl)oxy)methyl acetylglycinate (31)

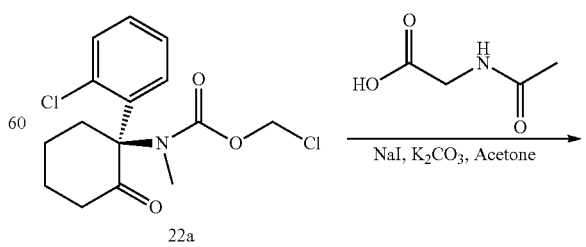

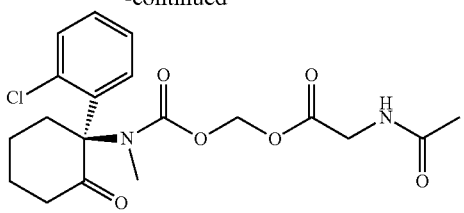

31

To a solution of 22a (50 mg, 0.15 mmol), NaI (45 mg, 0.30 mmol) and 2-acetamidoacetic acid (53.2 mg, 0.45 mmol) in acetone (2 mL) was added K$_2$CO$_3$ (105 mg, 0.76 mmol). The reaction was heated to 70° C. for 3 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/4) to afford 25 mg (40% yield) of the title compound 31 as a colorless gum. $^1$H NMR (600 MHz, DMSO-d$_6$): 1.61-1.77 (m, 3H), 1.87 (s, 3H), 1.95-2.00 (br, 1H), 2.29-2.37 (m, 2H), 2.54-2.63 (m, 1H), 2.96 (s, 3H), 3.08-3.17 (m, 1H), 3.81-3.90 (m, 2H), 5.62-5.78 (m, 2H), 6.93-6.98 (m, 1H), 7.29-7.38 (m, 2H), 7.44-7.48 (m, 1H), 8.36-8.43 (m, 1H). LCMS (ESI): m/z calculated for [C$_{19}$H$_{23}$ClN$_2$O$_6$+H]$^+$ 411.12, found 411.15 [M+H]$^+$.

Example 32

Synthesis of ((((S)-1-(2-chlorophenyl)-2-oxocyclohexyl)(methyl)carbamoyl)oxy)methylacetyl-L-valinate

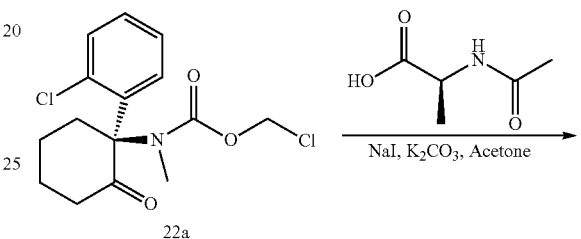

32

To a solution of 22a (50 mg, 0.15 mmol), NaI (45 mg, 0.30 mmol) and (S)-2-acetamido-3-methylbutanoic acid (72 mg, 0.45 mmol) in acetone (2 mL) was added K$_2$CO$_3$ (105 mg, 0.76 mmol). The reaction was heated to 70° C. for 3 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/4) to afford 65 mg (95% yield) of the title compound 32 as a white foam. $^1$H NMR (600 MHz, DMSO-d$_6$): 0.82-0.97 (m, 6H) 1.54-1.77 (br, 3H), 1.88 (s, 3H), 1.92-2.07 (br, 2H), 2.29-2.37 (m, 2H), 2.52-2.60 (m, 1H), 2.95 (s, 3H), 3.06-3.17 (m, 1H), 4.09-4.16 (m, 1H), 5.60-5.85 (m, 2H), 6.89-6.99 (m, 1H), 7.26-7.37 (m, 2H), 7.42-7.50 (m, 1H), 8.19-8.29 (m, 1H). LCMS (ESI): m/z calculated for [C$_{22}$H$_{29}$ClN$_2$O$_6$+H]$^+$ 453.17, found 453.12 [M+H]$^+$.

Example 33

Synthesis of ((((S)-1-(2-chlorophenyl)-2-oxocyclohexyl)(methyl)carbamoyl)oxy)methyl acetyl-L-alaninate (33)

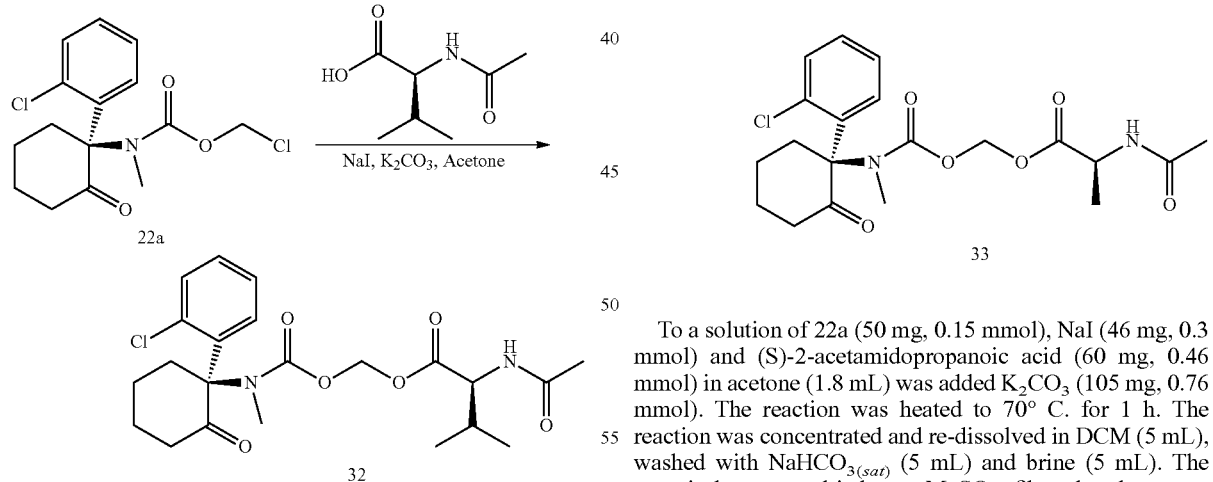

33

To a solution of 22a (50 mg, 0.15 mmol), NaI (46 mg, 0.3 mmol) and (S)-2-acetamidopropanoic acid (60 mg, 0.46 mmol) in acetone (1.8 mL) was added K$_2$CO$_3$ (105 mg, 0.76 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 13/7) to afford 52 mg (81% yield) of the title compound 33 as a white foam. $^1$H NMR (600 MHz, DMSO-d$_6$): δ 1.22-1.30 (m, 3H), 1.60-1.82 (m, 3H), 1.84 (s, 3H), 1.93-2.00 (m, 1H), 2.30-2.37 (m, 2H), 2.54-2.60 (m, 1H), 2.96 (s, 3H), 3.09-3.16 (m, 1H), 4.16-4.24 (m, 1H), 5.60-5.80 (m, 2H), 6.94-7.00 (m, 1H), 7.30-7.36 (m, 2H), 7.44-7.49 (m, 1H), 8.38 (d, J=6.00 Hz, 1H). LCMS (ESI): m/z calculated for [C$_{20}$H$_{25}$ClN$_2$O$_6$+H]$^+$ 425.14, found 424.8 [M+H]$^+$.

Example 34

Synthesis of (S)-(((1-(2-chlorophenyl)-2-oxocyclohexyl)(methyl)carbamoyl)oxy)methy isobutyrylglycinate (34)

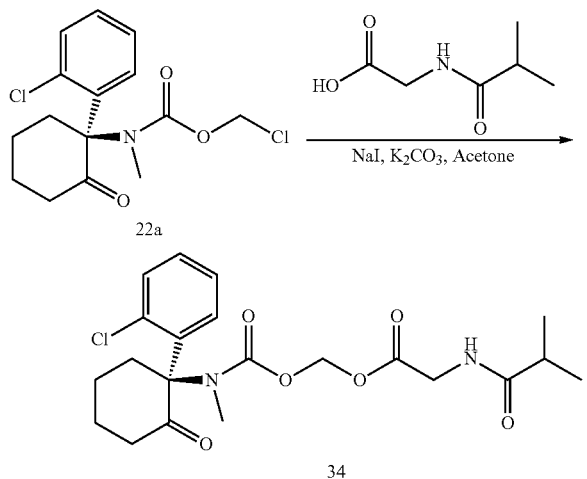

To a solution of 22a (50 mg, 0.15 mmol), NaI (46 mg, 0.3 mmol) and 2-(isobutyramido)acetic acid (66 mg, 0.46 mmol) in acetone (1.8 mL) was added K$_2$CO$_3$ (105 mg, 0.76 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/1) to afford 47 mg (70% yield) of the title compound 34 as a white foam. $^1$H NMR (600 MHz, DMSO-d$_6$): δ 1.01 (d, J=6.84 Hz, 6H), 1.62-1.76 (m, 3H), 1.94-2.01 (m, 1H), 2.29-2.38 (m, 2H), 2.39-2.46 (m, 1H), 2.55-2.63 (m, 1H), 2.99 (s, 3H), 3.08-3.16 (m, 1H), 3.85 (d, J=5.28 Hz, 2H), 5.60-5.80 (m, 2H), 6.94-6.98 (m, 1H), 7.30-7.37 (m, 2H), 7.44-7.48 (m, 1H), 8.27 (t, J=5.64 Hz, 1H). LCMS (ESI): m/z calculated for [C$_{21}$H$_{27}$ClN$_2$O$_6$+H]$^+$ 439.16, found 439.21 [M+H]$^+$.

Example 35

Synthesis of ((((S)-1-(2-chlorophenyl)-2-oxocyclohexyl)(methyl)carbamoyl)oxy)methyl isobutyryl-L-alaninate (35)

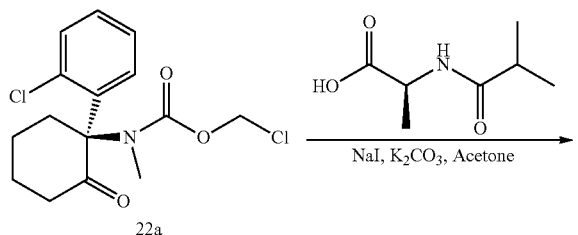

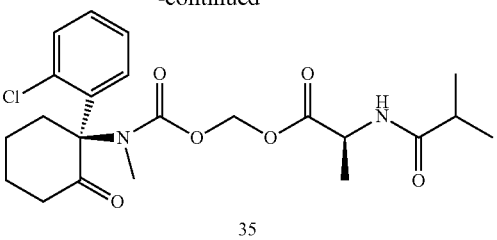

To a solution of 22a (50 mg, 0.15 mmol), NaI (45 mg, 0.30 mmol) and (S)-2-(isobutyramido)propanoic acid (72 mg, 0.45 mmol) in acetone (2 mL) was added K$_2$CO$_3$ (105 mg, 0.76 mmol). The reaction was heated to 70° C. for 4 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/2) to afford 30 mg (44% yield) of the title compound 35 as a white foam. $^1$H NMR (600 MHz, DMSO-d$_6$): 0.96-1.03 (m, 6H) 1.23-1.32 (br, 3H), 1.58-1.77 (m, 3H), 1.89-2.03 (br, 1H), 2.28-2.37 (m, 2H), 2.37-2.46 (m, 1H), 2.54-2.64 (m, 1H), 2.96 (s, 3H), 3.08-3.17 (m, 1H), 4.17-4.26 (m, 1H), 5.58-5.82 (m, 2H), 6.95-7.04 (m, 1H), 7.29-7.36 (m, 2H), 7.43-7.50 (m, 1H), 8.17-8.29 (m, 1H). LCMS (ESI): m/z calculated for [C$_{22}$H$_{29}$ClN$_2$O$_6$+H]$^+$ 453.17, found 453.02 [M+H]$^+$.

Example 36

Synthesis of ((((S)-1-(2-chlorophenyl)-2-oxocyclohexyl)(methyl)carbamoyl)oxy)methyl isobutyryl-L-valinate (36)

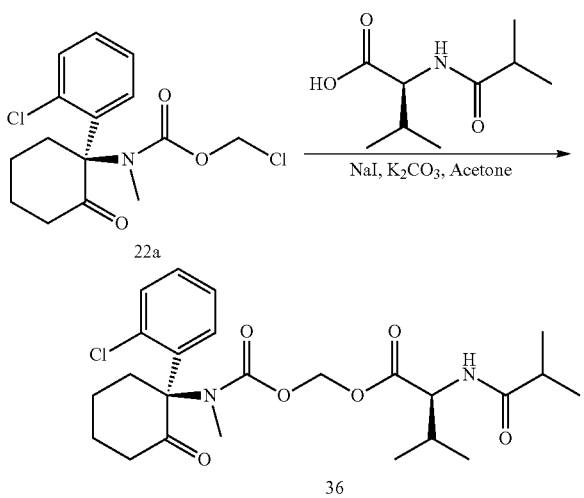

To a solution of 22a (50 mg, 0.15 mmol), NaI (46 mg, 0.3 mmol) and (S)-2-(isobutyramido)-3-methylbutanoic acid (102 mg, 0.46 mmol) in acetone (1.8 mL) was added K$_2$CO$_3$ (105 mg, 0.76 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 7/3) to afford 67 mg (93% yield) of the title compound 36 as a yellow foam. $^1$H NMR (600 MHz, DMSO-d$_6$): δ 0.85-0.94 (m, 6H), 0.96-1.02 (m, 6H), 1.55-1.65 (m, 1H), 1.66-1.76 (m, 2H), 1.92-1.99 (m, 1H), 2.00-2.08 (m, 1H), 2.31-2.40 (m, 2H), 2.52-2.60 (m, 2H), 2.95 (s, 3H), 3.08-3.17 (m, 1H), 4.14 (t, J=6.84 Hz, 1H), 5.60-5.88 (m, 2H), 6.95-7.00 (m, 1H), 7.30-7.36 (m, 2H), 7.44-7.49 (m, 1H), 8.12 (d, J=7.62 Hz, 1H). LCMS (ESI): m/z calculated for [C$_{24}$H$_{33}$ClN$_2$O$_6$+H]$^+$ 481.2, found 481.08 [M+H]$^+$.

Example 37

Synthesis of (((((S)-1-(2-chlorophenyl)-2-oxocyclohexyl)(methyl)carbamoyl)oxy)methyl L-valinate TFA salt (37)

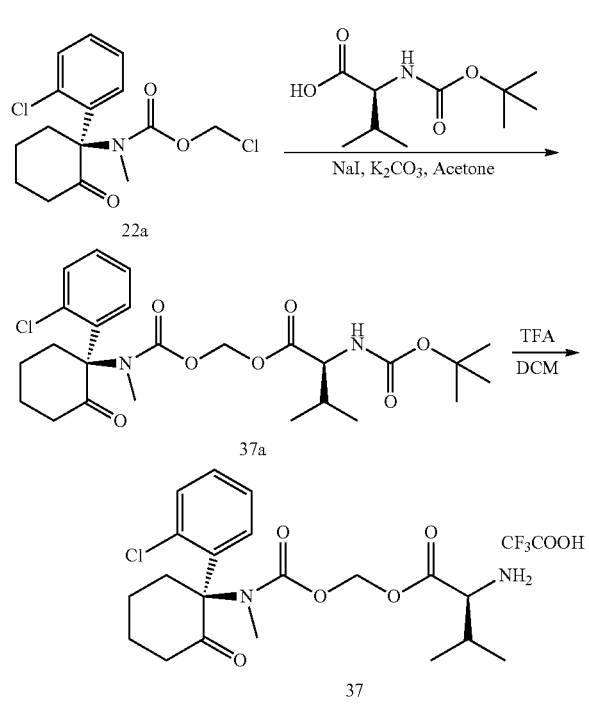 [SMILES: CN(C(=O)OCCl)[C@]1(c2ccccc2Cl)CCCCC1=O ; CC(C)[C@H](NC(=O)OC(C)(C)C)C(=O)O ; CC(C)[C@H](NC(=O)OC(C)(C)C)C(=O)OCOC(=O)N(C)[C@]1(c2ccccc2Cl)CCCCC1=O ; CC(C)[C@H](N)C(=O)OCOC(=O)N(C)[C@]1(c2ccccc2Cl)CCCCC1=O ; "CF3COOH"]

To a solution of 22a (150 mg, 0.46 mmol), NaI (137 mg, 0.9 mmol) and N-(tert-butoxycarbonyl)-L-valine (297 mg, 1.4 mmol) in acetone (5.4 mL) was added K$_2$CO$_3$ (315 mg, 2.3 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 191 mg (82% yield) of 37a as a white foam. $^1$H NMR (600 MHz, acetone-d$_6$): δ 0.94-1.02 (m, 6H), 1.40 (s, 9H), 1.72-1.87 (m, 3H), 2.00-2.03 (m, 1H), 2.11-2.19 (m, 1H), 2.39-2.51 (m, 2H), 2.65-2.72 (m, 1H), 3.05 (s, 3H), 3.23-3.32 (m, 1H), 4.07-4.12 (m, 1H), 5.70-5.94 (m, 2H), 6.31 (br, 1H), 7.05-7.12 (m, 1H), 7.28-7.36 (m, 2H), 7.43-7.48 (m, 1H). LCMS (ESI): m/z calculated for [C$_{25}$H$_{35}$ClN$_2$O$_7$+H]$^+$ 511.24, found 511.29 [M+H]$^+$.

To a solution of 37a (71 mg, 0.14 mmol) in DCM (5 mL) was added trifluoroacetic acid (0.19 mL, 2.5 mmol). The reaction was stirred at 25° C. for 16 h. The reaction was concentrated. Afford 67 mg of the title compound 37 as a colorless gum. $^1$H NMR (600 MHz, DMSO-d$_6$): δ 0.92-0.99 (m, 6H), 1.56-1.78 (m, 3H), 1.92-1.99 (m, 1H), 2.10-2.20 (m, 1H), 2.32-2.43 (m, 2H), 2.53-2.62 (m, 1H), 2.97 (s, 3H), 3.06-3.17 (m, 1H), 4.02-4.10 (m, 1H), 5.68-5.86 (m, 1H), 5.87-6.05 (m, 1H), 6.95-7.01 (m, 1H), 7.30-7.37 (m, 2H), 7.45-7.51 (m, 1H), 8.45 (br, 3H). LCMS (ESI): m/z calculated for [C$_{20}$H$_{27}$ClN$_2$O$_5$+H]$^+$ 411.16, found 411.19 [M+H]$^+$.

Example 38

Synthesis of (S)-(((1-(2-chlorophenyl)-2-oxocyclohexyl)(methyl)carbamoyl)oxy)methyl glycinate TFA salt (38)

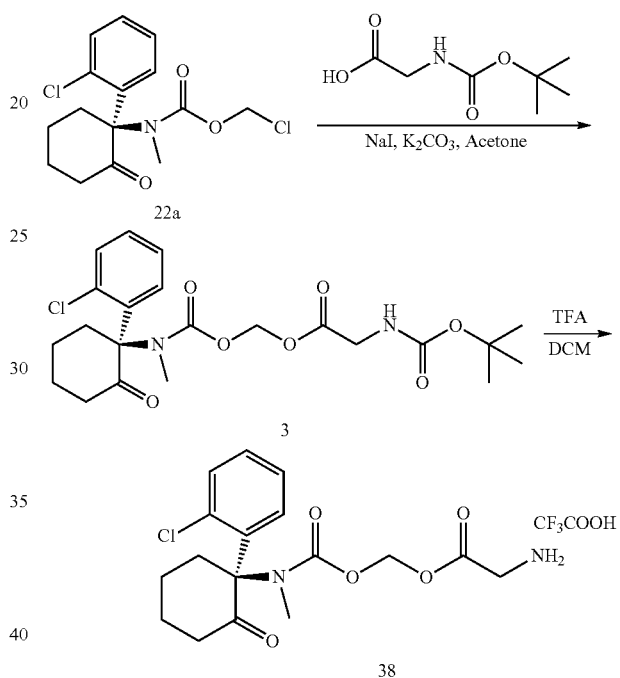

To a solution of 22a (50 mg, 0.15 mmol), NaI (46 mg, 0.3 mmol) and N-(tert-butoxycarbonyl)-L-glycine (102 mg, 0.46 mmol) in acetone (1.8 mL) was added K$_2$CO$_3$ (105 mg, 0.76 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 7/3) to afford 54 mg (76% yield) of 38a as a white foam. $^1$H NMR (600 MHz, acetone-d$_6$): δ 1.42 (s, 9H), 1.69-1.87 (m, 3H), 1.99-2.03 (m, 1H), 2.38-2.51 (m, 2H), 2.66-2.74 (m, 1H), 3.04 (s, 3H), 3.22-3.32 (m, 1H), 3.82-3.92 (m, 2H), 5.70-5.88 (m, 2H), 6.44 (br, 1H), 7.05-7.11 (m, 1H), 7.28-7.37 (m, 2H), 7.43-7.48 (m, 1H). LCMS (ESI): m/z calculated for [C$_{22}$H$_{29}$ClN$_2$O$_7$+H]$^+$ 469.17, found 469.10 [M+H]$^+$. To a solution of 38a (25 mg, 0.05 mmol) in DCM (1.9 mL) was added trifluoroacetic acid (0.07 mL, 0.96 mmol). The reaction was stirred at 25° C. for 16 h. The reaction was concentrated to afford 25 mg of the title compound 38 as a colorless gum. $^1$H NMR (500 MHz, DMSO-d$_6$): δ 1.60-1.80 (m, 3H), 1.92-2.01 (m, 1H), 2.33-2.43 (m, 2H), 2.54-2.65 (m, 1H), 2.98 (s, 3H), 3.08-3.17 (m, 1H), 3.92 (br, 2H), 5.72-5.92 (m, 2H), 6.96-7.02 (m, 1H), 7.30-7.38 (m, 2H), 7.45-7.51 (m, 1H), 8.31 (br, 3H). LCMS (ESI): m/z calculated for $[C_{17}H_{21}ClN_2O_5+H]^+$ 369.11, found 368.89 $[M+H]^+$.

Example 39

Synthesis of ((((S)-1-(2-chlorophenyl)-2-oxocyclohexyl)(methyl)carbamoyl)oxy)methyl dimethyl-L-valinate (39)

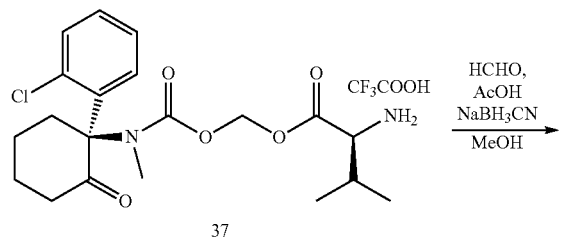

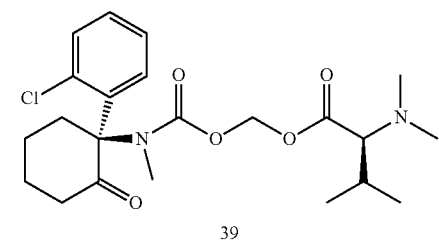

Compound 37 (52 mg, 0.1 mmol) was dissolved in MeOH (5.8 mL) and cooled to 0° C. in an ice bath. Acetic acid (0.02 mL, 0.4 mmol) and NaBH$_3$CN (13 mg, 0.2 mmol) was added to the above solution and stirred at 0° C. for 5 min. Formaldehyde (37% in H$_2$O, 0.02 mmol) was added at 0° C. and the reaction mixture was stirred at 25° C. for 2.5 h. The reaction was quenched with NaHCO$_3$ and diluted with water (5 mL). The aqueous layer was extracted with DCM (5 mL) and the organic layer was washed with brine (5 mL). The organic layer was dried over MgSO$_4$, filtered and concentrated to get a solid. The solid was washed with hexane and then recrystallized from DCM and hexane at 4° C. After 16 h, the mixture was filtered and collected the filtrate, concentrated to afford 20 mg (46% yield) of the title compound 39 as a white solid. $^1$H NMR (600 MHz, acetone-d$_6$): δ 0.89 (d, J=6.48 Hz, 3H), 0.97 (d, J=6.60 Hz, 3H), 1.72-1.87 (m, 3H), 1.96-2.03 (m, 2H), 2.30 (s, 6H), 2.40-2.46 (m, 1H), 2.46-2.53 (m, 1H), 2.66-2.73 (m, 1H), 2.74-2.78 (m, 1H), 3.04 (s, 3H), 3.22-3.29 (m, 1H), 5.80-5.90 (m, 2H), 7.05-7.09 (m, 1H), 7.27-7.34 (m, 2H), 7.44-7.48 (m, 1H). LCMS (ESI): m/z calculated for $[C_{22}H_{31}ClN_2O_5+H]^+$ 439.19, found 439.46 $[M+H]^+$.

Example 40

Synthesis of (S)-(((1-(2-chlorophenyl)-2-oxocyclohexyl)(methyl)carbamoyl)oxy)methyl N-acetyl-N-methylglycinate (40)

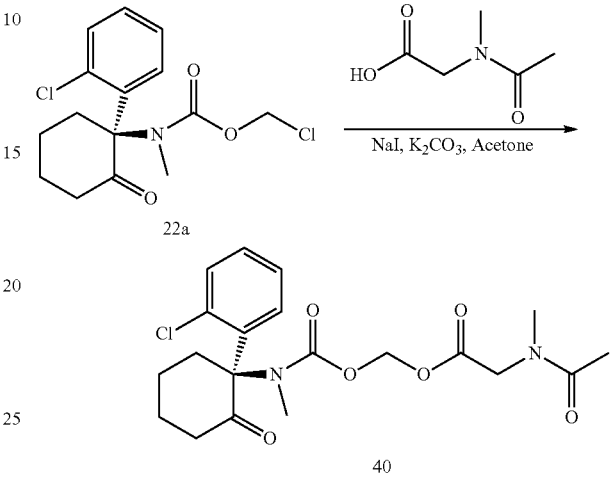

To a solution of 22A (50 mg, 0.15 mmol), NaI (45 mg, 0.30 mmol) and 2-(N-methylacetamido)acetic acid (99 mg, 0.76 mmol) in acetone (2 mL) was added K$_2$CO$_3$ (105 mg, 0.76 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/4) to afford 25 mg (39% yield) of the title compound 40 as a white foam. $^1$H NMR (600 MHz, DMSO-d$_6$): 1.61-1.76 (m, 3H) 1.89-2.01 (m, 2H), 2.01-2.05 (m, 2H), 2.30-2.40 (br, 2H), 2.54-2.73 (br, 2H), 2.80 (s, 1H), 2.96 (s, 3H), 3.03 (s, 2H), 3.08-3.18 (m, 1H), 4.06-4.37 (m, 2H), 5.61-5.86 (m, 2H), 6.93-7.00 (m, 1H), 7.29-7.38 (m, 2H), 7.43-7.50 (m, 1H). LCMS (ESI): m/z calculated for $[C_{20}H_{25}ClN_2O_6+H]^+$ 425.14, found 425.27 $[M+H]^+$.

Example 41

Synthesis of 1-((((S)-1-(2-chlorophenyl)-2-oxocyclohexyl)(methyl)carbamoyl)oxy)ethyl N-acetyl-N-methylglycinate (41)

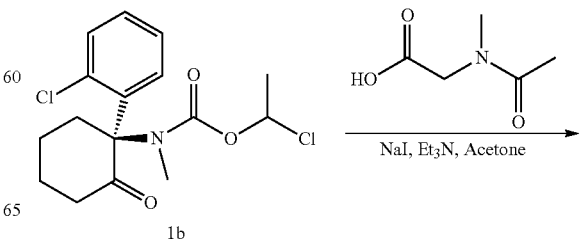

-continued

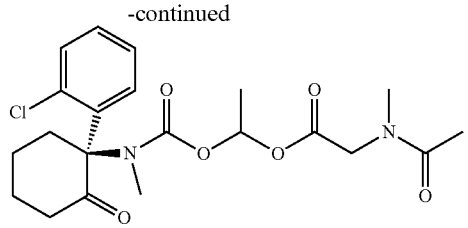

41

To a solution of 1b (50 mg, 0.15 mmol), NaI (43 mg, 0.29 mmol) and 2-(N-methylacetamido) acetic acid (95 mg, 0.73 mmol) in acetone (2 mL) was added triethylamine (0.10 mL, 0.73 mmol). The reaction was heated to 70° C. for 16 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/4) to afford 36 mg (57% yield) of the title compound 41 as a white foam. $^1$H NMR (600 MHz, DMSO-d$_6$): 1.29-1.59 (br, 3H) 1.59-1.78 (m, 3H), 1.81-1.90 (m, 1H), 1.94-2.07 (m, 3H), 2.25-2.42 (m, 2H), 2.53-2.68 (m, 1H), 2.78 (s, 1H), 2.92-3.03 (m, 5H), 3.06-3.19 (m, 1H), 3.99-4.29 (m, 2H), 6.61-6.72 (m, 1H), 6.91-7.02 (m, 1H), 7.28-7.37 (m, 2H), 7.43-7.50 (m, 1H). LCMS (ESI): m/z calculated for [C$_{21}$H$_{27}$ClN$_2$O$_6$+H]$^+$ 439.16, found 439.26 [M+H]$^+$.

Example 42

Synthesis of 1-((((S)-1-(2-chlorophenyl)-2-oxocyclohexyl)(methyl)carbamoyl)oxy)ethyl propionylglycinate (42)

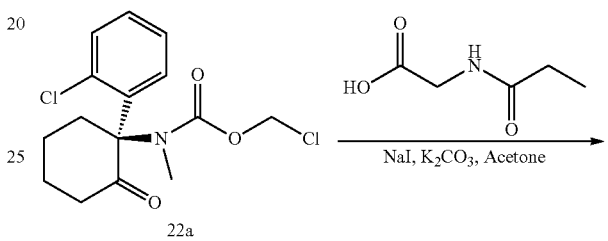

To a solution of 1b (50 mg, 0.145 mmol), NaI (23 mg, 0.15 mmol) and 2-(propionamido)acetic acid (57 mg, 0.435 mmol) in acetone (1.8 mL) was added triethylamine (0.1 mL, 0.725 mmol). The reaction was heated to 70° C. for 16 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/1) to afford 41 mg (65% yield) of the title compound 42 as a white foam.

$^1$H NMR (600 MHz, DMSO-d$_6$): δ 1.00 (t, J=7.62 Hz, 3H), 1.34-1.59 (m, 3H), 1.60-1.77 (m, 3H), 1.94-2.03 (m, 1H), 2.10-2.18 (m, 2H), 2.27-2.41 (m, 2H), 2.53-2.67 (m, 1H), 2.95 and 2.97 (two s, total 3H), 3.06-3.19 (m, 1H), 3.71-3.82 (m, 1H), 3.82-3.96 (m, 1H), 6.61-6.68 (m, 1H), 6.92-7.00 (m, 1H), 7.29-7.37 (m, 2H), 7.43-7.49 (m, 1H), 8.22-8.32 (m, 1H). LCMS (ESI): m/z calculated for [C$_{21}$H$_{27}$ClN$_2$O$_6$+H]$^+$ 439.16, found 439.23 [M+H]$^+$.

Example 43

Synthesis of (S)-(((1-(2-chlorophenyl)-2-oxocyclohexyl)(methyl)carbamoyl)oxy)methy propionylglycinate (43)

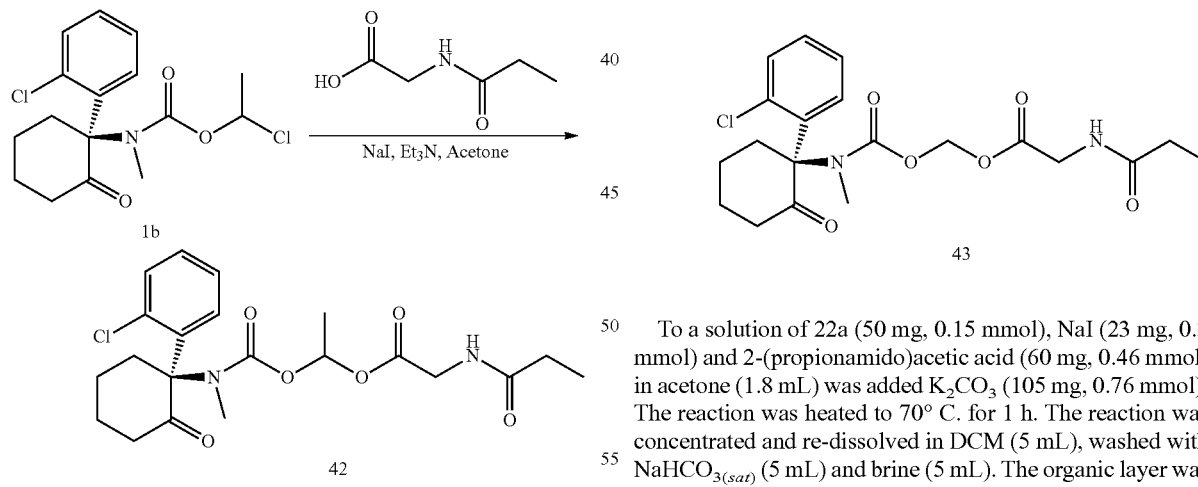

To a solution of 22a (50 mg, 0.15 mmol), NaI (23 mg, 0.3 mmol) and 2-(propionamido)acetic acid (60 mg, 0.46 mmol) in acetone (1.8 mL) was added K$_2$CO$_3$ (105 mg, 0.76 mmol). The reaction was heated to 70° C. for 1 h. The reaction was concentrated and re-dissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 2/3) to afford 45 mg (69% yield) of the title compound 43 as a white foam. $^1$H NMR (600 MHz, DMSO-d$_6$): δ 1.00 (t, J=7.62 Hz, 3H), 1.62-1.78 (m, 3H), 1.97-2.04 (m, 1H), 2.15 (q, J=7.56 Hz, 2H), 2.30-2.39 (m, 2H), 2.55-2.63 (m, 1H), 2.96 (s, 3H), 3.08-3.16 (m, 1H), 3.80-3.92 (m, 2H), 5.60-5.80 (m, 2H), 6.93-6.99 (m, 1H), 7.30-7.38 (m, 2H), 7.44-7.49 (m, 1H), 8.30 (t, J=5.46 Hz, 1H). LCMS (ESI): m/z calculated for [C$_{20}$H$_{25}$ClN$_2$O$_6$+H]$^+$ 425.14, found 425.38 [M+H]$^+$.

Example 44

Synthesis of (((((S)-1-(2-chlorophenyl)-2-oxocyclohexyl)(methyl)carbamoyl)oxy)methyl L-alaninate TFA salt (44)

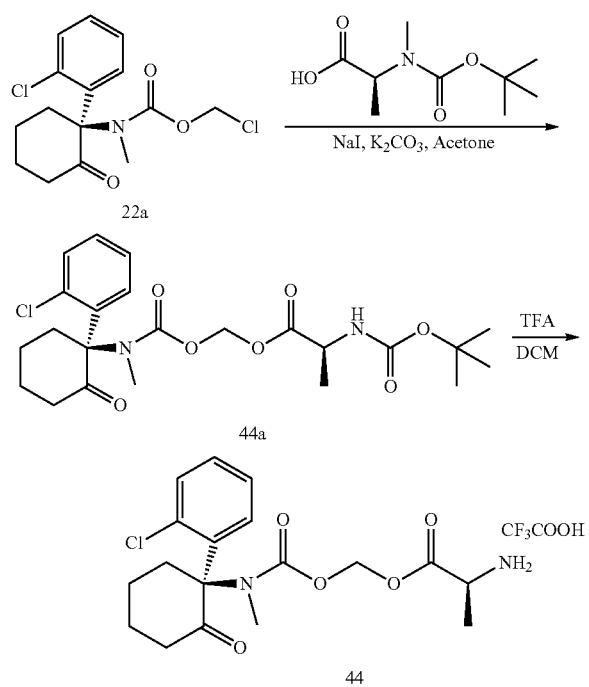 [SMILES: CN(C(=O)OCCl)[C@]1(c2ccccc2Cl)CCCCC1=O ; C[C@@H](C(=O)O)N(C)C(=O)OC(C)(C)C ; C[C@H](NC(=O)OC(C)(C)C)C(=O)OCOC(=O)N(C)[C@]1(c2ccccc2Cl)CCCCC1=O ; C[C@H](N)C(=O)OCOC(=O)N(C)[C@]1(c2ccccc2Cl)CCCCC1=O ; "CF3COOH"]

To a solution of 22a (150 mg, 0.45 mmol), NaI (136 mg, 0.91 mmol) and (2S)-2-({[(2-methyl-2-propanyl)oxy]carbonyl}amino)propanoic acid (258 mg, 1.36 mmol) in acetone (5 mL) was added $K_2CO_3$ (314 mg, 2.27 mmol). The reaction was heated to 70° C. for 1 h. The reaction was concentrated and re-dissolved in DCM (10 mL), washed with $NaHCO_{3(sat)}$ (10 mL) and brine (10 mL). The organic layer was dried over $MgSO_4$, filtered and concentrated to provide an oil, which was purified on silica gel column eluting with Hexane/EA (1/0 to 3/2) to afford 200 mg (91% yield) of 10 as a white foam. $^1$H NMR (500 MHz, DMSO-$d_6$): 1.19-1.28 (m, 3H) 1.28-1.46 (m, 9H), 1.57-1.79 (m, 3H), 1.93-2.02 (m, 1H), 2.28-2.42 (m, 2H), 2.54-2.62 (m, 1H), 2.96 (s, 3H), 3.07-3.19 (m, 1H), 3.97-4.08 (m, 1H), 5.60-5.84 (m, 2H), 6.92-7.05 (m, 1H), 7.29-7.37 (m, 2H), 7.37-7.44 (m, 1H), 7.44-7.51 (m, 1H). LCMS (ESI): m/z calculated for $[C_{23}H_{31}ClN_2O_7+H]^+$ 483.18, found 483.33 $[M+H]^+$.

To a solution of 44a (200 mg, 0.41 mmol) in DCM (15 mL) was added trifluoroacetic acid (0.57 mL, 7.5 mmol). The reaction was stirred at 25° C. for 16 h. The reaction was concentrated to afford 250 mg of the title compound 44 as a colorless gum. $^1$H NMR (600 MHz, DMSO-$d_6$): 1.29-1.43 (m, 3H) 1.58-1.79 (m, 3H), 1.90-2.02 (m, 1H), 2.31-2.43 (m, 2H), 2.54-2.62 (m, 1H), 2.98 (s, 3H), 3.07-3.17 (m, 1H), 4.12-4.26 (m, 1H), 5.65-5.98 (m, 2H), 6.93-7.02 (m, 1H), 7.28-7.38 (m, 2H), 7.43-7.51 (m, 1H), 8.26-8.48 (m, 3H). LCMS (ESI): m/z calculated for $[C_8H_{23}ClN_2O_5+H]^+$ 383.13, found 383.63 $[M+H]^+$.

Example 45

Synthesis of 1-(((((S)-1-(2-chlorophenyl)-2-oxocyclohexyl)(methyl)carbamoyl)oxy)ethyl (2,2,2-trifluoroacetyl)glycinate (45)

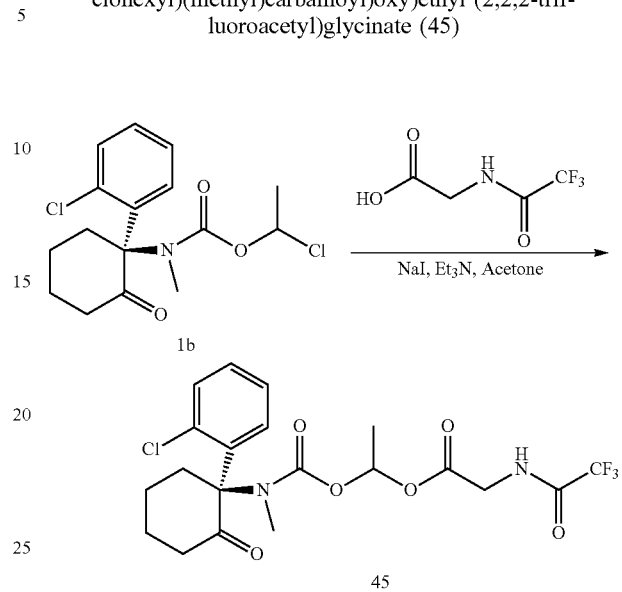

To a solution of 1b (103 mg, 0.3 mmol), NaI (47 mg, 0.315 mmol) and 2-(2,2,2-trifluoroacetamido)-acetic acid (154 mg, 0.9 mmol) in acetone (4 mL) was added triethylamine (0.21 mL, 1.5 mmol). The reaction was heated to 70° C. for 16 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 3/1) to afford 113 mg (79% yield) of the title compound 45 as a white solid. $^1$H NMR (500 MHz, DMSO-$d_6$): δ 1.37-1.58 (m, 3H), 1.60-1.78 (m, 3H), 1.94-2.03 (m, 1H), 2.28-2.40 (m, 2H), 2.53-2.68 (m, 1H), 2.95 and 2.97 (two s, total 3H), 3.06-3.20 (m, 1H), 3.90-3.99 (m, 1H), 4.00-4.16 (m, 1H), 6.65-6.72 (m, 1H), 6.93-7.01 (m, 1H), 7.27-7.36 (m, 2H), 7.44-7.49 (m, 1H), 9.99 (t, J=5.80 Hz, 1H). LCMS (ESI): m/z calculated for $[C_{20}H_{22}ClF_3N_2O_6+H]^+$ 479.11, found 479.11 $[M+H]^+$.

Example 46

Synthesis of (S)-(((1-(2-chlorophenyl)-2-oxocyclohexyl)(methyl)carbamoyl)oxy)methyl (2,2,2-trifluoroacetyl)glycinate (46)

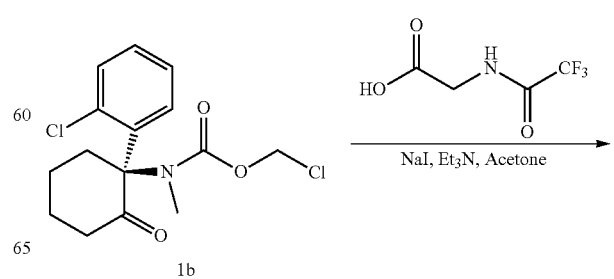

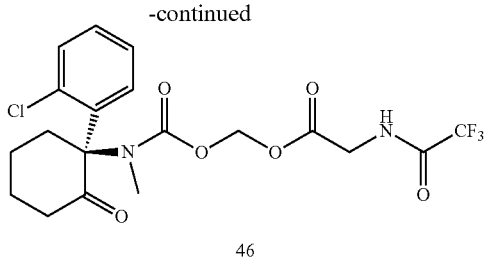

46

To a solution of 1b (50 mg, 0.15 mmol), NaI (46 mg, 0.3 mmol) and 2-(2,2,2-trifluoroacetamido)-acetic acid (78 mg, 0.46 mmol) in acetone (4 mL) was added triethylamine (0.1 mL, 0.76 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 7/3) to afford 14 mg (20% yield) of the title compound 46 as a white solid. $^1$H NMR (600 MHz, DMSO-d$_6$): δ 1.60-1.78 (m, 3H), 1.92-2.01 (m, 1H), 2.30-2.39 (m, 2H), 2.55-2.63 (m, 1H), 2.97 (s, 3H), 3.08-3.17 (m, 1H), 4.07 (t, J=4.86 Hz, 2H), 5.64-5.86 (m, 2H), 6.93-6.99 (m, 1H), 7.30-7.36 (m, 2H), 7.44-7.49 (m, 1H), 10.04 (t, J=5.40 Hz, 1H). LCMS (ESI): m/z calculated for [C$_{19}$H$_{20}$CF$_3$N$_2$O$_6$+H]$^+$ 465.1, found 465.56 [M+H]$^+$.

Example 47

Synthesis of 1-(((((S)-1-(2-chlorophenyl)-2-oxocyclohexyl)(methyl)carbamoyl)oxy)ethyl dimethyl-L-alaninate (47)

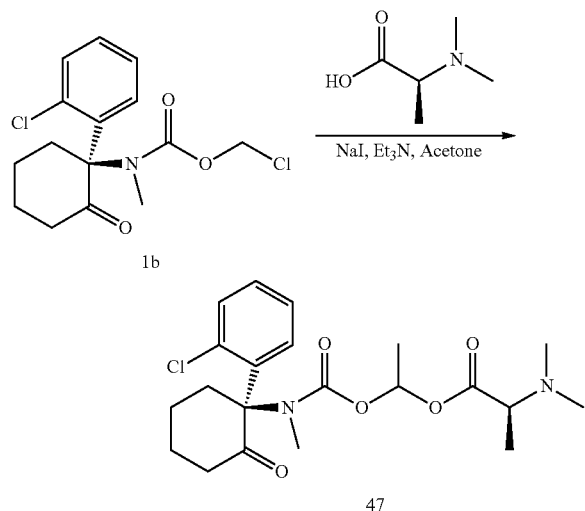

To a solution of 1b (31 mg, 0.09 mmol), NaI (27 mg, 0.18 mmol) and (S)-2-(dimethylamino)-propanoic acid (32 mg, 0.27 mmol) in acetone (1 mL) was added triethylamine (0.06 mL, 0.45 mmol). The reaction was heated to 70° C. for 20 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/3) to afford 14 mg (37% yield) of the title compound 47 as a yellow gum. $^1$H NMR (600 MHz, DMSO-d$_6$): δ 1.14 (d, J=7.08 Hz, 3H), 1.37-1.58 (m, 3H), 1.60-1.77 (m, 3H), 1.95-2.03 (m, 1H), 2.14-2.26 (m, 6H), 2.28-2.36 (m, 2H), 2.56-2.70 (m, 1H), 2.96 and 2.97 (two s, total 3H), 3.05-3.19 (m, 1H), 3.20-3.28 (m, 1H), 6.62-6.70 (m, 1H), 6.93-7.02 (m, 1H), 7.26-7.36 (m, 2H), 7.44-7.49 (m, 1H). LCMS (ESI): m/z calculated for [C$_{21}$H$_{29}$ClN$_2$O$_5$+H]$^+$ 425.18, found 425.49 [M+H]$^+$.

Example 48

Synthesis of (((((S)-1-(2-chlorophenyl)-2-oxocyclohexyl)(methyl)carbamoyl)oxy)methyl (2,2,2-trifluoroacetyl)-L-valinate (48)

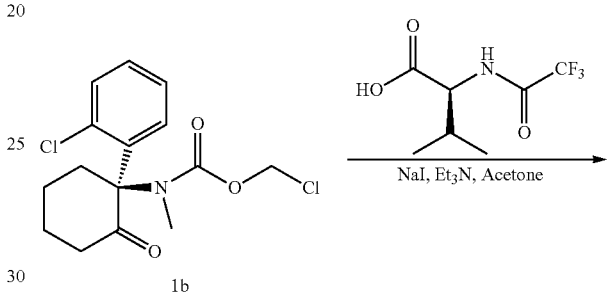

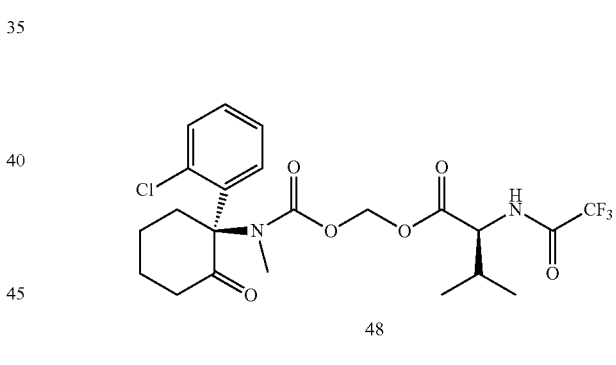

48

To a solution of 22b (50 mg, 0.15 mmol), NaI (45 mg, 0.30 mmol) and (S)-2-(2,2,2-trifluoroacetamido)-3-methylbutanoic acid (97 mg, 0.45 mmol) in acetone (2 mL) was added triethylamine (0.11 mL, 0.76 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 34 mg (44% yield) of the title compound 1b 48 as a white gum. $^1$H NMR (500 MHz, DMSO-d$_6$): 0.88-0.99 (m, 6H) 1.56-1.78 (m, 3H), 1.89-2.00 (m, 1H), 2.13-2.26 (m, 1H), 2.30-2.42 (m, 2H), 2.52-2.62 (m, 1H), 2.95 (s, 3H), 3.07-3.18 (m, 1H), 4.17-4.29 (m, 1H), 5.70-5.88 (m, 2H), 6.92-7.01 (m, 1H), 7.28-7.38 (m, 2H), 7.43-7.50 (m, 1H), 9.84-9.93 (m, 2H). LCMS (ESI): m/z calculated for [C$_{22}$H$_{26}$CF$_3$N$_2$O$_6$+H]$^+$ 507.14, found 507.46 [M+H]$^+$.

Example 49

Synthesis of 1-((((S)-1-(2-chlorophenyl)-2-oxocyclohexyl)(methyl)carbamoyl)oxy)propyl (2,2,2-trifluoroacetyl)glycinate (49)

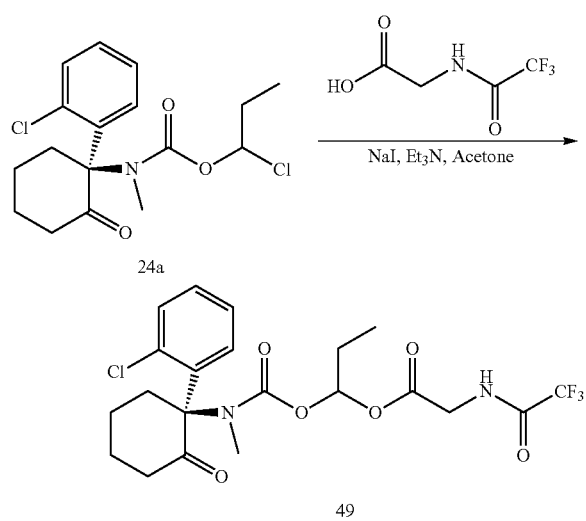

To a solution of 24a (50 mg, 0.14 mmol), NaI (22 mg, 0.15 mmol) and 2-(2,2,2-trifluoroacetamido)-acetic acid (72 mg, 0.42 mmol) in acetone (1.8 mL) was added triethylamine (0.1 mL, 0.7 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/1) to afford 28 mg (41% yield) of the title compound 49 as a white foam. $^1$H NMR (500 MHz, DMSO-d$_6$): δ 0.80-1.02 (m, 3H), 1.58-1.92 (m, 5H), 1.93-2.04 (m, 1H), 2.27-2.41 (m, 2H), 2.53-2.70 (m, 1H), 2.95 and 2.98 (two s, total 3H), 3.04-3.20 (m, 1H), 3.92-4.02 (m, 1H), 4.03-4.16 (m, 1H), 6.57 (q, J=5.65 Hz, 1H), 6.93-7.00 (m, 1H), 7.26-7.36 (m, 2H), 7.43-7.50 (m, 1H), 9.93-10.06 (m, 1H). LCMS (ESI): m/z calculated for [C$_{21}$H$_{24}$ClF$_3$N$_2$O$_6$+H]$^+$ 493.13, found 493.42 [M+H]$^+$.

Example 50

Synthesis of (((((S)-1-(2-chlorophenyl)-2-oxocyclohexyl)(methyl)carbamoyl)oxy)methyl (2,2,2-trifluoroacetyl)-L-alaninate (50)

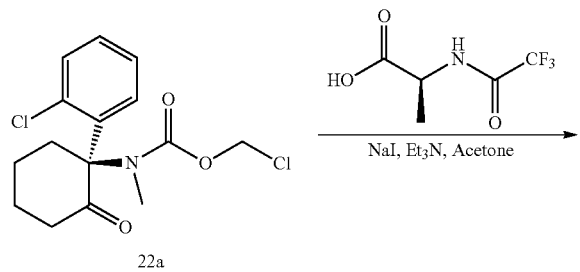

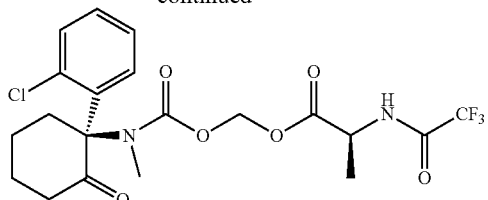

To a solution of 22a (50 mg, 0.15 mmol), NaI (45 mg, 0.30 mmol) and (S)-2-(2,2,2-trifluoro-acetamido)propanoic acid (84 mg, 0.45 mmol) in acetone (2 mL) was added triethylamine (0.11 mL, 0.76 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 13 mg (18% yield) of the title compound 50 as a white solid. $^1$H NMR (500 MHz, DMSO-d$_6$): 1.34-1.45 (m, 3H), 1.59-1.78 (m, 3H), 1.92-2.01 (m, 1H), 2.30-2.41 (m, 2H), 2.52-2.62 (m, 1H), 2.96 (s, 3H), 3.07-3.18 (m, 1H), 4.40-4.49 (m, 1H), 5.66-5.86 (m, 2H), 6.92-7.01 (m, 1H), 7.28-7.38 (m, 2H), 7.43-7.50 (m, 1H), 9.91-10.02 (m, 1H). LCMS (ESI): m/z calculated for [C$_{20}$H$_{22}$CF$_3$N$_2$O$_6$+H]$^+$ 479.11, found 479.23 [M+H]$^+$.

Example 51

Synthesis of 1-((((S)-1-(2-chlorophenyl)-2-oxocyclohexyl)(methyl)carbamoyl)oxy)-2-methylpropy (2,2,2-trifluoroacetyl)glycinate (51)

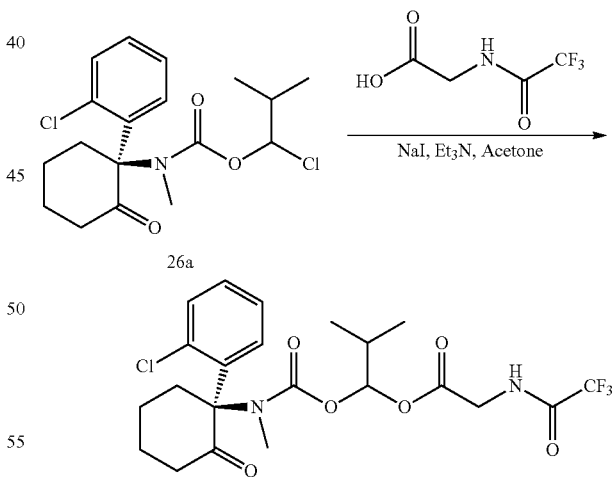

To a solution of 26a (93 mg, 0.25 mmol), NaI (39 mg, 0.26 mmol) and 2-(2,2,2-trifluoro-acetamido)acetic acid (128 mg, 0.75 mmol) in acetone (3 mL) was added triethylamine (0.17 mL, 1.25 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/1) to afford 51 mg (40% yield) of the title compound 51 as a white foam. $^1$H NMR (500 MHz, DMSO-d$_6$): δ 0.80-1.08 (m, 6H), 1.60-1.78 (m, 3H), 1.93-2.15 (m, 2H), 2.28-2.41 (m, 2H), 2.64-2.72 (m, 1H), 2.96 and 2.99 (two s, total 3H), 3.03-3.21 (m, 1H), 3.92-4.03 (m, 1H), 4.03-4.18 (m, 1H), 6.45 (d, J=4.95 Hz, 1H), 6.92-6.99 (m, 1H), 7.27-7.36 (m, 2H), 7.44-7.49 (m, 1H), 10.01 (br, 1H). LCMS (ESI): m/z calculated for [C$_{22}$H$_{26}$CF$_3$N$_2$O$_6$+H]$^+$ 507.14, found 507.4 [M+H]$^+$.

Example 52

Synthesis of 1-((((S)-1-(2-chlorophenyl)-2-oxocyclohexyl)(methyl)carbamoyl)oxy)ethyl (2,2,2-trifluoroacetyl)-L-valinate (52)

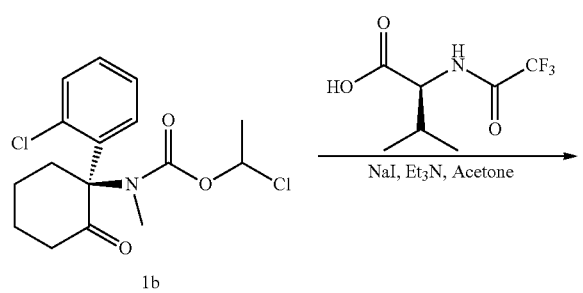

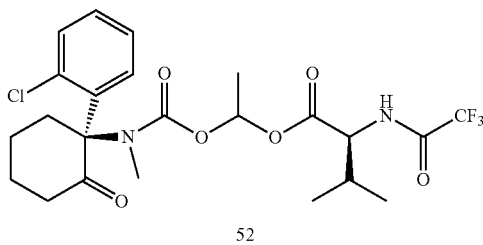

To a solution of 1b (103 mg, 0.3 mmol), NaI (47 mg, 0.315 mmol) and (S)-2-(2,2,2-trifluoro-acetamido)-3-methylbutanoic acid (192 mg, 0.9 mmol) in acetone (4 mL) was added triethylamine (0.21 mL, 1.5 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 17/3) to afford 128 mg (82% yield) of the title compound 45 as a white foam. $^1$H NMR (500 MHz, DMSO-d$_6$): δ 0.82-0.99 (m, 6H), 1.38-1.55 (m, 3H), 1.56-1.78 (m, 3H), 1.91-2.00 (m, 1H), 2.10-2.20 (m, 1H), 2.26-2.39 (m, 2H), 2.58-2.69 (m, 1H), 2.94 and 2.97 (two s, total 3H), 3.05-3.16 (m, 1H), 4.12 (t, J=7.60 Hz, 1H), 6.72 (q, J=5.45 Hz, 1H), 6.91-7.01 (m, 1H), 7.27-7.36 (m, 2H), 7.43-7.48 (m, 1H), 9.76-9.88 (m, 1H). LCMS (ESI): m/z calculated for [C$_{23}$H$_{28}$CF$_3$N$_2$O$_6$+H]$^+$ 521.16, found 521.46 [M+H]$^+$.

Example 53

Synthesis of 1-((((S)-1-(2-chlorophenyl)-2-oxocyclohexyl)(methyl)carbamoyl)oxy)ethyl (2,2,2-trifluoroacetyl)-L-alaninate (53)

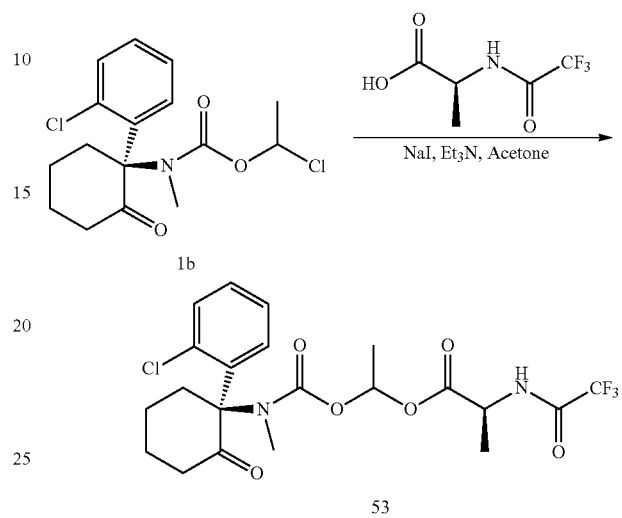

To a solution of 1b (103 mg, 0.3 mmol), NaI (47 mg, 0.315 mmol) and (S)-2-(2,2,2-trifluoro-acetamido)propanoic acid (167 mg, 0.9 mmol) in acetone (4 mL) was added triethylamine (0.21 mL, 1.5 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 81 mg (55% yield) of the title compound 45 as a white foam. $^1$H NMR (500 MHz, DMSO-d$_6$): δ1.32 (d, J=7.30 Hz, 3H), 1.40-1.58 (m, 3H), 1.62-1.78 (m, 3H), 1.95-2.03 (m, 1H), 2.28-2.39 (m, 2H), 2.55-2.65 (m, 1H), 2.97 and 2.98 (two s, total 3H), 3.10-3.19 (m, 1H), 4.38-4.47 (m, 1H), 6.66 (q, J=5.45 Hz, 1H), 6.91-7.00 (m, 1H), 7.28-7.36 (m, 2H), 7.44-7.50 (m, 1H), 9.90 (d, J=6.90 Hz, 1H). LCMS (ESI): m/z calculated for [C$_{21}$H$_{24}$CF$_3$N$_2$O$_6$+H]$^+$ 493.13, found 493.41 [M+H]$^+$.

Example 54

Synthesis of (S)-(((1-(2-chlorophenyl)-2-oxocyclohexyl)(methyl)carbamoyl)oxy)methyl 4-methylnicotinate (54)

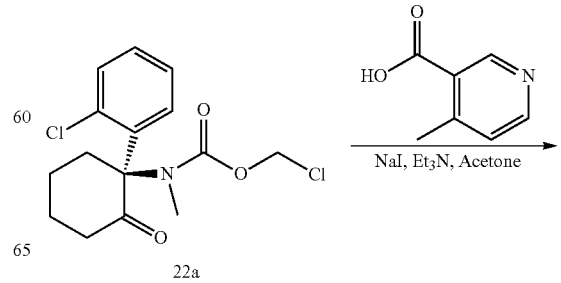

-continued

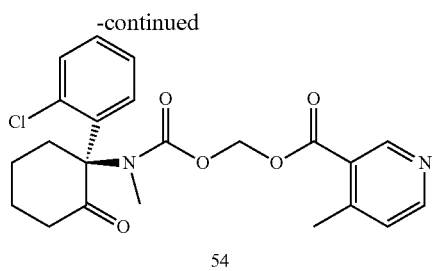

54

To a solution of 22a (100 mg, 0.3 mmol), NaI (90 mg, 0.6 mmol) and 4-methylpyridine-3-carboxylic acid (123 mg, 0.9 mmol) in acetone (4 mL) was added triethylamine (0.21 mL, 1.5 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/2) to afford 45 mg (35% yield) of the title compound 54 as a white solid. $^1$H NMR (600 MHz, DMSO-d$_6$): δ 1.62-1.77 (m, 3H), 1.92-2.00 (m, 1H), 2.31-2.40 (m, 2H), 2.55 (s, 3H), 2.58-2.66 (m, 1H), 3.00 (s, 3H), 3.08-3.16 (m, 1H), 5.80-6.12 (m, 2H), 6.98-7.02 (m, 1H), 7.22-7.27 (m, 1H), 7.28-7.34 (m, 1H), 7.41-7.44 (m, 1H), 7.45-7.48 (m, 1H), 8.64 (d, J=5.04 Hz, 1H), 8.92 (s, 1H). LCMS (ESI): m/z calculated for [C$_{22}$H$_{23}$ClN$_2$O$_5$+H]$^+$ 431.13, found 431.11 [M+H]$^+$.

Example 55

Synthesis of (S)-(((1-(2-chlorophenyl)-2-oxocyclohexyl)(methyl)carbamoyl)oxy)methyl 2-methylnicotinate (55)

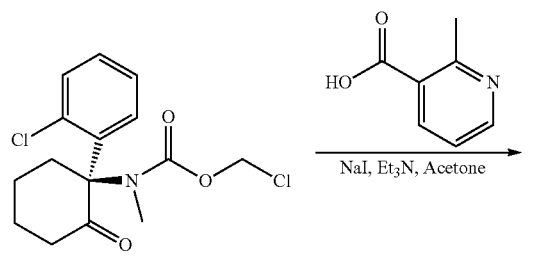

22a

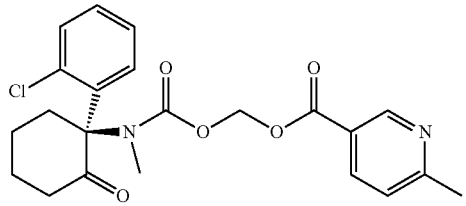

55

To a solution of 22a (100 mg, 0.3 mmol), NaI (90 mg, 0.6 mmol) and 2-methylpyridine-3-carboxylic acid (123 mg, 0.9 mmol) in acetone (4 mL) was added triethylamine (0.21 mL, 1.5 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/2) to afford 56 mg (43% yield) of the title compound 55 as a white foam. $^1$H NMR (600 MHz, DMSO-d$_6$): δ 1.62-1.77 (m, 3H), 1.92-1.99 (m, 1H), 2.31-2.40 (m, 2H), 2.57-2.65 (m, 1H), 2.72 (s, 3H), 3.00 (s, 3H), 3.07-3.16 (m, 1H), 5.80-6.08 (m, 2H), 6.97-7.02 (m, 1H), 7.22-7.27 (m, 1H), 7.28-7.34 (m, 1H), 7.40-7.48 (m, 2H), 8.12-8.22 (m, 1H), 8.65-8.70 (m, 1H). LCMS (ESI): m/z calculated for [C$_{22}$H$_{23}$ClN$_2$O$_5$+H]$^+$ 431.13, found 431.11 [M+H]$^+$.

Example 56

Synthesis of (S)-(((1-(2-chlorophenyl)-2-oxocyclohexyl)(methyl)carbamoyl)oxy)methyl 6-methylnicotinate (56)

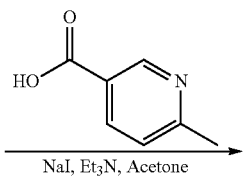

22a

56

To a solution of 22a (100 mg, 0.3 mmol), NaI (90 mg, 0.6 mmol) and 6-methylpyridine-3-carboxylic acid (123 mg, 0.9 mmol) in acetone (4 mL) was added triethylamine (0.21 mL, 1.5 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/2) to afford 44 mg (34% yield) of the title compound 56 as a white foam. $^1$H NMR (600 MHz, DMSO-d$_6$): δ 1.61-1.76 (m, 3H), 1.92-1.99 (m, 1H), 2.30-2.40 (m, 2H), 2.55-2.63 (m, 1H), 2.58 (s, 3H), 2.99 (s, 3H), 3.05-3.15 (m, 1H), 5.82-6.08 (m, 2H), 6.96-7.01 (m, 1H), 7.21-7.27 (m, 1H), 7.28-7.34 (m, 1H), 7.42-7.49 (m, 2H), 8.12-8.24 (m, 1H), 8.97 (s, 1H). LCMS (ESI): m/z calculated for [C$_{22}$H$_{23}$ClN$_2$O$_5$+H]$^+$ 431.13, found 431.09 [M+H]$^+$.

Example 57

Synthesis of 1-((((S)-1-(2-chlorophenyl)-2-oxocyclohexyl)(methyl)carbamoyl)oxy)ethyl acetyl-L-leucinate (57)

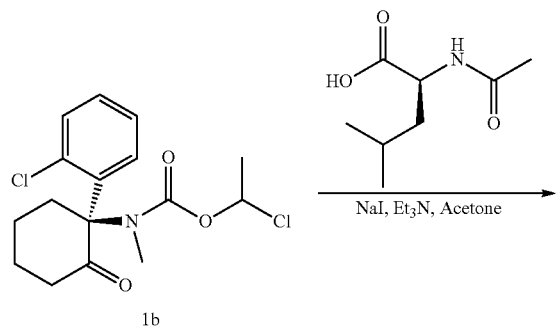

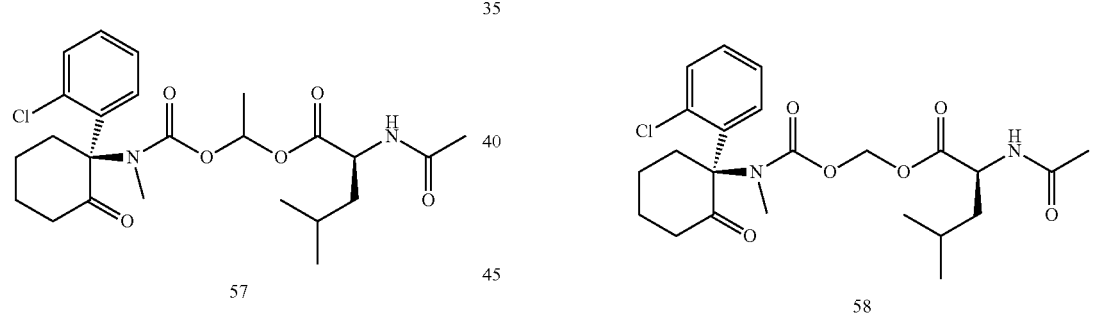

To a solution of 1b (103 mg, 0.3 mmol), NaI (47 mg, 0.315 mmol) and (S)-2-acetamido-4-methylpentanoic acid (156 mg, 0.9 mmol) in acetone (4 mL) was added triethylamine (0.21 mL, 1.5 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 11/9) to afford 102 mg (71% yield) of the title compound 57 as a white foam. $^1$H NMR (600 MHz, DMSO-d$_6$): δ 0.79-0.91 (m, 6H), 1.36-1.77 (m, 9H), 1.84 (s, 3H), 1.94-2.01 (m, 1H), 2.27-2.38 (m, 2H), 2.56-2.70 (m, 1H), 2.95 and 2.96 (two s, total 3H), 3.06-3.16 (m, 1H), 4.14-4.25 (m, 1H), 6.60-6.67 (m, 1H), 6.92-6.98 (m, 1H), 7.29-7.36 (m, 2H), 7.44-7.49 (m, 1H), 8.26 (d, J=7.56 Hz, 1H). LCMS (ESI): m/z calculated for [C$_{24}$H$_{33}$ClN$_2$O$_6$+H]$^+$ 481.2, found 481.1 [M+H]$^+$.

Example 58

Synthesis of (((((S)-1-(2-chlorophenyl)-2-oxocyclohexyl)(methyl)carbamoyl)oxy)methyl acetyl-L-leucinate (58)

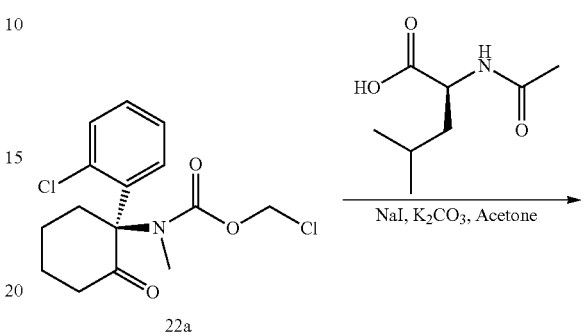

To a solution of 22a (100 mg, 0.3 mmol), NaI (90 mg, 0.6 mmol) and (S)-2-acetamido-4-methylpentanoic acid (156 mg, 0.9 mmol) in acetone (4 mL) was added K$_2$CO$_3$ (207 mg, 1.5 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 3/2) to afford 120 mg (86% yield) of the title compound 1b 58 as a white foam. $^1$H NMR (500 MHz, DMSO-d$_6$): δ 0.85 (d, J=6.55 Hz, 3H), 0.89 (d, J=6.60 Hz, 3H), 1.40-1.59 (m, 2H), 1.60-1.79 (m, 4H), 1.86 (s, 3H), 1.93-2.00 (m, 1H), 2.31-2.40 (m, 2H), 2.53-2.62 (m, 1H), 2.95 (s, 3H), 3.07-3.17 (m, 1H), 4.19-4.27 (m, 1H), 5.62-5.80 (m, 2H), 6.95-7.01 (m, 1H), 7.30-7.37 (m, 2H), 7.44-7.49 (m, 1H), 8.31 (d, J=7.05 Hz, 1H). LCMS (ESI): m/z calculated for [C$_{23}$H$_{31}$ClN$_2$O$_6$+H]$^+$ 467.19, found 467.18 [M+H]$^+$.

Example 59

Synthesis of 1-((((S)-1-(2-chlorophenyl)-2-oxocyclohexyl)(methyl)carbamoyl)oxy)ethyl acetyl-L-alloisoleucinate (59)

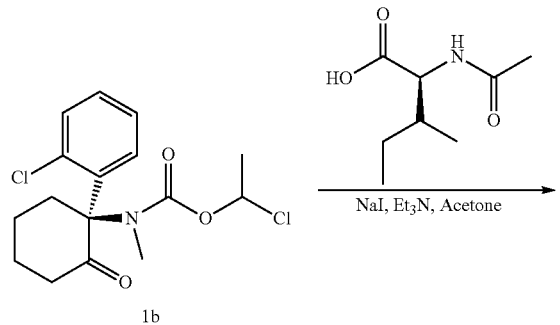

Example 60

Synthesis of ((((S)-1-(2-chlorophenyl)-2-oxocyclohexyl)(methyl)carbamoyl)oxy)methyl acetyl-L-alloisoleucinate (60)

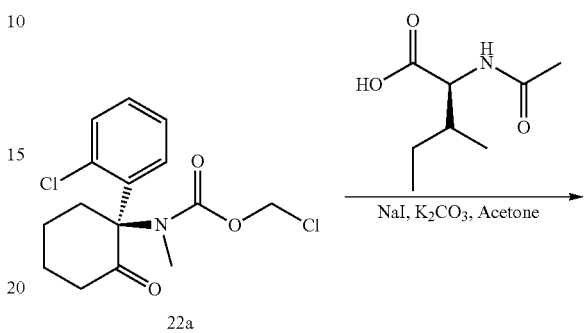

To a solution of 1b (100 mg, 0.29 mmol), NaI (87 mg, 0.58 mmol) and (2S,3R)-2-acetamido-3-methylpentanoic acid (151 mg, 0.87 mmol) in acetone (4 mL) was added triethylamine (0.163 mL, 1.17 mmol). The reaction was heated to 70° C. for 1 h. The reaction was concentrated and redissolved in DCM (5 mL), washed with $H_2O$ (5 mL) and brine (5 mL). The organic layer was dried over $MgSO_4$, filtered and concentrated to provide an oil, which was purified on silica gel column eluting with Hexane/EA (1/0 to 2/3) to afford 88 mg (63% yield) of the title compound 59 as a white solid. $^1$H NMR (500 MHz, DMSO-$d_6$): 0.65-0.78 (m, 2H), 0.78-0.89 (m, 4H), 1.12-1.21 (m, 1H), 1.28-1.59 (m, 4H), 1.62-1.78 (m, 4H), 1.87 (s, 3H), 1.92-2.03 (m, 1H), 2.28-2.39 (m, 2H), 2.55-2.65 (m, 1H), 2.91-2.99 (m, 3H), 3.04-3.20 (m, 1H), 4.08-4.25 (m, 1H), 6.62-6.74 (m, 1H), 6.90-7.01 (m, 1H), 7.27-7.38 (m, 2H), 7.42-7.51 (m, 1H), 8.09-8.22 (m, 1H). LCMS (ESI): m/z calculated for $[C_{24}H_{33}ClN_2O_6+H]^+$ 481.20, found 481.16 $[M+H]^+$.

To a solution of 22a (100 mg, 0.30 mmol), NaI (91 mg, 0.60 mmol) and (2S,3R)-2-acetamido-3-methylpentanoic acid (157 mg, 0.91 mmol) in acetone (4 mL) was added $K_2CO_3$ (209 mg, 1.51 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 3/2) to afford 130 mg (92% yield) of the title compound 60 as a white solid. $^1$H NMR (500 MHz, DMSO-$d_6$): 0.79-0.92 (m, 6H), 1.17-1.28 (m, 1H), 1.37-1.49 (m, 1H), 1.56-1.81 (m, 4H), 1.88 (s, 3H), 1.92-2.02 (m, 1H), 2.30-2.41 (m, 2H), 2.53-2.62 (m, 1H), 2.95 (s, 3H), 3.07-3.19 (m, 1H), 4.14-4.24 (m, 1H), 5.64-5.83 (m, 2H), 6.92-7.00 (m, 1H), 7.28-7.38 (m, 2H), 7.43-7.51 (m, 1H), 8.19-8.29 (m, 1H). LCMS (ESI): m/z calculated for $[C_{23}H_{31}ClN_2O_6+H]^+$ 467.19, found 467.20 $[M+H]^+$.

Example 61

Synthesis of (S)-(((1-(2-chlorophenyl)-2-oxocyclohexyl)(methyl)carbamoyl)oxy)methyl 2-aminonicotinate (61)

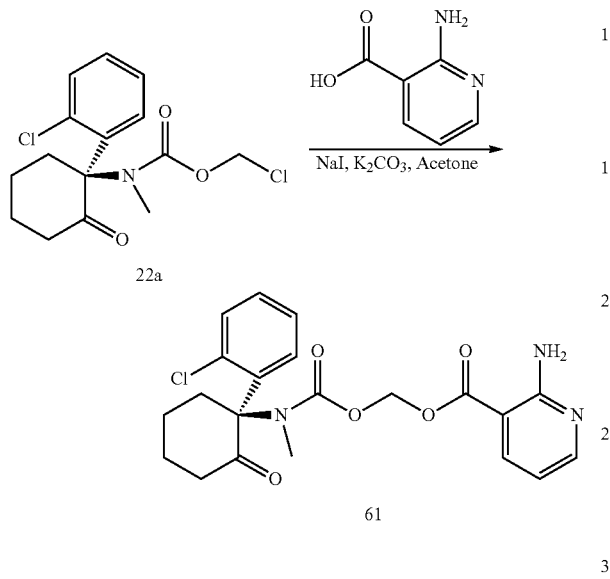

To a solution of 22a (100 mg, 0.15 mmol), NaI (45 mg, 0.30 mmol) and 2-aminopyridine-3-carboxylic acid (63 mg, 0.45 mmol) in acetone (2 mL) was added $K_2CO_3$ (105 mg, 0.76 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 2/3) to afford 40 mg (60% yield) of the title compound 61 as a pale-yellow foam. $^1$H NMR (600 MHz, DMSO-$d_6$): 1.59-1.76 (m, 3H), 1.90-2.00 (m, 1H), 2.29-2.40 (m, 2H), 2.55-2.63 (m, 2H), 2.98 (s, 3H), 3.05-3.16 (m, 1H), 5.80-6.04 (m, 2H), 6.63-6.71 (m, 1H), 6.93-6.99 (m, 1H), 7.18-7.27 (m, 3H), 7.28-7.34 (m, 1H), 7.42-7.48 (m, 1H), 7.99-8.07 (m, 1H), 8.26 (dd, J=4.6, 1.9 Hz, 1H). LCMS (ESI): m/z calculated for $[C_{21}H_{22}ClN_3O_5+H]^+$ 432.12, found 432.02 $[M+H]^+$.

Example 62

Synthesis of 1-((((R)-1-(2-chlorophenyl)-2-oxocyclohexyl)(methyl)carbamoyl)oxy)ethyl acetylglycinate (62)

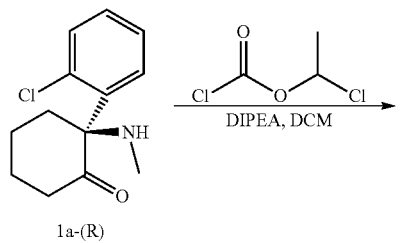

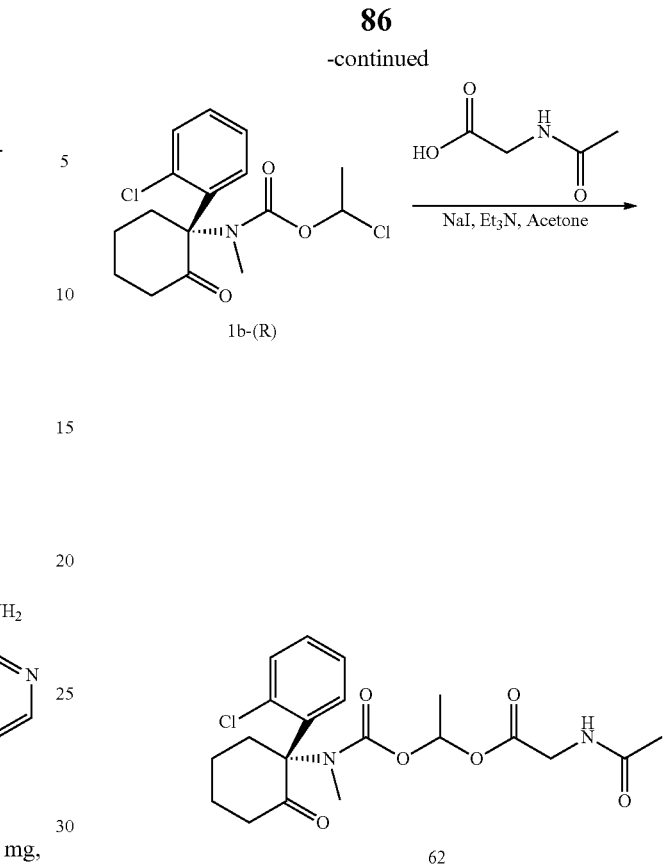

To a solution of R-ketamine (1a-(R)) (1.0 g, 4.2 mmol) and DIPEA (1.36 g, 10.5 mmol) in DCM (42 mL) was added 1-chloroethyl carbonochloridate (1.50 g, 10.5 mmol) slowly at 0° C. The reaction was stirred at 25° C. for 1.5 h. The reaction was diluted with DCM (10 mL) and washed with water (20 mL) and brine (20 mL). The organic layer was dried over $MgSO_4$, filtered and concentrated to provide an oil. The oil was diluted with ice MeOH and filtered to afford 1.14 g (80% yield) of 1b-(R) as a white solid. $^1$H NMR (600 MHz, $CDCl_3$): δ 1.60-1.96 (m, 6H), 2.00-2.09 (m, 1H), 2.30-2.56 (m, 1H), 2.57-2.63 (m, 1H), 2.67-2.86 (m, 1H), 3.02 and 3.07 (two s, total 3H), 3.24-3.39 (m, 1H), 6.48-6.60 (m, 1H), 6.90-7.03 (m, 1H), 7.22-7.28 (m, 2H), 7.42-7.48 (m, 1H).

To a solution of 1b-(R) (52 mg, 0.15 mmol), NaI (24 mg, 0.16 mmol) and acetylglycine (53 mg, 0.45 mmol) in acetone (1 mL) was added triethylamine (0.1 mL, 0.75 mmol). The reaction was heated to 70° C. for 16 h. The reaction was concentrated and redissolved in DCM (10 mL), washed with $NaHCO_{3(sat)}$ (10 mL) and brine (10 mL). The organic layer was dried over $MgSO_4$, filtered and concentrated to provide an oil, which was purified on silica gel column eluting with Hexane/EA (1/0 to 1/2) to afford 39 mg (61% yield) of the title compound 62 as a white foam. $^1$H NMR (500 MHz, DMSO-$d_6$): 1.36-1.56 (m, 3H), 1.60-1.78 (m, 3H), 1.86 (d, J=3.05 Hz, 3H), 1.95-2.03 (m, 1H), 2.28-2.36 (m, 2H), 2.55-2.62 (m, 1H), 2.95 and 2.97 (two s, total 3H), 3.06-3.20 (m, 1H), 3.70-3.79 (m, 1H), 3.81-3.94 (m, 1H), 6.61-6.69 (m, 1H), 6.92-7.00 (m, 1H), 7.29-7.37 (m, 2H), 7.43-7.49 (m, 1H), 8.28-8.37 (m, 1H). LCMS (ESI): m/z calculated for $[C_{20}H_{25}ClN_2O_6+H]^+$ 425.14, found 425.23 $[M+H]^+$.

Example 63

Synthesis of 1-((((R)-1-(2-chlorophenyl)-2-oxocyclohexyl)(methyl)carbamoyl)oxy)ethyl 2-(3-methyloxetan-3-yl)acetate (63)

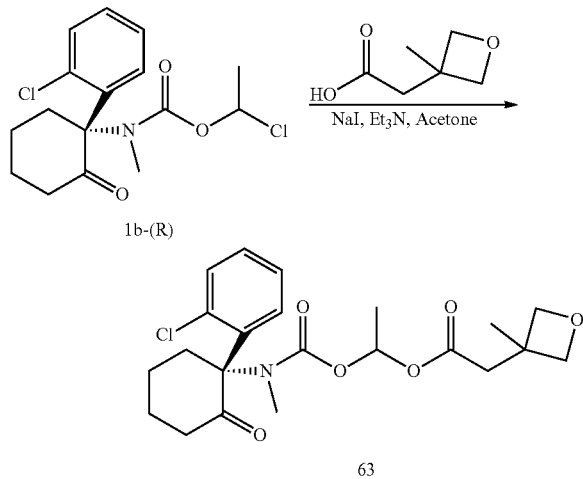

To a solution of 1b-(R) (121 mg, 0.35 mmol), NaI (105 mg, 0.7 mmol) and 2-(3-methyloxetan-3-yl)acetic acid (137 mg, 1.05 mmol) in acetone (5 mL) was added K$_2$CO$_3$ (242 mg, 1.75 mmol). The reaction was heated to 70° C. for 4 h. The reaction was concentrated and redissolved in DCM (5 mL), washed with H$_2$O (5 mL) and brine (5 mL). The organic layer was dried over MgSO$_4$, filtered and concentrated to provide an oil, which was purified on silica gel column eluting with Hexane/EA (1/0 to 3/1) to afford a yellow oil. Ether (3 mL) was added, filtered and the solid was washed with cold ether to afford 15 mg (10% yield) of the title compound 63 as a white solid. $^1$H NMR (600 MHz, methanol-d$_4$): 1.38 (s, 3H), 1.41-1.64 (m, 3H), 1.72-1.88 (m, 3H), 2.04-2.10 (m, 1H), 2.32-2.39 (m, 1H), 2.43-2.51 (m, 1H), 2.66-2.72 (m, 1H), 2.73 (s, 2H), 3.05 (s, 3H), 3.32-3.34 (m, 1H), 4.34-4.39 (m, 2H), 4.57-4.64 (m, 2H), 6.68-6.75 (m, 1H), 7.01-7.15 (m, 1H), 7.27-7.34 (m, 2H), 7.44-7.48 (m, 1H). LCMS (ESI): m/z calculated for [C$_{22}$H$_{25}$ClNO$_6$+H]$^+$ 438.16, found 438.25 [M+H]$^+$.

Example 64

Synthesis of 1-((((R)-1-(2-chlorophenyl)-2-oxocyclohexyl)(methyl)carbamoyl)oxy)ethyl acetyl-L-alaninate (64)

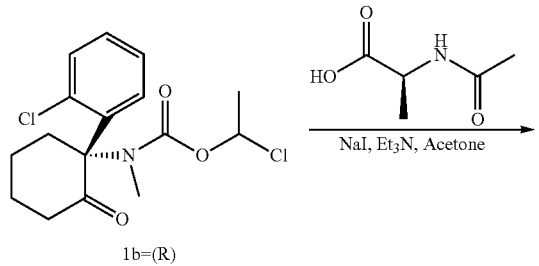

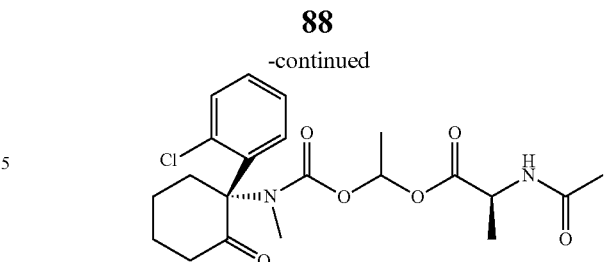

To a solution of 1b-(R) (52 mg, 0.15 mmol), NaI (24 mg, 0.16 mmol) and (S)-2-acetamidopropanoic acid (59 mg, 0.45 mmol) in acetone (1 mL) was added triethylamine (0.1 mL, 0.75 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/1) to afford 47 mg (72% yield) of the title compound 64 as a white foam. $^1$H NMR (600 MHz, DMSO-d$_6$): δ 1.15-1.30 (m, 3H), 1.34-1.58 (m, 3H), 1.60-1.77 (m, 3H), 1.84 (d, J=14.16 Hz, 3H), 1.96-2.03 (m, 1H), 2.26-2.38 (m, 2H), 2.51-2.64 (m, 1H), 2.96 and 2.97 (two s, total 3H), 3.06-3.20 (m, 1H), 4.10-4.26 (m, 1H), 6.60-6.65 (m, 1H), 6.92-7.02 (m, 1H), 7.25-7.36 (m, 2H), 7.44-7.49 (m, 1H), 8.25-8.37 (m, 1H). LCMS (ESI): m/z calculated for [C$_{21}$H$_{27}$ClN$_2$O$_6$+H]$^+$ 439.16, found 439.30 [M+H]$^+$.

Example 65

Synthesis of 1-((((R)-1-(2-chlorophenyl)-2-oxocyclohexyl)(methyl)carbamoyl)oxy)ethylacetyl-L-valinate (65)

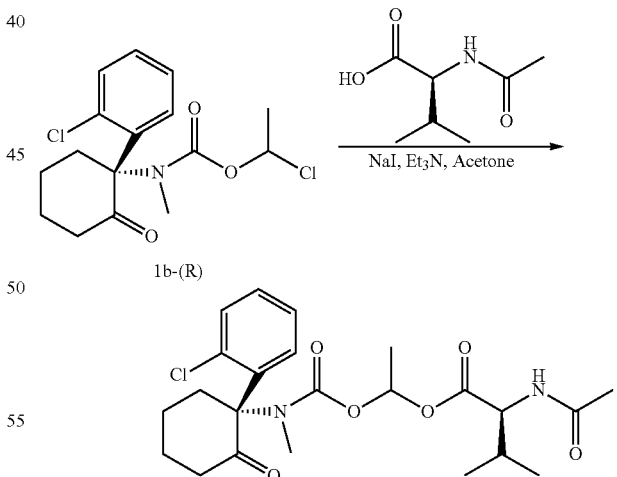

To a solution of 1b-(R) (52 mg, 0.15 mmol), NaI (24 mg, 0.16 mmol) and (S)-2-acetamido-3-methylbutanoic acid (72 mg, 0.45 mmol) in acetone (1 mL) was added triethylamine (0.1 mL, 0.75 mmol). The reaction was heated to 70° C. for 16 h. The reaction was concentrated and redissolved in DCM (5 mL), washed with NaHCO$_{3(sat)}$ (5 mL) and brine (5 mL). The organic layer was dried over MgSO$_4$, filtered concentrated to provide an oil, which was purified on silica gel column eluting with Hexane/EA (1/0 to 1/1) to afford 49 mg (70% yield) of the title compound 65 as a white foam. $^1$H NMR (500 MHz, DMSO-d$_6$): δ 0.82-0.93 (m, 6H), 1.36-1.56 (m, 3H), 1.60-1.77 (m, 3H), 1.88 (d, J=21.3 Hz, 3H), 1.94-2.06 (m, 1H), 2.27-2.35 (m, 2H), 2.54-2.62 (m, 1H), 2.95 and 2.97 (two s, total 3H), 3.06-3.20 (m, 2H), 4.09-4.20 (m, 1H), 6.55-6.70 (m, 1H), 6.92-7.01 (m, 1H), 7.25-7.36 (m, 2H), 7.44-7.49 (m, 1H), 8.10-8.20 (m, 1H). LCMS (ESI): m/z calculated for [C$_{23}$H$_{31}$ClN$_2$O$_6$+H]$^+$ 467.19, found 467.20 [M+H]$^+$.

Example 66

Synthesis of (R)-(((1-(2-chlorophenyl)-2-oxocyclohexyl)(methyl)carbamoyl)oxy)methyl 2-(3-methyloxetan-3-yl)acetate (66)

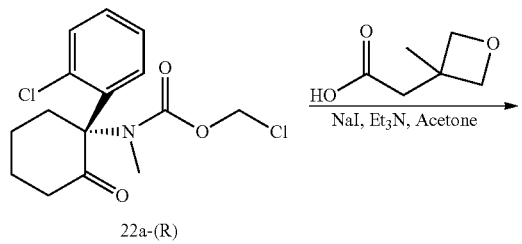

22a-(R)

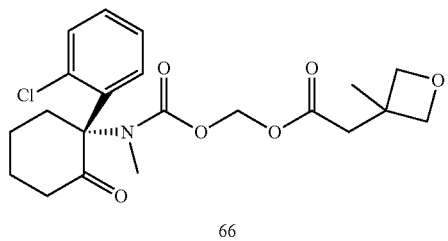

66

To a solution of 22a-(R) (152 mg, 0.46 mmol), NaI (138 mg, 0.92 mmol) and 2-(3-methyloxetan-3-yl)acetic acid (120 mg, 0.92 mmol) in acetone (3 mL) was added K$_2$CO$_3$ (254 mg, 1.84 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 1/2) to afford 74 mg (38% yield) of the title compound 66 as a colorless oil. $^1$H NMR (500 MHz, DMSO-d$_6$): δ 1.32 (s, 3H), 1.60-1.79 (m, 3H), 1.92-2.02 (m, 1H), 2.30-2.41 (m, 2H), 2.53-2.62 (m, 1H), 2.76 (s, 2H), 2.95 (s, 3H), 3.07-3.15 (m, 1H), 4.23 (d, J=5.8 Hz, 2H), 4.45 (d, J=5.7 Hz, 2H), 5.62-5.74 (m, 2H), 6.94-6.99 (m, 1H), 7.29-7.36 (m, 2H), 7.45-7.50 (m, 1H). LCMS (ESI): m/z calculated for [C$_{21}$H$_{26}$ClNO$_6$+H]$^+$ 424.14, found 424.26 [M+H]$^+$.

Example 67

Synthesis of (R)-(((1-(2-chlorophenyl)-2-oxocyclohexyl)(methyl)carbamoyl)oxy)methyl nicotinate (67)

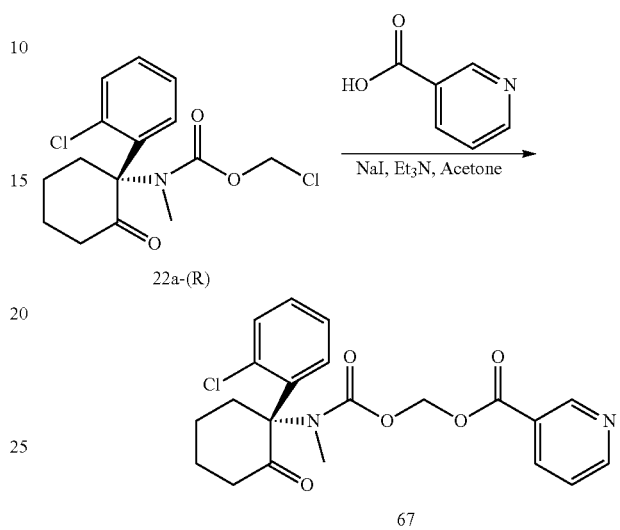

67

To a solution of 22a-(R) (495 mg, 1.5 mmol), NaI (450 mg, 3.0 mmol) and nicotinic acid (554 mg, 4.5 mmol) in acetone (18 mL) was added triethylamine (1.05 mL, 7.5 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (3/2) to afford 188 mg (30% yield) of the title compound 67 as a white solid. $^1$H NMR (500 MHz, DMSO-d$_6$): δ 1.60-1.77 (m, 3H), 1.90-2.00 (m, 1H), 2.30-2.40 (m, 2H), 2.56-2.65 (m, 1H), 2.99 (s, 3H), 3.06-3.15 (m, 1H), 5.88-6.08 (m, 2H), 6.97-7.02 (m, 1H), 7.21-7.26 (m, 1H), 7.27-7.33 (m, 1H), 7.42-7.47 (m, 1H), 7.60-7.65 (m, 1H), 8.28-8.35 (m, 1H), 8.86-8.90 (m, 1H), 9.07-9.13 (m, 1H). LCMS (ESI): m/z calculated for [C$_{21}$H$_{21}$ClN$_2$O$_5$+H]$^+$ 417.11, found 417.2 [M+H]$^+$.

Example 68

Synthesis of (R)-(((1-(2-chlorophenyl)-2-oxocyclohexyl)(methyl)carbamoyl)oxy)methyl acetylglycinate

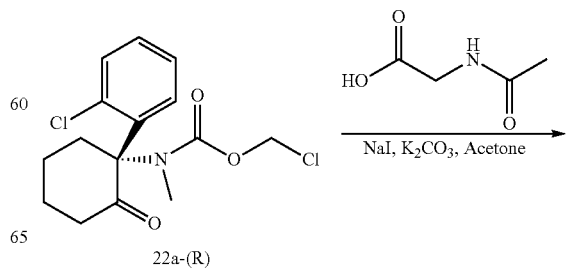

22a-(R)

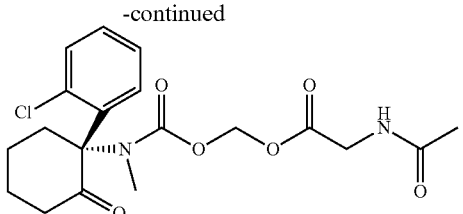

68

To a solution of 22a-(R) (50 mg, 0.15 mmol), NaI (45 mg, 0.30 mmol) and 2-acetamidoacetic acid (53.2 mg, 0.45 mmol) in acetone (2 mL) was added $K_2CO_3$ (105 mg, 0.76 mmol). The reaction was heated to 70° C. for 3 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 1/4) to afford 17 mg (27% yield) of the title compound 68 as a white foam. $^1$H NMR (500 MHz, DMSO-$d_6$): 1.62-1.77 (m, 3H), 1.87 (s, 3H), 1.94-2.04 (br, 1H), 2.29-2.41 (m, 2H), 2.55-2.65 (m, 1H), 2.96 (s, 3H), 3.06-3.18 (m, 1H), 3.79-3.93 (m, 2H), 5.62-5.79 (m, 2H), 6.93-7.01 (m, 1H), 7.29-7.39 (m, 2H), 7.43-7.50 (m, 1H), 8.38 (t, J=5.8 Hz, 1H). LCMS (ESI): m/z calculated for $[C_{19}H_{23}ClN_2O_6+H]^+$ 411.12, found 411.29 $[M+H]^+$.

Example 69

Synthesis of ((((R)-1-(2-chlorophenyl)-2-oxocyclohexyl)(methyl)carbamoyl)oxy)methyl acetyl-L-valinate (69)

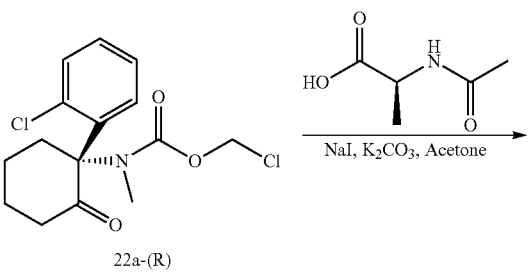

22a-(R)

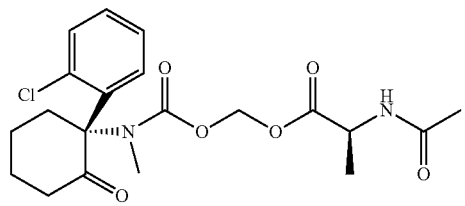

69

To a solution of 22a-(R) (50 mg, 0.15 mmol), NaI (45 mg, 0.30 mmol) and (S)-2-acetamido-3-methylbutanoic acid (72 mg, 0.45 mmol) in acetone (2 mL) was added $K_2CO_3$ (105 mg, 0.76 mmol). The reaction was heated to 70° C. for 3 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 1/4) to afford 56 mg (82% yield) of the title compound 69 as a white foam. $^1$H NMR (600 MHz, DMSO-$d_6$): 0.89-0.96 (m, 6H) 1.59-1.78 (br, 3H), 1.88 (s, 3H), 1.92-2.08 (br, 2H), 2.30-2.39 (m, 2H), 2.54-2.62 (m, 1H), 2.95 (s, 3H), 3.08-3.16 (m, 1H), 4.09-4.17 (m, 1H), 5.66-5.83 (m, 2H), 6.91-6.98 (m, 1H), 7.26-7.38 (m, 2H), 7.44-7.51 (m, 1H), 8.23 (d, J=7.3 Hz, 1H). LCMS (ESI): m/z calculated for $[C_{22}H_{29}ClN_2O_6+H]^+$ 453.17, found 453.21 $[M+H]^+$.

Example 70

Synthesis of ((((R)-1-(2-chlorophenyl)-2-oxocyclohexyl)(methyl)carbamoyl)oxy)methyl acetyl-L-alaninate (70)

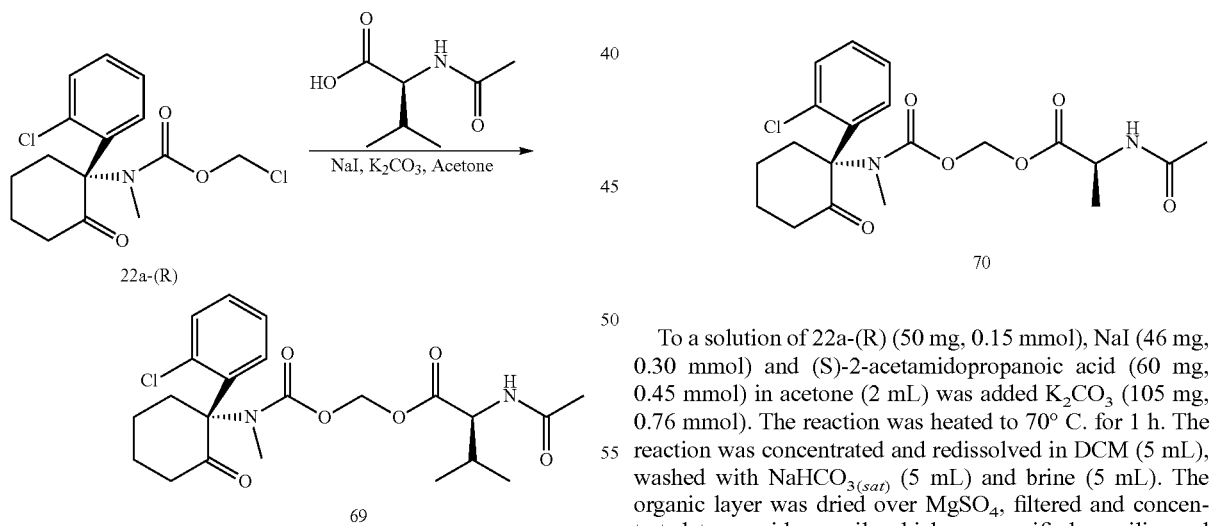

To a solution of 22a-(R) (50 mg, 0.15 mmol), NaI (46 mg, 0.30 mmol) and (S)-2-acetamidopropanoic acid (60 mg, 0.45 mmol) in acetone (2 mL) was added $K_2CO_3$ (105 mg, 0.76 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 13/7) to afford 54 mg (84% yield) of the title compound 70 as a white foam. $^1$H NMR (600 MHz, DMSO-$d_6$): δ 1.22-1.33 (m, 3H), 1.63-1.76 (m, 3H), 1.84 (s, 3H), 1.95-2.01 (m, 1H), 2.30-2.41 (m, 2H), 2.55-2.63 (m, 1H), 2.95 (s, 3H), 3.07-3.16 (m, 1H), 4.18-4.26 (m, 1H), 5.65-5.78 (m, 2H), 6.90-7.00 (m, 1H), 7.26-7.38 (m, 2H), 7.43-7.50 (m, 1H), 8.38 (d, J=6.1 Hz, 1H). LCMS (ESI): m/z calculated for $[C_{20}H_{25}ClN_2O_6+H]^+$ 425.14, found 425.21 $[M+H]^+$.

Example 71

Synthesis of ((((R)-1-(2-chlorophenyl)-2-oxocyclohexyl)(methyl)carbamoyl)oxy)methyl acetyl-L-leucinate (71)

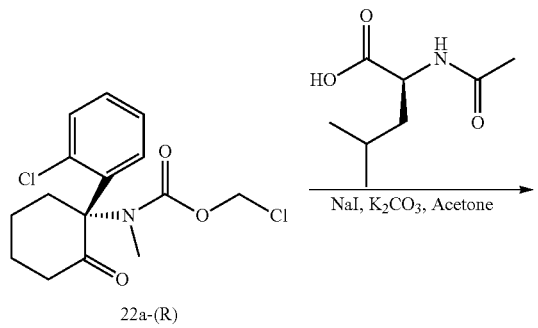

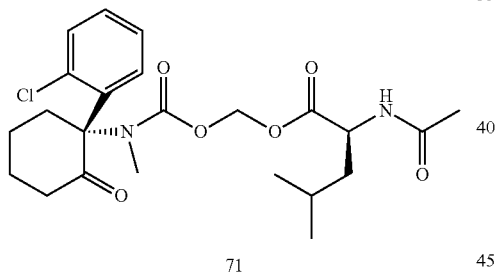

To a solution of 22a-(R) (50 mg, 0.15 mmol), NaI (45 mg, 0.3 mmol) and (S)-2-acetamido-4-methylpentanoic acid (78 mg, 0.45 mmol) in acetone (2 mL) was added $K_2CO_3$ (104 mg, 0.75 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 3/2) to afford 55 mg (79% yield) of the title compound 71 as a white foam. $^1$H NMR (500 MHz, DMSO-$d_6$): δ 0.85 (d, J=6.50 Hz, 3H), 0.90 (d, J=6.55 Hz, 3H), 1.42-1.60 (m, 2H), 1.60-1.78 (m, 4H), 1.85 (s, 3H), 1.92-2.00 (m, 1H), 2.31-2.41 (m, 2H), 2.54-2.63 (m, 1H), 2.94 (s, 3H), 3.06-3.15 (m, 1H), 4.20-4.27 (m, 1H), 5.65-5.80 (m, 2H), 6.94-7.00 (m, 1H), 7.28-7.37 (m, 2H), 7.45-7.49 (m, 1H), 8.31 (d, J=7.10 Hz, 1H). LCMS (ESI): m/z calculated for $[C_{23}H_{31}ClN_2O_6+H]^+$ 467.19, found 467.22 $[M+H]^+$.

Example 72

Synthesis of ((((R)-1-(2-chlorophenyl)-2-oxocyclohexyl)(methyl)carbamoyl)oxy)methyl acetyl-L-alloisoleucinate (72)

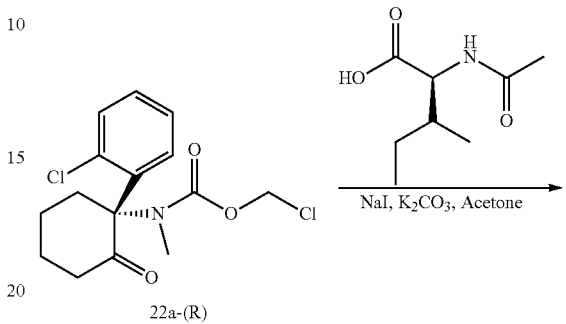

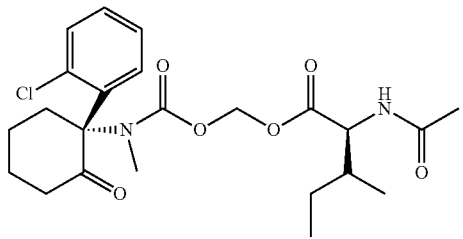

To a solution of 22a-(R) (50 mg, 0.15 mmol), NaI (45 mg, 0.30 mmol) and (2S,3R)-2-acetamido-3-methylpentanoic acid (79 mg, 0.45 mmol) in acetone (2 mL) was added $K_2CO_3$ (105 mg, 0.76 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 3/2) to afford 60 mg (85% yield) of the title compound 72 as a white foam. $^1$H NMR (600 MHz, DMSO-$d_6$): 0.81-0.92 (m, 6H), 1.18-1.26 (m, 1H), 1.38-1.49 (m, 1H), 1.59-1.81 (m, 4H), 1.87 (s, 3H), 1.93-2.01 (m, 1H), 2.30-2.40 (m, 2H), 2.54-2.62 (m, 1H), 2.95 (s, 3H), 3.08-3.16 (m, 1H), 4.14-4.20 (m, 1H), 5.66-5.82 (m, 2H), 6.93-6.98 (m, 1H), 7.29-7.37 (m, 2H), 7.45-7.50 (m, 1H), 8.26 (d, J=7.2 Hz, 1H). LCMS (ESI): m/z calculated for $[C_{23}H_{31}ClN_2O_6+H]^+$ 467.19, found 467.170 $[M+H]^+$.

Example 73

Synthesis of (R)-(((1-(2-chlorophenyl)-2-oxocyclohexyl)(methyl)carbamoyl)oxy)methyl 2-aminonicotinate (73)

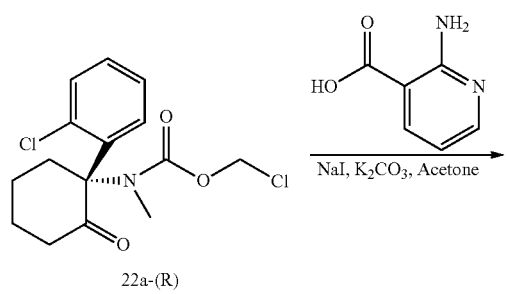

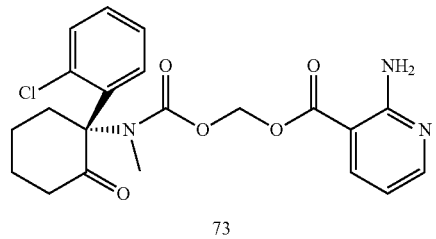

To a solution of 22a-(R) (50 mg, 0.15 mmol), NaI (45 mg, 0.30 mmol) and 2-aminopyridine-3-carboxylic acid (63 mg, 0.45 mmol) in acetone (2 mL) was added $K_2CO_3$ (105 mg, 0.76 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 2/3) to afford 42 mg (64% yield) of the title compound 73 as a pale-yellow foam. $^1$H NMR (600 MHz, DMSO-$d_6$): 1.59-1.76 (m, 3H), 1.90-1.99 (m, 1H), 2.28-2.40 (m, 2H), 2.55-2.63 (m, 1H), 2.98 (s, 3H), 3.06-3.15 (m, 1H), 5.81-6.05 (m, 2H), 6.63-6.71 (m, 1H), 6.90-7.00 (m, 1H), 7.18-7.27 (m, 3H), 7.28-7.34 (m, 1H), 7.41-7.49 (m, 1H), 7.99-8.08 (m, 1H), 8.26 (dd, J=4.6, 1.9 Hz, 1H). CMS (ESI): m/z calculated for $[C_{21}H_{22}ClN_3O_5+H]^+$ 432.12, found 432.11 $[M+H]^+$.

Example 74

Synthesis of ((((S)-1-(2-chlorophenyl)-2-oxocyclohexyl)(methyl)carbamoyl)oxy)methyl dimethyl-L-alloisoleucinate hydrogen chloride (74)

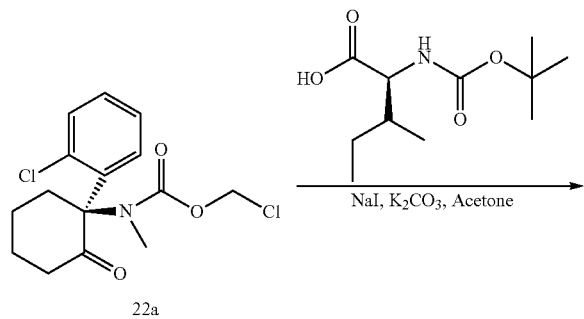

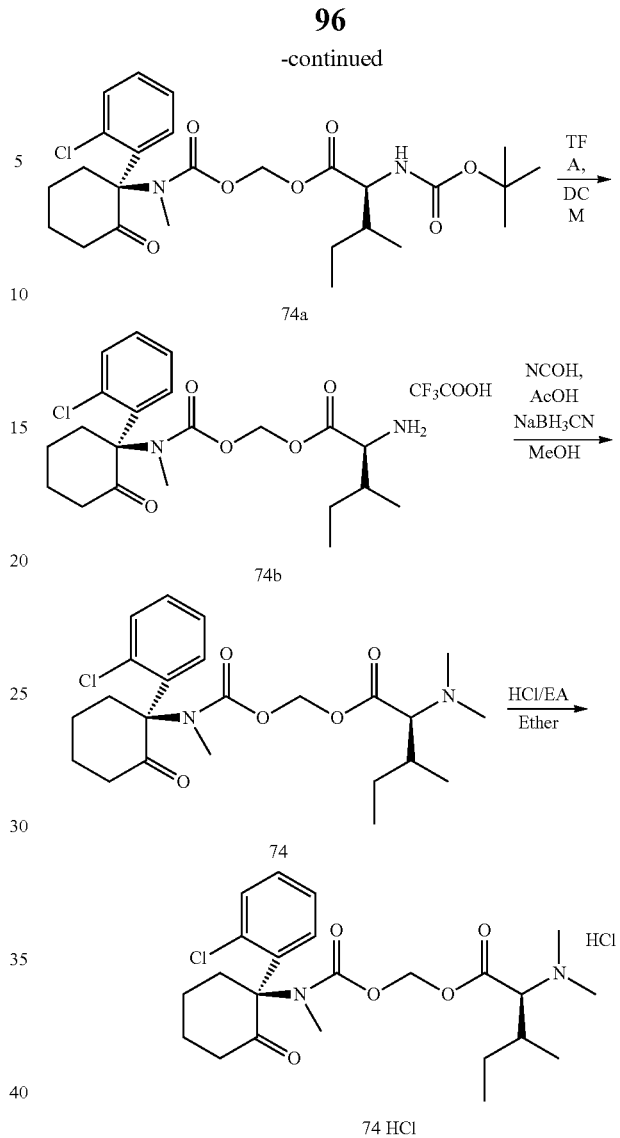

To a solution of 22a (200 mg, 0.6 mmol), NaI (90 mg, 1.2 mmol) and N-(tert-butoxycarbonyl)-L-isoleucine (391 mg, 1.8 mmol) in acetone (7.0 mL) was added $K_2CO_3$ (415 mg, 3.0 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 7/3) to afford 302 mg (96% yield) of 74a as a white foam. $^1$H NMR (600 MHz, DMSO-$d_6$): δ 0.78-0.88 (m, 6H), 1.17-1.28 (m, 1H), 1.32-1.46 (m, 10H), 1.56-1.66 (m, 1H), 1.67-1.80 (m, 3H), 1.93-1.99 (m, 1H), 2.31-2.39 (m, 2H), 2.53-2.59 (m, 1H), 2.95 (s, 3H), 3.09-3.17 (m, 1H), 3.79-3.93 (m, 1H), 5.64-5.84 (m, 2H), 6.92-7.01 (m, 1H), 7.29-7.40 (m, 3H), 7.44-7.50 (m, 1H). LCMS (ESI): m/z calculated for $[C_{26}H_{37}ClN_2O_7+H]^+$ 525.23, found 525.31 $[M+H]^+$.

To a solution of 74a (300 mg, 0.57 mmol) in DCM (20 mL) was added trifluoroacetic acid (0.8 mL, 10.26 mmol). The reaction was stirred at 25° C. for 16 h. The reaction was concentrated to afford 307 mg of 74b as a colorless gum. $^1$H NMR (600 MHz, DMSO-$d_6$): δ 0.84-0.94 (m, 6H), 1.22-1.32 (m, 1H), 1.42-1.51 (m, 1H), 1.56-1.79 (m, 3H), 1.83-1.91 (m, 1H), 1.92-1.99 (m, 1H), 2.35-2.43 (m, 2H), 2.53-

2.60 (m, 1H), 2.96 (s, 3H), 3.08-3.16 (m, 1H), 4.11 (br, 1H), 5.74-6.04 (m, 2H), 6.95-7.01 (m, 1H), 7.30-7.37 (m, 2H), 7.45-7.50 (m, 1H), 8.41 (br, 3H). LCMS (ESI): m/z calculated for $[C_{21}H_{29}ClN_2O_5+H]^+$ 425.18, found 425.22 $[M+H]^+$.

Compound 74b (108 mg, 0.2 mmol) was dissolved in MeOH (5.0 mL) and cooled to 0° C. in an ice bath. Acetic acid (0.046 mL, 0.8 mmol) and NaBH$_3$CN (44 mg, 0.7 mmol) was added to the above solution and stirred at 0° C. for 5 min. Formaldehyde (37% in H$_2$O, 0.045 mL) was added at 0° C. and the reaction mixture was stirred at 30° C. for 2 h. The reaction was quenched with NaHCO$_3$ and diluted with water (5 mL). The aqueous layer was extracted with DCM (5 mL) and the organic layer was washed with brine (5 mL). The organic layer was dried over MgSO$_4$, filtered and concentrated to afford 67 mg of 74 as a colorless gum. $^1$H NMR (600 MHz, DMSO-d$_6$): δ 0.76-0.87 (m, 6H), 1.06-1.15 (m, 1H), 1.56-1.66 (m, 2H), 1.66-1.76 (m, 2H), 1.76-1.83 (m, 1H), 1.92-1.99 (m, 1H), 2.23 (s, 6H), 2.32-2.39 (m, 2H), 2.54-2.63 (m, 1H), 2.83-2.90 (m, 1H), 2.96 (s, 3H), 3.08-3.16 (m, 1H), 5.70-5.83 (m, 2H), 6.92-6.96 (m, 1H), 7.27-7.36 (m, 2H), 7.46-7.49 (m, 1H). LCMS (ESI): m/z calculated for $[C_{23}H_{33}ClN_2O_5+H]^+$ 453.21, found 453.38 $[M+H]^+$.

To a solution of 74 (59 mg, 0.13 mmol) in ether (3.25 mL) was added HCl (0.39 mL, 1N solution in EA). The reaction was stirred at 25° C. for 5 min, filtered and the solid was washed with cold ether to afford 51 mg (81% yield) of the title compound 74 HCl as a white solid. $^1$H NMR (600 MHz, DMSO-d$_6$): δ 0.80-0.97 (m, 6H), 1.19-1.29 (m, 1H), 1.38-1.50 (m, 1H), 1.56-1.80 (m, 3H), 1.92-1.99 (m, 1H), 2.10-2.26 (m, 1H), 2.34-2.44 (m, 2H), 2.51-2.60 (m, 1H), 2.82 (br, 6H), 2.97 (s, 3H), 3.07-3.16 (m, 1H), 4.10-4.26 (m, 1H), 5.70-6.05 (m, 2H), 6.96-7.02 (m, 1H), 7.29-7.37 (m, 2H), 7.46-7.50 (m, 1H), 9.97-10.28 (br, 1H). LCMS (ESI): m/z calculated for $[C_{23}H_{33}ClN_2O_5+H]^+$ 453.21, found 453.30 $[M+H]^+$.

Example 75

Synthesis of (((((S)-1-(2-chlorophenyl)-2-oxocyclohexyl)(methyl)carbamoyl)oxy)methyl methyl-L-valinate hydrogen chloride (75)

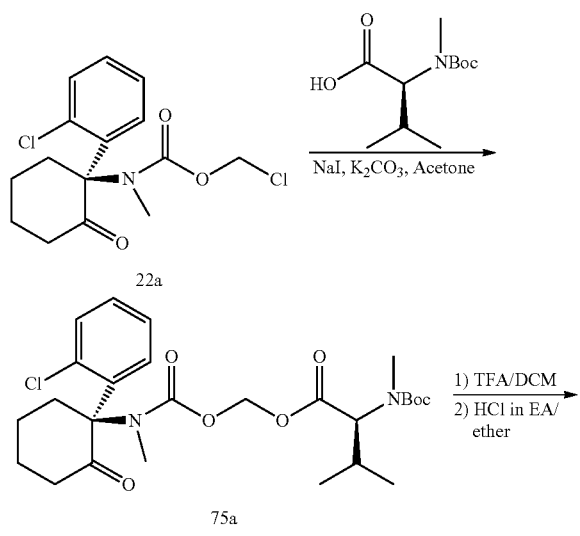

To a solution of 22a (100 mg, 0.3 mmol), NaI (91 mg, 0.6 mmol) and Boc-N-methyl-L-valine (210 mg, 0.91 mmol) in acetone (3 mL) was added K$_2$CO$_3$ (209 mg, 1.5 mmol). The reaction was heated to 70° C. for 1 h. The reaction was concentrated and redissolved in DCM (10 mL), washed with NaHCO$_{3(sat)}$ (10 mL) and brine (10 mL). The organic layer was dried over MgSO$_4$, filtered and concentrated to provide an oil, which was purified on silica gel column eluting with Hexane/EA (1/0 to 4/1) to afford 140 mg (90% yield) of 75a as a sticky solid. $^1$H NMR (600 MHz, acetone-d$_6$): 0.81-1.05 (m, 7H), 1.23-1.34 (m, 1H), 1.45 (s, 9H), 1.71-1.87 (m, 3H), 2.18-2.29 (m, 1H), 2.39-2.53 (m, 2H), 2.63-2.73 (m, 1H), 3.03 (s, 3H), 3.20-3.32 (m, 1H), 4.12-4.51 (m, 1H), 5.74-5.91 (m, 2H), 7.03-7.12 (m, 1H), 7.29-7.37 (m, 2H), 7.43-7.47 (m, 1H). LCMS (ESI): m/z calculated for $[C_{26}H_{37}ClN_2O_7+H]^+$ 525.23, found 525.45 $[M+H]^+$.

To a solution of 75a (80 mg, 0.15 mmol) in DCM (6 mL) was added trifluoroacetic acid (0.21 mL, 2.74 mmol). The reaction was stirred at 25° C. for 16 h. The reaction was concentrated to afford 80 mg of 75 TFA as a colorless gum. $^1$H NMR (600 MHz, DMSO-d$_6$): 0.87-1.07 (m, 6H), 1.55-1.79 (m, 3H), 1.89-2.01 (m, 1H), 2.19-2.30 (m, 1H), 2.32-2.44 (m, 2H), 2.54-2.66 (m, 4H), 2.97 (s, 3H), 3.07-3.18 (m, 1H), 4.10 (s, 1H), 5.70-6.08 (m, 2H), 6.92-7.03 (m, 1H), 7.27-7.40 (m, 2H), 7.43-7.53 (m, 1H), 8.93-9.31 (m, 2H). LCMS (ESI): m/z calculated for $[C_{21}H_{29}ClN_2O_5+H]^+$ 425.18, found 425.36 $[M+H]^+$.

Compound 75 TFA was extracted with DCM (15 mL) and pH=3 HCl$_{(aq)}$ (15 mL). The organic layer was dried over MgSO$_4$, filtered and concentrated to afford a colorless gum. The colorless gum was dissolved in ether (2 mL) and HCl (0.1 mL, 1N solution in EA) was added. The reaction was stirred at 25° C. for 5 min, filtered and the solid was washed with cold ether to afford 26 mg (40% yield) of the title compound 75 HCl as a white solid. $^1$H NMR (500 MHz, methanol-d4): δ 0.97-1.17 (m, 6H), 1.20-1.41 (m, 3H), 1.65-1.82 (m, 2H), 1.82-1.94 (m, 1H), 1.95-2.07 (m, 1H), 2.25-2.38 (m, 1H), 2.40-2.63 (m, 2H), 2.65-2.80 (m, 4H), 2.99-3.09 (m, 3H), 3.93-4.06 (m, 1H), 5.69-6.14 (m, 2H), 7.06-7.17 (m, 1H), 7.26-7.38 (m, 2H), 7.43-7.52 (m, 1H). LCMS (ESI): m/z calculated for $[C_{21}H_{29}ClN_2O_5+H]^+$ 425.18, found 425.36 $[M+H]^+$.

Example 76

Synthesis of (((((S)-1-(2-chlorophenyl)-2-oxocyclohexyl)(methyl)carbamoyl)oxy)methyl dimethyl-L-leucinate hydrogen chloride (76)

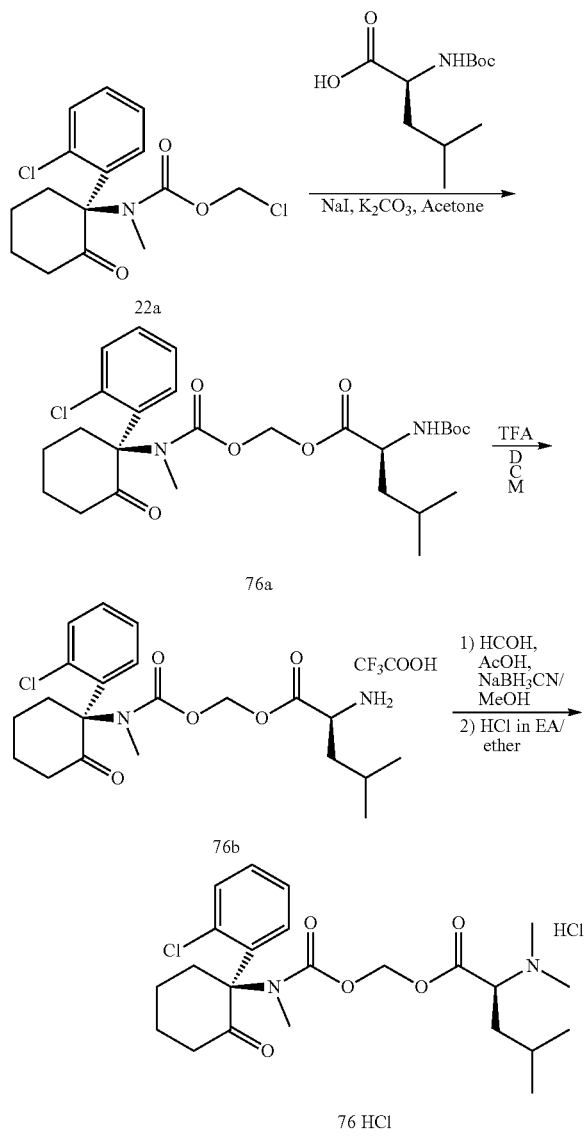

To a solution of 22a (200 mg, 0.6 mmol), NaI (90 mg, 1.2 mmol) and N-(tert-butoxycarbonyl)-L-leucine (391 mg, 1.8 mmol) in acetone (7.0 mL) was added $K_2CO_3$ (415 mg, 3.0 mmol). The reaction was heated to 70° C. for 1 h. The reaction was concentrated and redissolved in DCM (5 mL), washed with $NaHCO_{3(sat)}$ (5 mL) and brine (5 mL). The organic layer was dried over $MgSO_4$, filtered and concentrated to provide an oil, which was purified on silica gel column eluting with Hexane/EA (1/0 to 7/3) to afford 302 mg (96% yield) of 76a as a white foam. $^1$H NMR (500 MHz, DMSO-$d_6$): δ 0.80-0.90 (m, 6H), 1.31-1.44 (m, 10H), 1.49-1.59 (m, 1H), 1.60-1.78 (m, 4H), 1.92-2.00 (m, 1H), 2.30-2.40 (m, 2H), 2.52-2.61 (m, 1H), 2.95 (s, 3H), 3.07-3.17 (m, 1H), 3.88-4.03 (m, 1H), 5.60-5.83 (m, 2H), 6.94-7.02 (m, 1H), 7.29-7.40 (m, 3H), 7.44-7.49 (m, 1H). LCMS (ESI): m/z calculated for $[C_{26}H_{37}ClN_2O_7+H]^+$ 525.23, found 525.16 $[M+H]^+$.

To a solution of 76a (300 mg, 0.57 mmol) in DCM (20 mL) was added trifluoroacetic acid (0.8 mL, 10.26 mmol). The reaction was stirred at 25° C. for 16 h. The reaction was concentrated to afford 307 mg of 76b as a colorless gum. $^1$H NMR (600 MHz, DMSO-$d_6$): δ 0.87-0.92 (m, 6H), 1.55-1.80 (m, 6H), 1.92-1.98 (m, 1H), 2.35-2.42 (m, 2H), 2.53-2.61 (m, 1H), 2.96 (s, 3H), 3.07-3.16 (m, 1H), 4.09 (br, 1H), 5.74-5.97 (m, 2H), 6.97-7.02 (m, 1H), 7.30-7.37 (m, 2H), 7.45-7.50 (m, 1H), 8.45 (br, 3H). LCMS (ESI): m/z calculated for $[C_{21}H_{29}ClN_2O_5+H]^+$ 425.18, found 425.36 $[M+H]^+$.

Compound 76b (245 mg, 0.45 mmol) was dissolved in MeOH (11.25 mL) and cooled to 0° C. in an ice bath. Acetic acid (0.1 mL, 1.8 mmol) and $NaBH_3CN$ (108 mg, 1.575 mmol) was added to the above solution and stirred at 0° C. for 5 min. Formaldehyde (37% in $H_2O$, 0.1 mL) was added at 0° C. and the reaction mixture was stirred at 30° C. for 1 h. The reaction was quenched with $NaHCO_3$ and diluted with water (5 mL). The aqueous layer was extracted with DCM (5 mL) and the organic layer was washed with brine (5 mL) and pH=3 $HCl_{(aq)}$ (25 mL). The organic layer was dried over $MgSO_4$, filtered and concentrated to afford a colorless gum. The colorless gum was dissolved in ether (3.38 mL) and HCl (0.4 mL, 1N solution in EA) was added. The reaction was stirred at 25° C. for 5 min, filtered and the solid was washed with cold ether to afford 28 mg (13% yield) of the title compound 76 HCl as a light yellow solid. $^1$H NMR (500 MHz, DMSO-$d_6$): δ 0.87-0.95 (m, 6H), 1.56-1.85 (m, 6H), 1.91-1.98 (m, 1H), 2.34-2.43 (m, 2H), 2.53-2.62 (m, 1H), 2.80 (s, 6H), 2.97 (s, 3H), 3.07-3.16 (m, 1H), 4.16-4.24 (m, 1H), 5.70-6.00 (m, 2H), 6.96-7.05 (m, 1H), 7.30-7.37 (m, 2H), 7.44-7.50 (m, 1H), 10.90-11.60 (m, 1H). LCMS (ESI): m/z calculated for $[C_{23}H_{33}ClN_2O_5+H]^+$ 453.21, found 453.3 $[M+H]^+$.

Example 77

Synthesis of (((((S)-1-(2-chlorophenyl)-2-oxocyclohexyl)(methyl)carbamoyl)oxy)methyl diethyl-L-valinate hydrogen chloride (77)

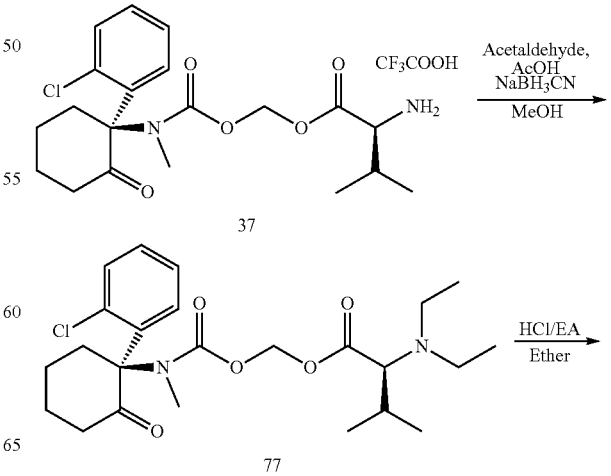

-continued

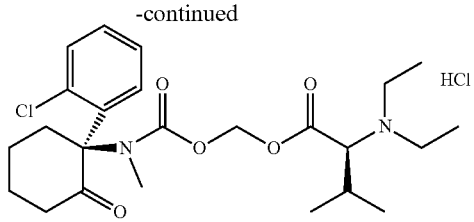

77 HCl

Compound 37 (190 mg, 0.36 mmol) was dissolved in MeOH (18.0 mL) and cooled to 0° C. in an ice bath. Acetic acid (0.082 mL, 1.44 mmol) and NaBH$_3$CN (79 mg, 1.26 mmol) was added to the above solution and stirred at 0° C. for 5 min. Acetaldehyde (0.2 mL, 3.58 mmol) was added at 0° C. and the reaction mixture was stirred at 30° C. for 1.5 h. The reaction was quenched with NaHCO$_3$ and diluted with water (5 mL). The aqueous layer was extracted with DCM (5 mL) and the organic layer was washed with brine (5 mL). The organic layer was dried over MgSO$_4$, filtered and concentrated to afford 148 mg of 77 (88% yield) as a white solid. $^1$H NMR (600 MHz, DMSO-d$_6$): δ 0.84 (d, J=6.4 Hz, 3H), 0.92 (d, J=6.5 Hz, 3H), 0.99 (t, J=7.1 Hz, 6H), 1.56-1.78 (m, 3H), 1.92-2.00 (m, 2H), 2.26-2.41 (m, 4H), 2.54-2.62 (m, 1H), 2.66-2.76 (m, 2H), 2.88-2.93 (m, 1H), 2.95 (s, 3H), 3.08-3.16 (m, 1H), 5.70-5.82 (m, 2H), 6.94-6.97 (m, 1H), 7.27-7.36 (m, 2H), 7.46-7.49 (m, 1H). LCMS (ESI): m/z calculated for [C$_{24}$H$_{35}$ClN$_2$O$_5$+H]$^+$ 467.22, found 467.28 [M+H]$^+$.

To a solution of 77 (100 mg, 0.214 mmol) in ether (5.35 mL) was added HCl (0.64 mL, 1 N solution in EA). The reaction was stirred at 25° C. for 5 min, filtered and the solid was washed with cold ether to afford 88 mg (82% yield) of the title compound 77 HCl as a white solid. $^1$H NMR (600 MHz, DMSO-d$_6$): δ 0.90-1.00 (m, 3H), 1.01-1.09 (m, 3H), 1.14-1.28 (m, 6H), 1.56-1.80 (m, 3H), 1.92-1.98 (m, 1H), 2.32-2.48 (m, 3H), 2.54-2.62 (m, 1H), 2.97 (s, 3H), 3.06-3.28 (m, 5H), 4.14-4.24 (m, 1H), 5.70-6.05 (m, 2H), 6.98-7.04 (m, 1H), 7.28-7.37 (m, 2H), 7.46-7.50 (m, 1H), 9.97-10.10 (br, 1H). LCMS (ESI): m/z calculated for [C$_{24}$H$_{35}$ClN$_2$O$_5$+H]$^+$ 467.22, found 467.39 [M+H]$^+$.

Example 78

Synthesis of ((((S)-1-(2-chlorophenyl)-2-oxocyclo-hexyl)(methyl)carbamoyl)oxy)methyl methyl-L-alaninate 2,2,2-trifluoroacetic acid (78)

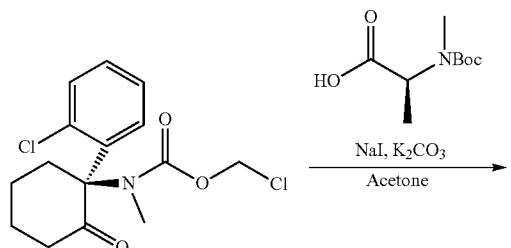

22a

-continued

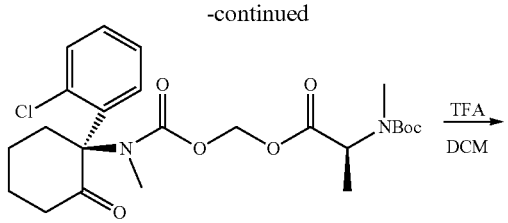

78a

<div style="text-align:center">
[structure of 78 TFA]
</div>

78 TFA

To a solution of 22a (100 mg, 0.3 mmol), NaI (91 mg, 0.6 mmol) and N-(tert-butoxycarbonyl)-N-methyl-L-alanine (185 mg, 0.91 mmol) in acetone (3 mL) was added K$_2$CO$_3$ (209 mg, 1.5 mmol). The reaction was heated to 70° C. for 1 h. The reaction was concentrated and redissolved in DCM (10 mL), washed with NaHCO$_{3(sat)}$ (10 mL) and brine (10 mL). The organic layer was dried over MgSO$_4$, filtered and concentrated to provide an oil, which was purified on silica gel column eluting with Hexane/EA (1/0 to 3/1) to afford 140 mg (94% yield) of 78a as a sticky solid. $^1$H NMR (600 MHz, Acetone-d$_6$): 1.36-1.47 (m, 12H) 1.70-1.87 (m, 3H), 2.39-2.53 (m, 2H), 2.64-2.73 (m, 1H), 2.79-2.86 (m, 4H), 3.04 (s, 3H), 3.21-3.31 (m, 1H), 4.49-4.78 (m, 1H), 5.67-5.90 (m, 2H), 7.06-7.12 (m, 1H), 7.28-7.37 (m, 2H), 7.43-7.48 (m, 1H). LCMS (ESI): m/z calculated for [C$_{24}$H$_{33}$ClN$_2$O$_7$+H]$^+$ 497.2, found 497.21 [M+H]$^+$.

To a solution of 78a (108 mg, 0.217 mmol) in DCM (8 mL) was added trifluoroacetic acid (0.3 mL, 3.91 mmol). The reaction was stirred at 25° C. for 16 h. The reaction was concentrated to afford 100 mg of the title compound 78 TFA as a colorless gum. $^1$H NMR (500 MHz, DMSO-d$_6$): 1.35-1.45 (m, 3H), 1.58-1.82 (m, 3H), 1.91-2.02 (m, 1H), 2.32-2.43 (m, 2H), 2.54-2.65 (m, 3H), 2.98 (s, 3H), 3.06-3.17 (m, 1H), 4.15-4.25 (m, 1H), 5.69-5.98 (m, 2H), 6.96-7.03 (m, 1H), 7.29-7.39 (m, 2H), 7.44-7.53 (m, 1H), 9.03-9.24 (m, 2H). LCMS (ESI): m/z calculated for [C$_{19}$H$_{25}$ClN$_2$O$_5$+H]$^+$ 397.15, found 397.3 [M+H]$^+$.

Example 79

Synthesis of ((((S)-1-(2-chlorophenyl)-2-oxocyclohexyl)(methyl)carbamoyl)oxy)methyl dipropyl-L-valinate (79)

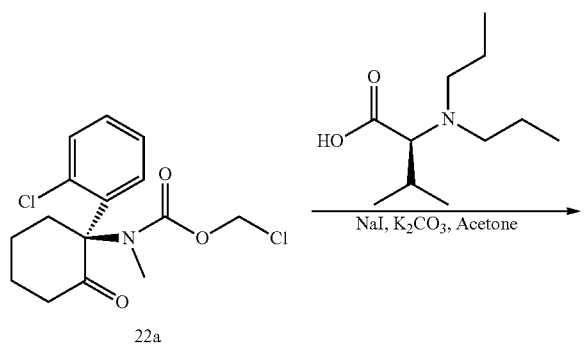

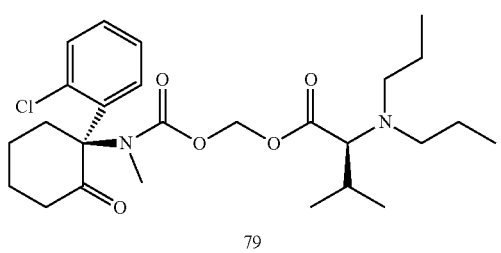

To a solution of 22a (50 mg, 0.15 mmol), NaI (45 mg, 0.30 mmol) and (S)-2-(dipropylamino)-3-methylbutanoic acid (92 mg, 0.45 mmol) in acetone (2 mL) was added K$_2$CO$_3$ (105 mg, 0.76 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 26 mg (35% yield) of the title compound 79 as a white solid. $^1$H NMR (600 MHz, acetone-d$_6$): 0.85-0.92 (m, 9H), 0.98-1.03 (m, 3H), 1.38-1.54 (m, 4H), 1.71-1.87 (m, 3H), 1.98-2.03 (m, 2H), 2.32-2.40 (m, 2H), 2.41-2.48 (m, 1H), 2.49-2.55 (m, 1H), 2.58-2.66 (m, 2H), 2.66-2.74 (m, 1H), 2.87-2.94 (m, 1H), 3.03 (s, 3H), 3.20-3.28 (m, 1H), 5.76-5.89 (m, 2H), 7.06-7.11 (m, 1H), 7.27-7.35 (m, 2H), 7.43-7.49 (m, 1H). LCMS (ESI): m/z calculated for [C$_{26}$H$_{39}$ClN$_2$O$_5$+H]$^+$ 495.25, found 495.16 [M+H]$^+$.

Example 80

Synthesis of ((((S)-1-(2-chlorophenyl)-2-oxocyclohexyl)(methyl)carbamoyl)oxy)methyl L-leucinate hydrogen chloride (80)

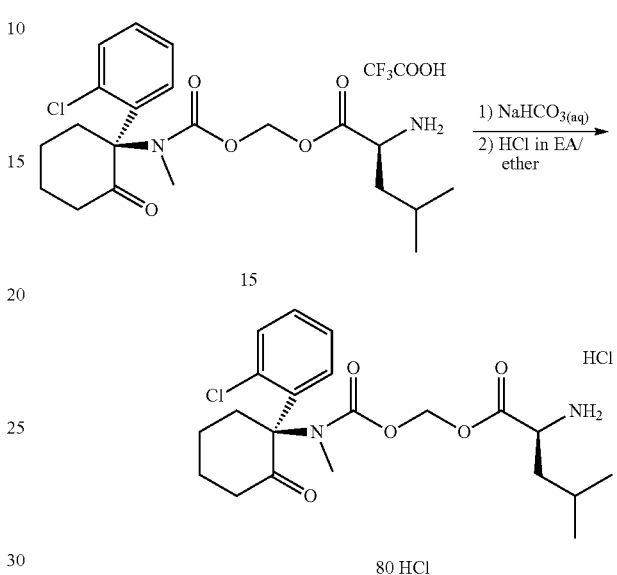

Compound 15 (148 mg, 0.275 mmol) was dissolved in DCM and washed with pH=8 NaHCO$_{3(aq)}$. The organic layer was dried over MgSO$_4$, filtered and concentrated to get a free base compound. The free base compound was dissolved in ether (6.875 mL) and HCl (0.825 mL, 1 N solution in EA) was added. The reaction was stirred at 25° C. for 5 min, filtered and the solid was washed with cold ether to afford 126 mg (99% yield) of the title compound 80 HCl as a white solid. $^1$H NMR (600 MHz, DMSO-d$_6$): δ 0.87-0.92 (m, 6H), 1.57-1.80 (m, 6H), 1.92-1.98 (m, 1H), 2.37-2.43 (m, 2H), 2.54-2.62 (m, 1H), 2.96 (s, 3H), 3.07-3.16 (m, 1H), 4.04-4.10 (m, 1H), 5.70-5.97 (m, 2H), 6.98-7.02 (m, 1H), 7.30-7.38 (m, 2H), 7.46-7.50 (m, 1H), 8.45 (br, 3H). LCMS (ESI): m/z calculated for [C$_{21}$H$_{29}$ClN$_2$O$_5$+H]$^+$ 425.18, found 425.32 [M+H]$^+$.

Example 81

Synthesis of ((((S)-1-(2-chlorophenyl)-2-oxocyclohexyl)(methyl)carbamoyl)oxy)methyl isopropyl-L-valinate hydrogen chloride (81)

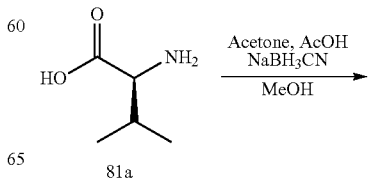

Example 82

Synthesis of ((((S)-1-(2-chlorophenyl)-2-oxocyclohexyl)(methyl)carbamoyl)oxy)methyl propyl-L-valinate hydrochloride (82)

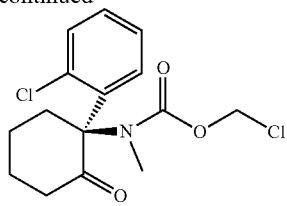

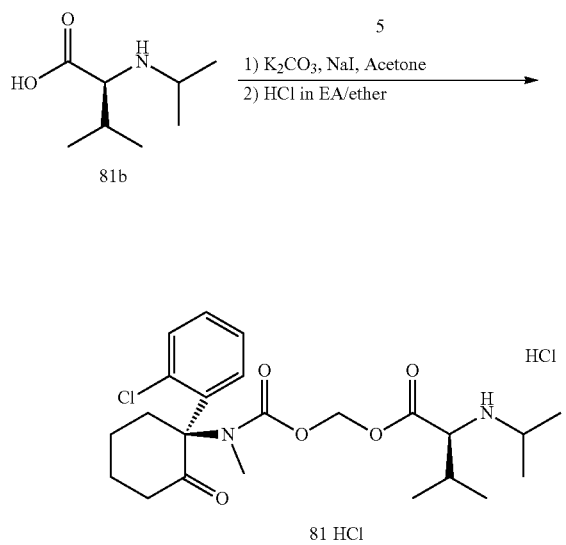

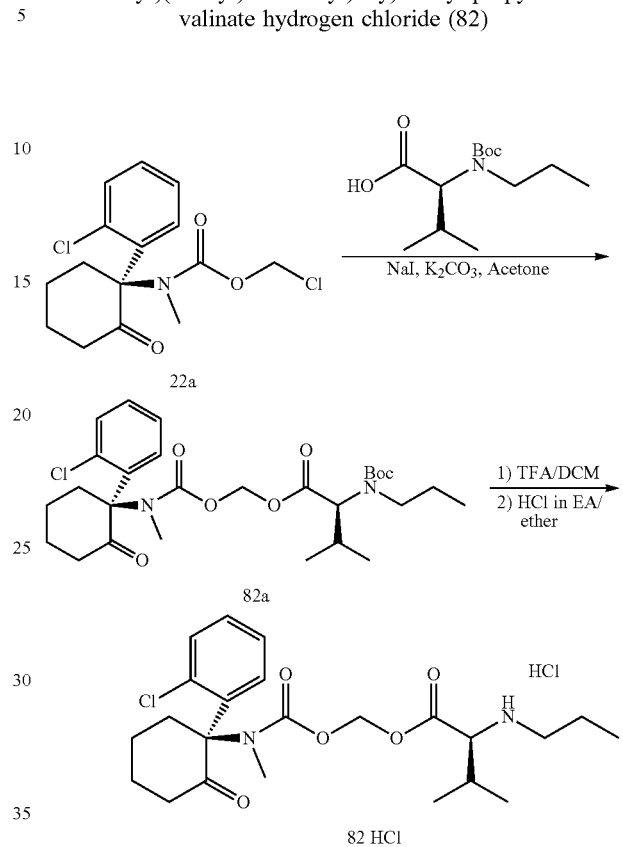

L-valine 81a (234 mg, 2 mmol) was dissolved in MeOH (25.0 mL) and cooled to 0° C. in an ice bath. Acetic acid (0.46 mL, 8 mmol) and NaBH$_3$CN (220 mg, 7 mmol) was added to the above solution and stirred at 0° C. for 5 min. Acetone (1 mL, 18 mmol) was added at 0° C. and the reaction mixture was stirred at 50° C. for 16 h. The reaction was concentrated and washed with acetone, DCM and hexane to afford 315 mg of isopropyl-L-valine 81b (99% yield) as a white solid. $^1$H NMR (600 MHz, methanol-d$_4$): δ 1.06 (d, J=7.0 Hz, 3H), 1.09 (d, J=7.0 Hz, 3H), 1.31 (dd, J=6.6, 0.5 Hz, 3H), 1.36 (d, J=6.6 Hz, 3H), 2.17-2.25 (m, 1H), 3.32-3.38 (m, 1H), 3.40-3.43 (m, 1H). LCMS (ESI): m/z calculated for [C$_8$H$_{17}$NO$_2$+H]$^+$ 160.13, found 159.93 [M+H]$^+$.

To a solution of 22a (50 mg, 0.15 mmol), NaI (45 mg, 0.3 mmol) and 81b (72 mg, 0.45 mmol) in acetone (1.75 mL) was added K$_2$CO$_3$ (103.65 mg, 0.75 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 7/3) to afford a colorless gum. The colorless gum was dissolved in ether (2.25 mL) and HCl (0.27 mL, 1 N solution in EA) was added. The reaction was stirred at 25° C. for 5 min, filtered and the solid was washed with cold ether to afford 20 mg (27% yield) of the title compound 81 HCl as a white solid. $^1$H NMR (600 MHz, DMSO-d$_6$): δ0.96 (d, J=6.6 Hz, 3H), 1.05 (d, J=6.8 Hz, 3H), 1.24-1.29 (m, 6H), 1.56-1.80 (m, 3H), 1.92-1.98 (m, 1H), 2.30-2.44 (m, 4H), 2.54-2.62 (m, 1H), 2.96 (s, 3H), 3.08-3.15 (m, 1H), 4.10-4.16 (m, 1H), 5.74-6.00 (m, 2H), 6.98-7.02 (m, 1H), 7.30-7.37 (m, 2H), 7.46-7.49 (m, 1H), 8.88-9.16 (m, 2H). LCMS (ESI): m/z calculated for [C$_{23}$H$_{33}$ClN$_2$O$_5$+H]$^+$ 453.21, found 453.3 [M+H]$^+$.

To a solution of 22a (100 mg, 0.3 mmol), NaI (91 mg, 0.6 mmol) and N-(tert-butoxycarbonyl)-N-propyl-L-valine (236 mg, 0.91 mmol) in acetone (3 mL) was added K$_2$CO$_3$ (209 mg, 1.5 mmol). The reaction was heated to 70° C. for 1 h. The reaction was concentrated and redissolved in DCM (10 mL), washed with NaHCO$_{3(sat)}$ (10 mL) and brine (10 mL). The organic layer was dried over MgSO$_4$, filtered and concentrated to provide an oil, which was purified on silica gel column eluting with Hexane/EA (1/0 to 9/1) to afford 68 mg (41% yield) of 82a as a sticky solid. $^1$H NMR (500 MHz, acetone-d$_6$): 0.81-1.07 (m, 6H), 1.44 (s, 9H), 1.53-1.67 (m, 2H) 1.71-1.88 (m, 3H), 2.26-2.39 (m, 1H), 2.39-2.46 (m, 1H), 2.47-2.56 (m, 1H), 2.64-2.74 (m, 1H), 2.77-2.79 (m, 4H), 3.03 (s, 3H), 3.07-3.36 (m, 3H), 3.76-4.23 (m, 1H), 5.71-5.91 (m, 2H), 7.05-7.12 (m, 1H), 7.28-7.36 (m, 2H), 7.43-7.48 (m, 1H). LCMS (ESI): m/z calculated for [C$_{28}$H$_{41}$ClN$_2$O$_7$+H]$^+$ 553.26, found 553.20 [M+H]$^+$.

To a solution of 82a (64 mg, 0.116 mmol) in DCM (4 mL) was added trifluoroacetic acid (0.16 mL, 2.08 mmol). The reaction was stirred at 25° C. for 16 h. The reaction was concentrated to afford 60 mg of 82 TFA as a colorless gum. 82 TFA was extracted with DCM (15 mL) and pH=3 HCl$_{(aq)}$ (15 mL). The organic layer was dried over MgSO$_4$, filtered and concentrated to afford a colorless gum. The colorless gum was dissolved in ether (2 mL) and HCl (0.1 mL, 1N solution in EA) was added. The reaction was stirred at 25° C. for 5 min, filtered and the solid was washed with cold ether to afford 40 mg (73% yield) of the title compound 82 HCl as a white solid. $^1$H NMR (600 MHz, methanol-d4): δ

0.97-1.07 (m, 6H), 1.07-1.16 (m, 3H), 1.65-1.82 (m, 4H), 1.83-1.94 (m, 1H), 1.95-2.06 (m, 1H), 2.24-2.37 (m, 1H), 2.40-2.63 (m, 2H), 2.66-2.76 (m, 1H), 2.90-3.01 (m, 2H), 3.04 (s, 3H), 3.97 (s, 1H), 5.70-6.10 (m, 2H), 7.07-7.16 (m, 1H), 7.27-7.36 (m, 2H), 7.43-7.52 (m, 1H). LCMS (ESI): m/z calculated for $[C_{23}H_{33}ClN_2O_5+H]^+$ 453.21, found 453.3 $[M+H]^+$.

Example 83

Synthesis of (((((S)-1-(2-chlorophenyl)-2-oxocyclohexyl)(methyl)carbamoyl)oxy)methyl ethyl-L-valinate (83)

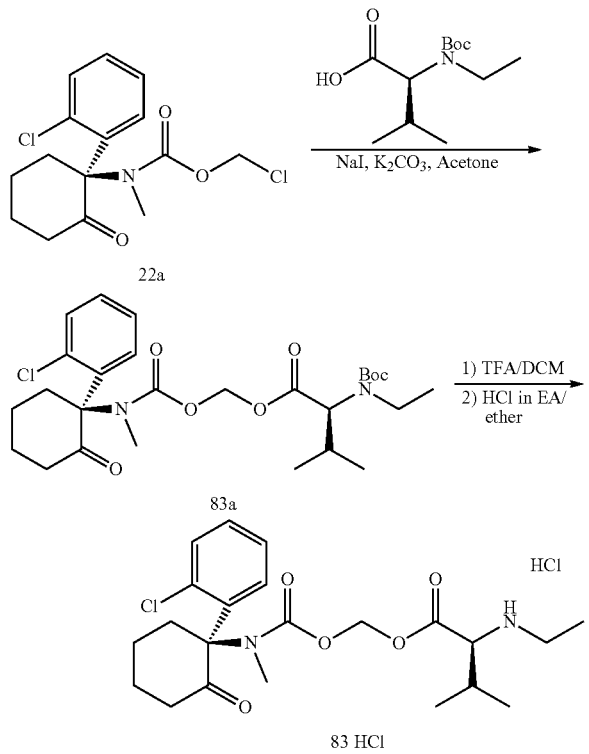

To a solution of 22a (100 mg, 0.3 mmol), NaI (91 mg, 0.6 mmol) and N-(tert-butoxycarbonyl)-N-ethyl-L-valine (223 mg, 0.91 mmol) in acetone (3 mL) was added $K_2CO_3$ (209 mg, 1.5 mmol). The reaction was heated to 70° C. for 1 h. The reaction was concentrated and redissolved in DCM (10 mL), washed with $NaHCO_{3(sat)}$ (10 mL) and brine (10 mL). The organic layer was dried over $MgSO_4$, filtered and concentrated to provide an oil, which was purified on silica gel column eluting with Hexane/EA (1/0 to 9/1) to afford 40 mg (25% yield) of 83a as a sticky solid. $^1$H NMR (500 MHz, acetone-$d_6$): 0.83-1.06 (m, 7H), 1.09-1.19 (m, 3H), 1.45 (s, 9H), 1.71-1.87 (m, 4H), 2.37-2.57 (m, 2H), 2.62-2.75 (m, 1H), 3.03 (s, 3H), 3.17-3.50 (m, 3H), 3.79-4.30 (m, 1H), 5.71-5.94 (m, 2H), 7.03-7.12 (m, 1H), 7.29-7.37 (m, 2H), 7.42-7.49 (m, 1H). LCMS (ESI): m/z calculated for $[C_{27}H_{39}ClN_2O_7+H]^+$ 539.24, found 539.25 $[M+H]^+$.

To a solution of 83a (40 mg, 0.074 mmol) in DCM (3 mL) was added trifluoroacetic acid (0.1 mL, 1.34 mmol). The reaction was stirred at 25° C. for 16 h. The reaction was concentrated to afford 50 mg of 83 TFA as a colorless gum. 83 TFA was extracted with DCM (15 mL) and pH=3 $HCl_{(aq)}$ (15 mL). The organic layer was dried over $MgSO_4$, filtered and concentrated to afford a colorless gum. The colorless gum was dissolved in ether (2 mL) and HCl (0.1 mL, 1N solution in EA) was added. The reaction was stirred at 25° C. for 5 min, filtered and the solid was washed with cold ether to afford 50 mg (77% yield) of the title compound 83 HCl as a white solid. $^1$H NMR (600 MHz, methanol-d4): δ 0.99-1.07 (m, 3H), 1.08-1.16 (m, 3H), 1.26-1.37 (m, 4H), 1.65-1.81 (m, 2H), 1.83-1.93 (m, 1H), 1.95-2.06 (m, 1H), 2.25-2.37 (m, 1H), 2.41-2.62 (m, 2H), 2.65-2.76 (m, 1H), 3.04 (s, 3H), 3.07-3.17 (m, 2H), 4.04 (s, 1H), 5.72-6.09 (m, 2H), 7.08-7.15 (m, 1H), 7.28-7.36 (m, 2H), 7.43-7.50 (m, 1H). LCMS (ESI): m/z calculated for $[C_{22}H_{31}ClN_2O_5+H]^+$ 439.19, found 439.27 $[M+H]^+$.

Example 84

Synthesis of (S)-(((1-(2-chlorophenyl)-2-oxocyclohexyl)(methyl)carbamoyl)oxy)methyl benzoate (84)

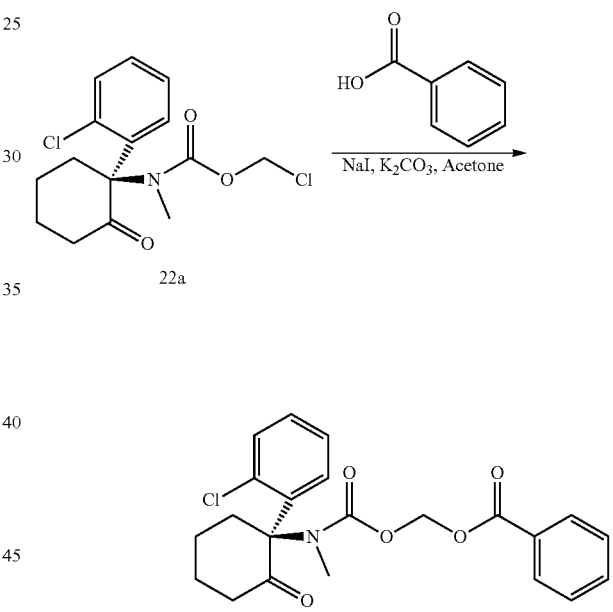

To a solution of 22a (50 mg, 0.15 mmol), NaI (45 mg, 0.30 mmol) and benzoic acid (55 mg, 0.45 mmol) in acetone (2 mL) was added $K_2CO_3$ (105 mg, 0.76 mmol). The reaction was heated to 70° C. for 1 h. The reaction was concentrated and redissolved in DCM (5 mL), washed with $NaHCO_3$(sat) (5 mL) and brine (5 mL). The organic layer was dried over $MgSO_4$, filtered and concentrated to provide an oil, which was purified on silica gel column eluting with Hexane/EA (1/0 to 4/1) to afford 50 mg (80% yield) of the title compound 84 as a white solid. $^1$H NMR (500 MHz, acetone-$d_6$): 1.67-1.87 (m, 2H), 2.38-2.53 (m, 2H), 2.65-2.75 (m, 1H), 2.77-2.79 (m, 2H), 3.06 (s, 3H), 3.17-3.30 (m, 1H), 5.93-6.09 (m, 2H), 7.08 (dd, J=7.8, 1.6 Hz, 1H)), 7.18-7.24 (m, 1H), 7.25-7.30 (m, 1H), 7.43 (dd, J=7.9, 1.4 Hz, 1H), 7.53-7.60 (m, 2H), 7.67-7.74 (m, 1H), 8.05 (d, J=7.5 Hz, 2H). LCMS (ESI): m/z calculated for $[C_{22}H_{22}ClNO_5+H]^+$ 416.12, found 416.08 $[M+H]^+$.

Example 85

Synthesis of (S)-(((1-(2-chlorophenyl)-2-oxocyclohexyl)(methyl)carbamoyl)oxy)methyl piperidine-4-carboxylate (85)

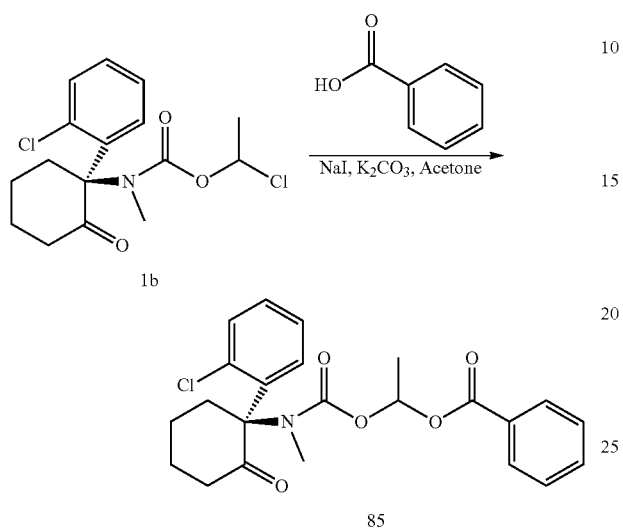

To a solution of 1b (50 mg, 0.15 mmol), NaI (44 mg, 0.29 mmol) and benzoic acid (53 mg, 0.44 mmol) in acetone (2 mL) was added K$_2$CO$_3$ (102 mg, 0.73 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to provide an oil, which was purified on silica gel column eluting with Hexane/EA (1/0 to 4/1) to afford 50 mg (80% yield) of the title compound 85 as a white solid. $^1$H NMR (600 MHz, acetone-d$_6$): 1.50-1.68 (m, 3H), 1.70-1.86 (m, 3H), 2.33-2.54 (m, 2H), 2.75-2.79 (m, 2H), 3.03-3.11 (m, 3H), 3.19-3.34 (m, 1H), 6.95-7.02 (m, 1H), 7.08-7.16 (m, 1H), 7.24-7.33 (m, 2H), 7.40-7.46 (m, 1H), 7.51-7.57 (m, 2H), 7.65-7.70 (m, 1H), 7.97-8.09 (m, 2H). LCMS (ESI): m/z calculated for [C$_{23}$H$_{24}$ClNO$_5$+H]$^+$ 430.13, found 430.02 [M+H]$^+$.

Example 86

Synthesis of (piperidine-4-carboxyloyloxy)methyl (S)-1-(2-chlorophenyl)-2-oxocyclohexylmethylcarbamate (86)

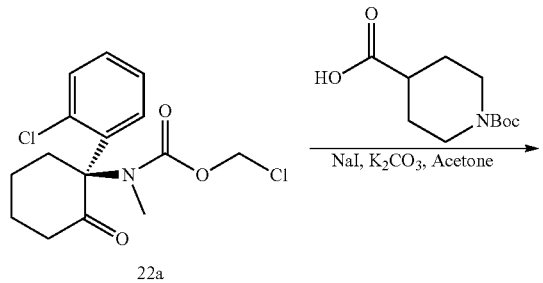

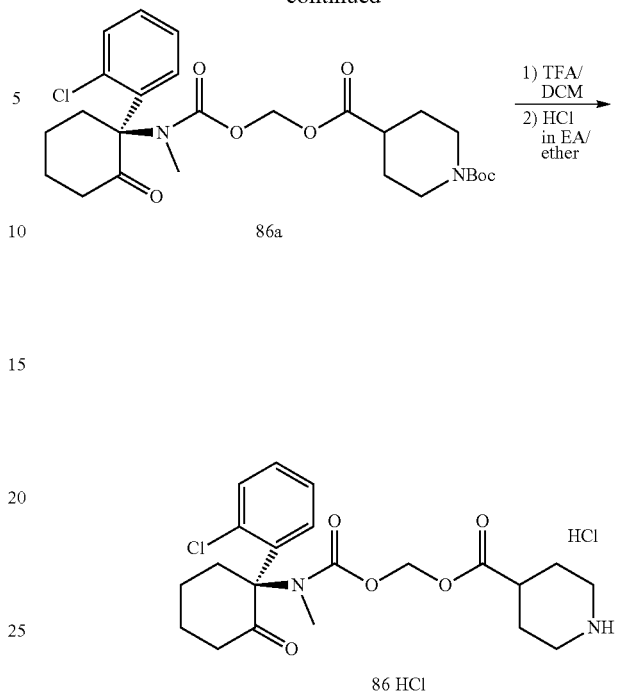

To a solution of 22a (100 mg, 0.30 mmol), NaI (90 mg, 0.60 mmol) and 1-(tert-butoxycarbonyl)piperidine-4-carboxylic acid (208 mg, 0.91 mmol) in acetone (4 mL) was added K$_2$CO$_3$ (210 mg, 1.51 mmol). The reaction was heated to 70° C. for 1 h. The reaction was concentrated and redissolved in DCM (5 mL), washed with NaHCO$_{3(sat)}$ (5 mL) and brine (5 mL). The organic layer was dried over MgSO$_4$, filtered and concentrated to get an oil, which was then purified on silica gel column eluting with Hexane/EA (1/0 to 4/1) to afford 120 mg (76% yield) of 86a as a white foam. $^1$H NMR (600 MHz, acetone-d$_6$): 1.44 (s, 9H), 1.48-1.59 (m, 2H), 1.69-1.92 (m, 6H), 2.40-2.52 (m, 2H), 2.55-2.64 (m, 1H), 2.65-2.73 (m, 1H), 2.83-2.99 (m, 2H), 3.03 (s, 3H), 3.21-3.30 (m, 1H), 3.90-4.00 (m, 2H), 5.66-5.85 (m, 2H), 7.05-7.09 (m, 1H), 7.28-7.33 (m, 2H), 7.43-7.47 (m, 1H). LCMS (ESI): m/z Calcd for [C$_{26}$H$_{35}$ClN$_2$O$_7$+H]$^+$ 523.21, found 522.99 [M+H]$^+$ To a solution of 86a (115 mg, 0.219 mmol) in DCM (8 mL) was added trifluoroacetic acid (0.3 mL, 3.96 mmol). The reaction was stirred at 25° C. for 16 h. The reaction was concentrated to afford 160 mg of 85 TFA as a colorless gum. The title compound (86) TFA was extracted with DCM (15 mL) and pH=3 HCl$_{(aq)}$ (15 mL). The organic layer was dried over MgSO$_4$, filtered and concentrated to afford a colorless gum. The colorless gum was dissolved in ether (2 mL) and HCl (0.1 mL, 1N solution in EA) was added. The reaction was stirred at 25° C. for 5 min, filtered and the solid was washed with cold ether to afford 60 mg (60% yield) of the title compound (86) HCl as a white powder. $^1$H NMR (600 MHz, methanol-d4): δ 1.67-1.83 (m, 2H), 1.83-1.95 (m, 3H), 1.97-2.06 (m, 1H), 2.08-2.18 (m, 2H), 2.39-2.47 (m, 1H), 2.48-2.57 (m, 1H), 2.67-2.74 (m, 1H), 2.75-2.83 (m, 1H), 3.00-3.12 (m, 5H), 3.32-3.39 (m, 2H), 4.49-4.66 (m, 1H), 5.60-5.93 (m, 2H), 7.06-7.11 (m, 1H), 7.28-7.34 (m, 2H), 7.44-7.49 (m, 1H). LCMS (ESI): m/z Calcd for [C$_{21}$H$_{27}$ClN$_2$O$_5$+H]$^+$ 423.16, found 423.29 [M+H]$^+$.

Example 87

Synthesis of ((((S)-1-(2-chlorophenyl)-2-oxocyclohexyl)(methyl)carbamoyl)oxy)methyl acetyl-D-prolinate (87)

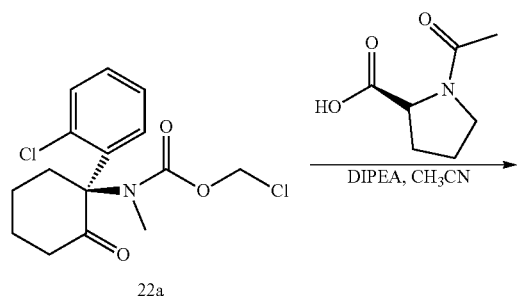

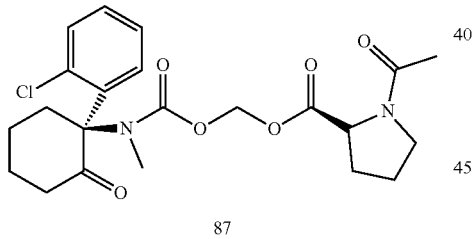

To a solution of 22a (100 mg, 0.3 mmol), and N-acetyl L-proline (71 mg, 0.45 mmol) in acetonitrile (1 mL) was added DIPEA (N,N-diisopropylethylamine, 81 mg, 0.6 mmol). The reaction was stirred at room temperature for 24 h. The reaction was concentrated and redissolved in EtOAc (5 mL), washed with 1N HCl$_{(aq)}$, NaHCO$_{3(sat)}$ (5 mL) and brine (5 mL) sequentially. The organic layer was dried over MgSO4, filtered and concentrated, and purified on silica gel column eluting with Hexane/EA (3/1 to 1/3) to afford 100 mg (73% yield) of the title compound (87) as a white solid. $^1$H NMR (500 MHz, Chloroform-d) δ 7.48-7.05 (m, 4H), 5.85 (s, 2H), 4.46 (dd, J=4.9, 4.0 Hz, 1H), 3.69 (ddd, J=12.0, 5.2, 4.4 Hz, 1H), 3.49 (ddd, J=12.0, 5.2, 4.5 Hz, 1H), 3.02 (s, 3H), 2.59 (dddd, J=7.1, 4.0, 2.9, 1.3 Hz, 2H), 2.30-2.14 (m, 3H), 2.10 (s, 3H), 2.06-1.89 (m, 3H), 1.75-1.53 (m, 4H). LCMS (ESI): m/z Calcd for [C22H27ClN2O6+H]$^+$ 451.16, found 451.02 [M+H]+

Example 88

Synthesis of ((((S)-1-(2-chlorophenyl)-2-oxocyclohexyl)(methyl)carbamoyl)oxy)methyl acetyl-L-phenylalaninate (88)

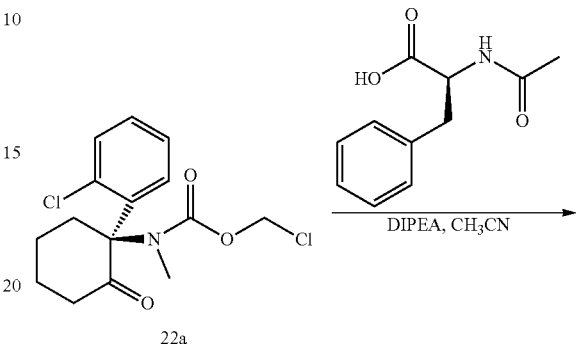

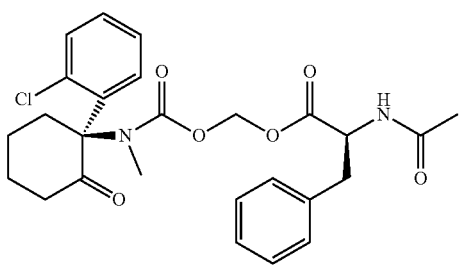

To a solution of 22a (100 mg, 0.3 mmol), and N-acetyl L-phenylalanine (94 mg, 0.45 mmol) in acetonitrile (1 mL) was added DIPEA (N,N-diisopropylethylamine, 81 mg, 0.6 mmol). The reaction was stirred at room temperature for 24 h. The reaction was concentrated and redissolved in EtOAc (5 mL), washed with 1N HCl$_{(aq)}$, NaHCO$_{3(sat)}$ (5 mL) and brine (5 mL) sequentially. The organic layer was dried over MgSO$_4$, filtered and concentrated, and purified on silica gel column eluting with Hexane/EA (3/1 to 1/3) to afford 100 mg (66% yield) of the title compound (88) as a white solid. $^1$H NMR (500 MHz, Chloroform-d) δ 7.41 (dd, J=7.0, 2.4 Hz, 1H), 7.35-7.14 (m, 6H), 7.14-6.93 (m, 3H), 5.93-5.78 (m, 2H), 5.75 (s, 1H), 4.88 (dt, J=7.9, 5.9 Hz, 1H), 3.36-3.21 (m, 1H), 3.14 (dd, J=14.0, 5.7 Hz, 1H), 3.00 (s, 4H), 2.73-2.51 (m, 2H), 2.45 (s, 1H), 1.95 (s, 4H), 1.90-1.75 (m, 1H), 1.75-1.64 (m, 2H), 1.62 (s, 2H). LCMS (ESI): m/z Calcd for [C$_{26}$H$_{29}$ClN$_2$O$_6$+H]$^+$ 501.18, found 501.16 [M+H]$^+$

Example 89

Synthesis of (((((S)-1-(2-chlorophenyl)-2-oxocyclohexyl)(methyl)carbamoyl)oxy)methyl acetyl-L-tyrosinate (89)

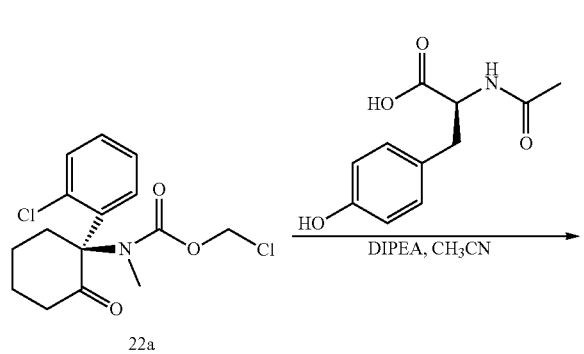

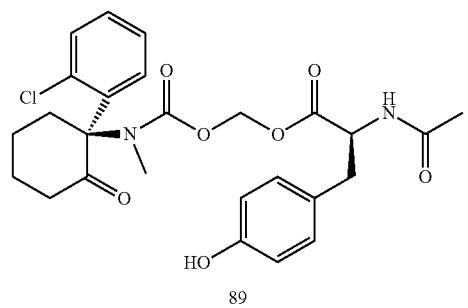

To a solution of 22a (100 mg, 0.3 mmol), and N-acetyl L-tyrosine (100 mg, 0.45 mmol) in acetonitrile (1 mL) was added DIPEA (N,N-diisopropylethylamine, 81 mg, 0.6 mmol). The reaction was stirred at room temperature for 24 h. The reaction was concentrated and redissolved in EtOAc (5 mL), washed with 1N HCl$_{(aq)}$, NaHCO$_{3(sat)}$ (5 mL) and brine (5 mL) sequentially. The organic layer was dried over MgSO$_4$, filtered and concentrated, and purified on silica gel column eluting with Hexane/EA (3/1 to 1/3) to afford 100 mg (64% yield) of the title compound (89) as a white solid. $^1$H NMR (500 MHz, Chloroform-d) δ 7.40 (dd, J=7.1, 2.2 Hz, 1H), 7.30-7.14 (m, 3H), 6.99 (dd, J=7.2, 2.4 Hz, 1H), 6.91 (d, J=8.0 Hz, 2H), 6.68 (d, J=8.3 Hz, 2H), 6.40 (s, 1H), 6.04 (d, J=7.9 Hz, 1H), 5.90-5.54 (m, 2H), 4.84 (q, J=6.5 Hz, 1H), 3.28 (t, J=12.0 Hz, 1H), 3.13-2.85 (m, 4H), 2.76-2.49 (m, 2H), 2.42 (s, 1H), 1.94 (s, 4H), 1.86 (dtd, J=13.7, 9.2, 4.7 Hz, 1H), 1.77-1.54 (m, 4H). LCMS (ESI): m/z Calcd for [C$_{26}$H$_{29}$ClN$_2$O$_7$+H]$^+$ 517.17, found 517.16 [M+H]$^+$

Example 90

Synthesis of 1-(((((S)-1-(2-chlorophenyl)-2-oxocyclohexyl)(methyl)carbamoyl)oxy)ethyl dimethyl-L-valinate (90)

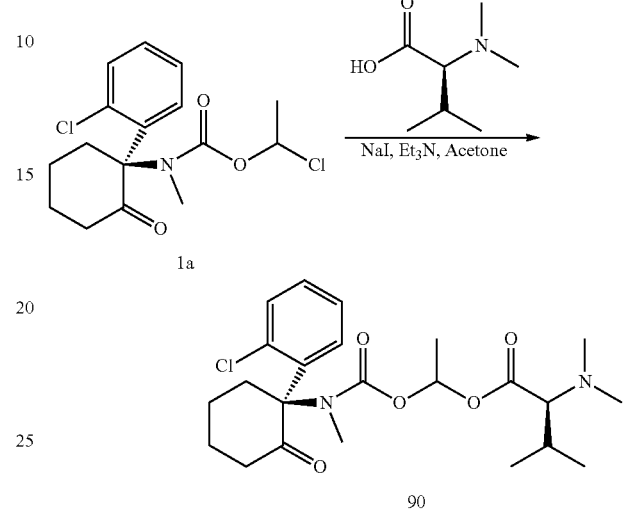

To a solution of 1a (500 mg, 1.45 mmol), NaI (436 mg, 2.91 mmol) and (S)-2-(dimethylamino)-3-methylbutanoic acid (633 mg, 4.36 mmol) in acetone (25 mL) was added TEA (1.02 mL, 7.29 mmol). The reaction was heated to 70° C. for 5 h. The reaction was concentrated and redissolved in DCM (5 mL), washed with NaHCO$_{3(sat)}$ (5 mL) and brine (5 mL). The organic layer was dried over MgSO$_4$, filtered and concentrated to get an oil, which was purified on silica gel column eluting with Hexane/EA (1/0 to 7/3) to afford 440 mg (67% yield) of the title compound (90) as a white foam. $^1$H NMR (600 MHz, acetone-d$_6$): 0.81-0.98 (m, 6H), 1.38-1.63 (m, 3H), 1.70-1.88 (m, 3H), 1.95-2.02 (m, 2H), 2.27 (s, 6H), 2.35-2.54 (m, 2H), 2.62-2.76 (m, 2H), 3.05 (s, 3H), 3.17-3.34 (m, 1H), 6.78-6.84 (m, 1H), 7.04-7.12 (m, 1H)), 7.27-7.33 (m, 2H), 7.41-7.47 (m, 1H). LCMS (ESI): m/z Calcd for [C$_{23}$H$_{33}$ClN$_2$O$_5$]$^+$ 452.21, found 452.59 [M]$^+$.

Example 91

Chemical Stability

Stock solutions of the test compounds were prepared in acetonitrile or H$_2$O in a final concentration of 1 mg/mL. One-hundred (100) μL stock solution was added to 900 μL pH buffer or USP buffer (pH 3.0, pH 6.8, or pH 7.4). The reaction was incubated at 37° C. At the desired timepoint (0, 1, and 4 h), a 2 μL sample was obtained and analyzed by UPLC (Waters CORTECS® UPLC, C18, 2.1×50 mm, 1.6 μm). The temperature of the autosampler was 37° C. and the temperature of the column was 30° C. The elution solvents were H$_2$O with 0.1% TFA as buffer A and 100% acetonitrile as buffer B. The flow rate was 0.3 mL/min. The UV spectrum was analyzed by 220 nm.

Example 92

DMPK Procedures

Preparation of Test Article and Assay Stock Solutions: Stock solutions of test compounds were prepared in acetonitrile at 3 mM. Primary stock solutions were then diluted 10-fold in acetonitrile to yield working stock solutions of 0.3 mM. The stock solutions were stored at −20° C.

S9 Stability Assay: Potassium phosphate buffer (100 mM, pH 7.4) containing 3 mM MgCl$_2$ was pre-incubated in triplicate with a test compound (3 M, final acetonitrile concentration 0.1%) in a 37° C. incubator for 10 min. The reaction was initiated by adding pre-warmed rat S9 (1.0 mg/mL) in the presence of 2 mM NADPH. The final incubation mixture volume was 200 μL. All reactions were terminated using five volumes of extraction solvent at the pre-defined time points (0 to 60 min). Aliquots of terminated incubation mixtures were centrifuged at 20,000×g for 5 min. The supernatants were analyzed with LC-MS/MS for the amount of the test article remaining and ketamine formation.

Whole Blood Stability Assay: Test compounds were incubated in 37° C. pre-warmed rat whole blood at 3 μM (final acetonitrile concentration 1%) for up to 60 min at 37° C. One-hundred 100 μL aliquots of spiked sample solutions were taken at pre-defined time points (0 to 60 min) post incubation, and were immediately extracted by adding 5 volumes of extraction solvent and then centrifuged at 20,000×g for 5 min. The supernatant fractions were analyzed with LC-MS/MS for the amount of the test compound remaining and ketamine.

Whole blood stability of certain ketamine derivatives are shown in Table 1.

TABLE 1

Whole blood stability.

| Compound | Mouse Ket (%) | Rat Ket (%) | Dog Ket (%) | Monkey Ket (%) | Human Ket (%) |
|---|---|---|---|---|---|
| S-ketamine | 100 | 100 | 100 | 100 | 100 |
| 1 | —[1] | 45.71 | — | — | — |
| 3 | 67.47 | 74.92 | 82.14 | 75.11 | 74.11 |
| 6 | 122.58 | 84.28 | 2.29 | 12.88 | 2.56 |
| 7 | — | 73.83 | — | — | — |
| 9 | — | 65.17 | — | — | — |
| 12 | 78.13 | — | — | — | — |
| 14 | 119.76 | — | 33.52 | 60.11 | — |
| 16 | 148.78 | — | — | 34.25 | 28.38 |
| 18 | 150.78 | — | — | 55.26 | — |
| 19 | 136.03 | — | — | 74.36 | — |
| 20 | 98.97 | — | — | — | — |
| 21 | 125.27 | — | — | — | — |
| 22 | 107.83 | 82.55 | 7.86 | 62.86 | 15.47 |
| 24 | 117.55 | — | — | — | — |
| 26 | 101.54 | — | — | — | — |
| 27 | 187.52 | 94.75 | 99.25 | 116.7 | 61.69 |
| 28 | 110.63 | 101.22 | — | — | — |
| 29 | 113.11 | 85.49 | 86.32 | 77.88 | 90.77 |
| 32 | 117.02 | — | 41.62 | — | 65.5 |
| 35 | 143.7 | — | — | — | — |
| 36 | 134.67 | — | — | — | — |
| 37 | 141.89 | — | — | — | — |
| 39 HCL | 20.18 | 6.48 | 5.38 | — | 7.46 |
| 39 (R) | — | — | — | — | 13.59 |
| 54 | 74.88 | 87.68 | 9.87 | — | 8.83 |
| 55 | 106.77 | 96.75 | 10.79 | — | 83.63 |
| 60 | — | — | — | — | 40.98 |

[1] Not measured.

Vehicles Used in PK Studies: The vehicles listed in Table 2 were used in the pharmacokinetic studies.

TABLE 2

PK vehicle compositions.

| Vehicle | Components |
|---|---|
| F1 | 20% HPβCD in DI water |
| F2 | 0.5% methylcellulose and 0.1% (v/v) Tween 80 in DI water |
| F3 | 2% PEG 400 and 20% HPβCD in saline |
| F4 | 2% DMA, 10% Glycerol, and 10% HPβCD in normal saline |

DMA: Dimethylacetamide; DI water: Deionized water; HPβCD: (2-hydroxypropyl)-β-cyclodextrin; PEG: Polyethylene glycol.

Dose formulation analysis: A reversed phase liquid chromatography (RP-UPLC) method was developed for monitoring prodrugs of ketamine. Chromatographic separation was performed on a XDB-C18 column (1.8 μm, 4.6×50 mm, Agilent), using a gradient elution procedure. The solvent system consisted of solvent A (water) and solvent B (acetonitrile). Solvent B was delivered initially at 25%, held for 0.5 min, and increased to 60% via a 22 min gradient, and increased to 100% via a 0.5 min gradient, and then held for 3 min. The column was re-equilibrated for 3 min using the initial mobile phase composition (25% solvent B). The entire gradient-equilibration cycle required 30 min for completion. Linear gradient elution mode with a flow rate of 0.6 m/min was used, and the injection volume was 10 μL. The column temperature was maintained at 30° C. and the eluted compounds were monitored at a wavelength of 215 nm. UPLC data were acquired and the chromatograms were integrated using Empower 3 Software.

In vivo Mouse/Rat PK Studies: Pharmacokinetic profiles of the test compounds were evaluated in mice and rats following (S-ketamine) or oral (S-ketamine or prodrugs) administration. The oral dose level was 5 mol/kg to 160 mol/kg administered at a volume of 10 mL/kg. Blood samples were collected from the facial veins using heparinated tubes at pre-dose and 0.05, 0.17, 0.5, 1, 2, 3, 4, 6, and 8 hours post-dose following intravenous administration, and withdrawn at pre-dose and 0.17, 0.5, 1, 2, 3, 4, 5, 6, and 8 hours post-dose following oral administration. In each mouse PK study, mice were sub-grouped for a sparse sampling strategy. Each mouse provided two blood samples at different collection times. Blood samples were collected from alternating groups of three mice per time point. To prevent compound degradation, drawn blood samples were immediately mixed in a ratio of 1:3 (v/v) with acetonitrile (containing 0.1% formic acid). The de-proteinized samples were temporarily held in ice following by storing at −70° C. before bioanalysis. The concentrations of analytes in the blood were determined by LC-MS/MS.

In vivo Dog PK Studies: Three male Beagle dogs were housed individually. Dogs in the oral administration groups were fasted overnight before treatment but with free access to water. Dogs in the IV groups had free access to food and water. For S-ketamine HCl salt, a single dose of 3.75 mol/kg was administered to each dog via intravenous (IV) administration. The vehicle used for S-ketamine HCl salt was saline. For other test compounds, a single dose of each test compound was administered to each dog via oral gavage (n=3/group). The vehicles used for dosing the test compounds were dependent on the properties of the test compound. Blood samples were collected at specified time-points (pre-dose, 10 min, 30 min, 1 h, 2 h, 3 h, 4 h, 5 h, 6 h, 8 h, post-dose) following administration to individual dogs within IV and PO group. To prevent compound degradation, drawn blood samples were immediately mixed in a ratio of 1:3 (v/v) with acetonitrile (containing 0.1% formic acid). The de-proteinized samples were temporarily held in ice following by storing at −70° C. before bioanalysis. The concentrations of analytes in the blood were determined by LC-MS/MS. Various pharmacokinetic parameters were calculated using Phoenix™ WinNonlin® software. To quantify the bioconversion efficiency of the test compounds in the circulation system, the bioavailability of S-ketamine after PO administration was calculated.

In vivo Monkey PK studies: Three cynomolgus monkeys (two males, one female) (*Macaca fascicularis*), from the colony at the Laboratory Animal Center (LAC) of the National Defense Medical Center (NDMC), were used in the study. The mean age of the monkeys was 6 years with a mean weight of 6.6 kg (6 kg to 7 kg). Pharmacokinetics of S-ketamine and compound 3 were evaluated following an intravenous administration of S-ketamine and oral administrations of S-ketamine and compound 3. Each treatment was conducted at least 7 days washout between treatments. On the day of the in vivo experiments, monkeys were sedated by intramuscular injection of Alfaxan® (5 mg/kg) and Dexmedetomidine® (10 mcg/kg). For intravenous administration, the S-ketamine solution was administered as a bolus injection slowly via a cephalic vein at a dose of 3.2 mol/kg. The dose volume administered was 0.5 mL/kg. For oral administration, S-ketamine or compound 3 was administered at 6.4 mol/kg via oral gavage. The dose volume administered was 1 mL/kg. Monkeys in the intravenous treatment group had free access to a laboratory diet, and monkeys in the oral treatment group were fasted overnight prior to treatment and 2 to 3 hours after administering the test compound. Drinking water was supplied ad libitum during the study period. Serial blood samples (0.35 mL/each) were collected from monkeys through the saphenous vein. Collected blood samples were placed into tubes containing heparin as the anticoagulant. Blood samples of IV group were collected at pre-dose, 0.083, 0.5, 1, 1.5, 2, 3, 4, 6, 8, and 24 hr post-dose. For PO group, blood samples were collected at pre-dose, 0.5, 1, 1.5, 2, 3, 4, 5, 6, 8, and 24 hr post-dose. To prevent compound degradation, after being drawn from the monkeys 100 μL blood samples were immediately mixed with 300 μL of acetonitrile (containing 0.1% formic acid) in a ratio of 1:3 (v/v). The de-proteinized samples were temporarily held in ice following by storing at −70° C. before bioanalysis. The concentrations of the analytes in blood were determined by LC-MS/MS.

Bio-Analysis: Samples were monitored for parent compound disappearance and ketamine formation in multi-reaction monitoring (MRM) mode by LC-MS/MS system. The mobile phase was performed at a constant flow rate of 0.8 mL/min using a binary solvent system: Solvent A, de-ionized water containing 0.1% formic acid, and Solvent B, methanol containing 0.1% formic acid. MRM data were acquired, and the chromatograms were integrated using Quant Wizard of the version 1.5.2 software (Analyst Software from ABI). A weighted (1/x or $1/x^2$) linear regression was used to generate the calibration curve from standards and to calculate the sample concentrations.

Pharmacokinetic Data Analysis: The pharmacokinetic parameters were estimated for each subject using the Phoenix™ WinNonlin program, version 6.3 (Phoenix WinNonlin© 2012, Pharsight Corporation, Mountain View, Calif.). Non-compartmental analysis was performed to generate parameter estimates. The terminal elimination rate constant (λ) was obtained, where possible, by linear regression of the terminal elimination phase of a log-linear plot of the blood concentration-time data. The criteria for X acceptance were regression of at least three time points from the terminal elimination phase and $r^2 \leq 0.85$. Half-life was defined as not determined (ND) if the criteria could not be met. Nominal time was used for $t_{1/2}$ and AUC calculations. The apparent blood terminal elimination half-life ($t_{1/2}$) was calculated according to the following formula: $t_{1/2} = \ln(2)/\lambda$. The observed maximum blood concentration ($C_{max}$) and the time to reach the maximum blood concentration ($T_{max}$) were obtained by visual inspection of the experimental data. The area under the blood concentration-time curve of ketamine from time 0 to the last measurable concentration ($AUC_{(0-Last)}$) was determined by the linear trapezoidal method. The area under the blood concentration-time curve from time 0 to infinity ($AUC_{(0\to\infty)}$) was determined by $AUC_{(0-Last)} + C_{Last}/\lambda$, in which $C_{Last}$ was the concentration corresponding to the time point of last measurable concentration ($T_{Last}$).

Mean residence time (MRT) was obtained from the ratio of ($AUMC_{(0\to\infty)}/AUC_{(0\to\infty)}$), where $AUMC_{(0\to\infty)}$ was the area under the first moment curve, which was equal to:

$$AUMC_{(0-Last)} + \frac{T_{Last} \times C_{Last}}{\lambda} + \frac{C_{Last}}{\lambda^2}$$

The apparent blood total clearance (CL) and the volume of distribution at steady state ($V_{ss}$) were calculated according to the following formula: $CL = Dose_{IV}/AUC_{(0\to\infty)}$ and $V_{ss} = MRT \times CL$.

Pharmacokinetic parameters for ketamine and ketamine derivatives in dogs is shown in Table 3.

TABLE 3

Summary of pharmacokinetic parameters of ketamine and prodrugs in dogs.

| Compound | Route | $C_{max}$[2] (nM) | $AUC_{(0-last)}$[2] (nM × hr) | F[2] (%) |
|---|---|---|---|---|
| S-ketamine @ 3.75 μmol/kg | IV | 669 | 244 | —[3] |
| S-ketamine @ 15 μmol/kg | PO | 9 | 17 | 1.8 |
| 3[1] | PO | 54 | 55 | 5.6 |
| 6 | PO | 27 | 42 | 4.3 |
| 14 | PO | 3 | 5 | 0.5 |
| 22 | PO | 12 | 23 | 2.4 |
| 29 | PO | 12 | 9 | 0.9 |
| 39 HCl | PO | 33 | 46 | 4.7 |
| 39 (R) | PO | 8 | 9 | 0.9 |
| 60 | PO | 23 | 37 | 3.8 |

[1] Ketamine derivatives were dosed at 15 μmol/kg.
[2] Measured and calculated based on the relative bioavailability with respect to S-ketamine.
[3] Not measured.

Pharmacokinetic parameters for ketamine and ketamine derivatives in monkeys is shown in Table 4.

TABLE 4

Summary of pharmacokinetic parameters of ketamine and prodrugs in monkeys.

| Compound | Route | $C_{max}$[1] (nM) | AUC(0-∞)[1] (nM × hr) | F[1] (%) |
|---|---|---|---|---|
| S-Ketamine @ 5 μmol/kg | IV | 1199 | 2325 | —[2] |
| S-Ketamine @ 10 μmol/kg | PO | 13 | 34 | 0.7 |
| Compound 3 @ 10 μmol/kg | PO | 23 | 115 | 2.5 |

[1] Measured and calculated based on S-ketamine; and the relative bioavailability.
[2] Not measured.

Table 5 provides a summary of the oral bioavailability of ketamine and certain ketamine derivatives in mice, rats, dogs, and monkeys.

TABLE 5

Summary of pharmacokinetic parameters of ketamine and ketamine derivatives in different species.

| Compound | Mouse F[1] (%) | Rat F[1] (%) | Dog F[1] (%) | Monkey F[1] (%) |
|---|---|---|---|---|
| S-ketamine | 5.6 | 4.9 | 1.8 | 0.7 |
| 3 | 7.1 | 4.2 | 5.6 | 2.5 |
| 6 | 8.3 | 8.6 | 4.3 | —[2] |
| 7 | 5.9 | 6.5 | — | — |
| 8 | 1.2 | — | — | — |
| 14 | 7.0 | — | 0.5 | — |
| 19 | 10.2 | — | — | — |
| 21 | 7.1 | — | — | — |
| 22 | 11.4 | 6.1 | 2.4 | — |
| 29 | 16.8 | 6.4 | 0.9 | — |
| 32 | — | 5.0 | — | — |
| 34 | 11.8 | — | — | — |
| 35 | 7.5 | — | — | — |
| 36 | — | 8.3 | — | — |
| 39 | 10.7 | 6.6 | 4.7 | — |
| 41 | 18.0 | — | — | — |
| 45 | 4.4 | 4.2 | — | — |
| 49 | 8.7 | — | — | — |
| 50 | 6.0 | — | — | — |
| 51 | 6.5 | — | — | — |
| 53 | 12.8 | — | — | — |
| 57 | — | 6.6 | — | — |
| 60 | 6.2 | 7.6 | 3.8 | — |

[1]Measured and calculated based on the relative bioavailability with respect to S-ketamine.
[2] Not measured.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A method of treating a psychiatric disease or disorder in a patient comprising administering to a patient in need of such treatment, a therapeutically effective amount of the compound of Formula (1):

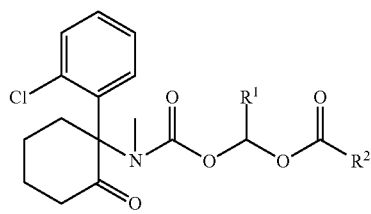

(1)

or a pharmaceutically acceptable salt thereof, wherein,
$R^1$ is selected from hydrogen and $C_{1-3}$ alkyl; and
$R^2$ is selected from a moiety of Formula (2) and a moiety of Formula (4):

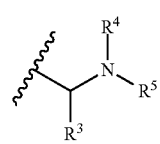

(2)

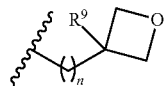

(4)

wherein,
$R^3$ is selected from hydrogen and $C_{1-6}$ alkyl;
$R^4$ is selected from hydrogen and $C_{1-3}$ alkyl;
$R^5$ is selected from $C_{1-3}$ alkyl and —C(=O)—$R^{10}$, wherein $R^{10}$ is selected from $C_{1-6}$ alkyl and —$CF_3$;
n is 1; and
$R^9$ is $C_{1-3}$ alkyl,
wherein the psychiatric disease or disorder is selected from an alcohol use disorder, an anxiety disorder, an obsessive-compulsive disorder, an opioid use disorder, and a posttraumatic stress disorder.

2. The method of claim 1, wherein administering comprises orally administering.

3. The method of claim 1, wherein the compound is the (R)-isomer having the structure of Formula (1a):

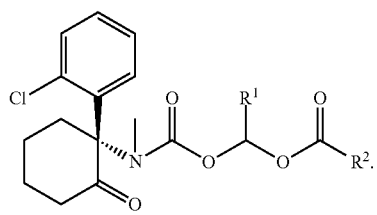

(1a)

4. The method of claim 1, wherein the compound is the (S)-isomer having the structure of Formula (1b):

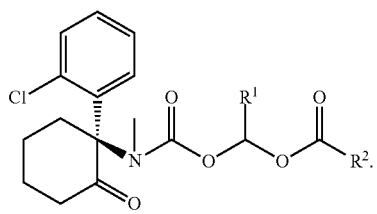

(1b)

5. The method of claim 1, wherein the compound is selected from:

1-((((S)-1-(2-chlorophenyl)-2-oxocyclohexyl)(methyl)carbamoyl)oxy)ethyl acetylglycinate (3):

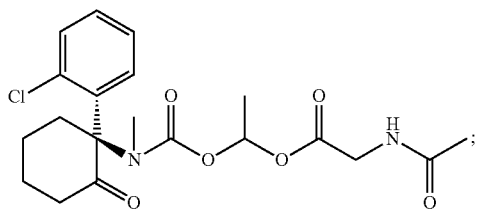

1-((((S)-1-(2-chlorophenyl)-2-oxocyclohexyl)(methyl) carbamoyl)oxy)ethyl 2-(3-methyloxetan-3-yl)acetate (6):

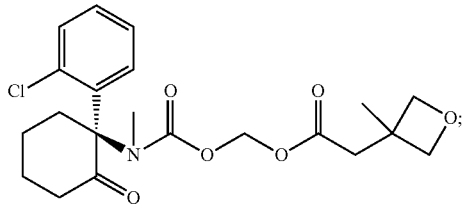 [SMILES: CN(C(=O)OCOC(=O)CC1(C)COC1)[C@]1(c2ccccc2Cl)CCCCC1=O]

1-((((S)-1-(2-chlorophenyl)-2-oxocyclohexyl)(methyl) carbamoyl)oxy)ethyl acetyl-L-alaninate (7):

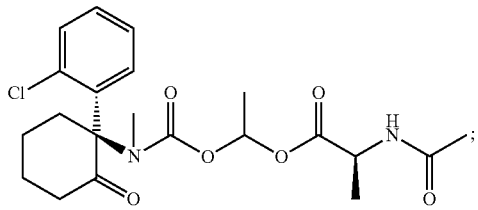

1-((((S)-1-(2-chlorophenyl)-2-oxocyclohexyl)(methyl) carbamoyl)oxy)ethyl isobutyrylglycinate (19):

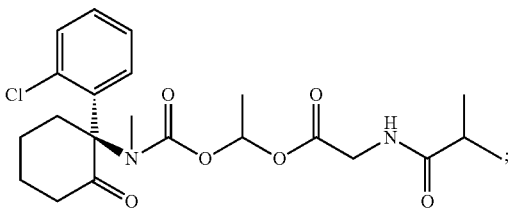

(S)-(((1-(2-chlorophenyl)-2-oxocyclohexyl)(methyl)carbamoyl)oxy)methyl 2-(3-methyloxetan-3-yl)acetate (22):

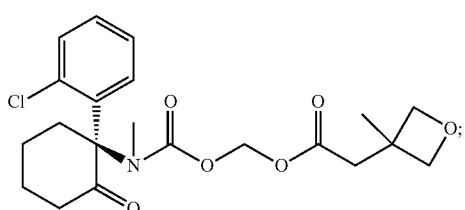

((((S)-1-(2-chlorophenyl)-2-oxocyclohexyl)(methyl)carbamoyl)oxy)methyl acetyl-L-valinate (32):

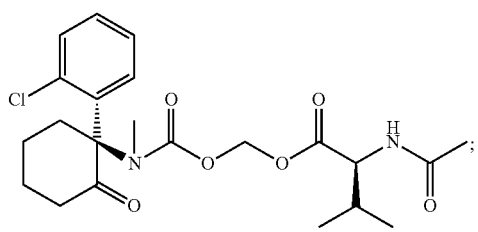

(S)-(((1-(2-chlorophenyl)-2-oxocyclohexyl)(methyl)carbamoyl)oxy)methyl isobutyrylglycinate (34):

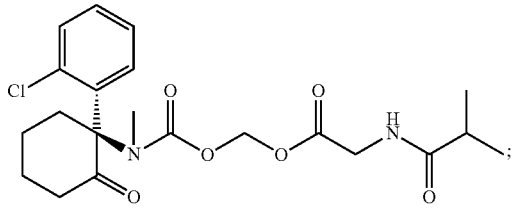

((((S)-1-(2-chlorophenyl)-2-oxocyclohexyl)(methyl)carbamoyl)oxy)methyl isobutyryl-L-alaninate (35):

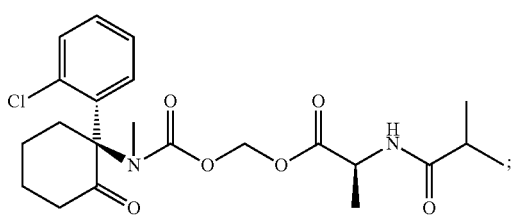

((((S)-1-(2-chlorophenyl)-2-oxocyclohexyl)(methyl)carbamoyl)oxy)methyl isobutyryl-L-valinate (36):

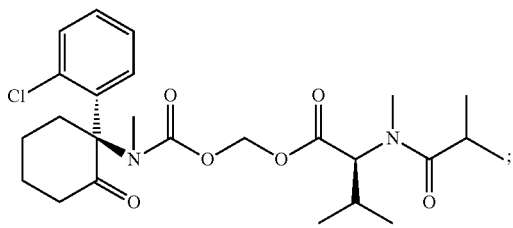

1-((((S)-1-(2-chlorophenyl)-2-oxocyclohexyl)(methyl) carbamoyl)oxy)ethyl N-acetyl-N-methylglycinate (41):

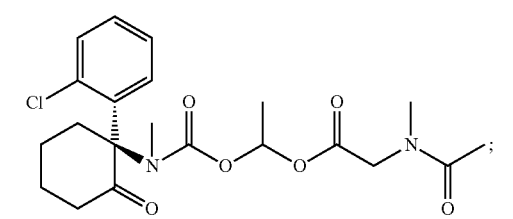

1-((((S)-1-(2-chlorophenyl)-2-oxocyclohexyl)(methyl) carbamoyl)oxy)propyl (2,2,2-trifluoroacetyl)glycinate (49):

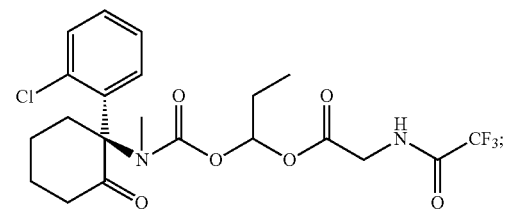

1-((((S)-1-(2-chlorophenyl)-2-oxocyclohexyl)(methyl)carbamoyl)oxy)methyl (2,2,2-trifluoroacetyl)-L-alaninate (50):

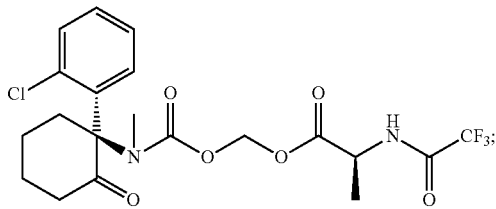

1-((((S)-1-(2-chlorophenyl)-2-oxocyclohexyl)(methyl)carbamoyl)oxy)-2-methylpropyl (2,2,2-trifluoroacetyl)glycinate (51):

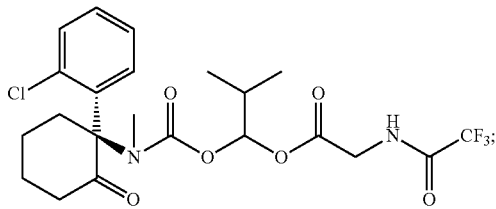

1-((((S)-1-(2-chlorophenyl)-2-oxocyclohexyl)(methyl)carbamoyl)oxy)ethyl (2,2,2-trifluoroacetyl)-L-alaninate (53):

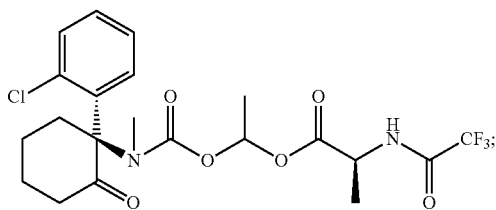

1-((((S)-1-(2-chlorophenyl)-2-oxocyclohexyl)(methyl)carbamoyl)oxy)ethyl acetyl-L-soleucinate (57):

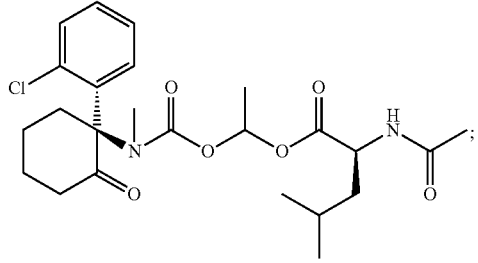

((((S)-1-(2-chlorophenyl)-2-oxocyclohexyl)(methyl)carbamoyl)oxy)methyl acetyl-L-alloisoleucinate (60): and

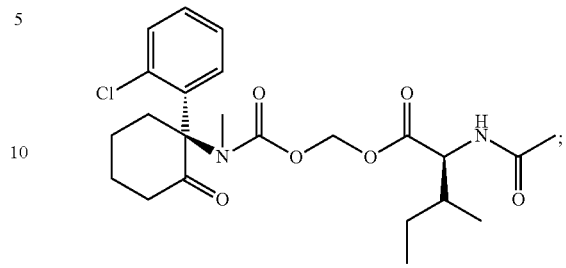

or a pharmaceutically acceptable salt of any of the foregoing.

6. The method of claim 1, wherein,
$R^1$ is selected from hydrogen and methyl;
$R^2$ is a moiety of Formula (2);
$R^3$ is selected from hydrogen and $C_{1-4}$ alkyl;
$R^4$ is selected from hydrogen and methyl; and
$R^5$ is —C(=O)—$R^{10}$, wherein $R^{10}$ is selected from methyl and —$CF_3$.

7. The method of claim 1, wherein,
$R^1$ is selected from hydrogen and methyl;
$R^2$ is a moiety of Formula (4); and
$R^9$ is methyl.

8. The method of claim 1, wherein, following administration, the compound provides a therapeutically effective amount of (S)-ketamine in the patient's blood for treating the psychiatric disease or disorder.

9. The method of claim 1, wherein the compound is (S)-(((1-(2-chlorophenyl)-2-oxocyclohexyl)(methyl)carbamoyl)oxy)methyl 2-(3-methyloxetan-3-yl)acetate (22) or a pharmaceutically acceptable salt thereof:

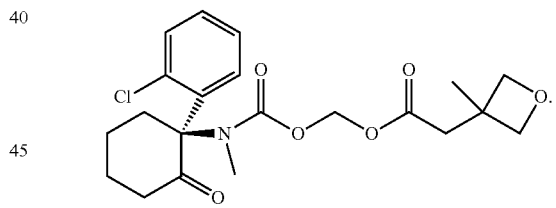

10. The method of claim 1, wherein the compound is 2-(3-methyloxetan-3-yl)acetoyloxy)methyl (R)-1-(2-chlorophenyl)-2-oxocyclohexylmethylcarbamate (66) or a pharmaceutically acceptable salt thereof:

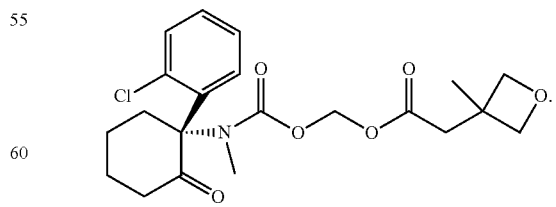

11. The method of claim 1, wherein the compound is ((((S)-1-(2-chlorophenyl)-2-oxocyclohexyl)(methyl)carbamoyl)oxy)methyl dimethyl-L-valinate (39) or a pharmaceutically acceptable salt thereof:

12. The method of claim 1, wherein the compound has the structure of Formula (1a);

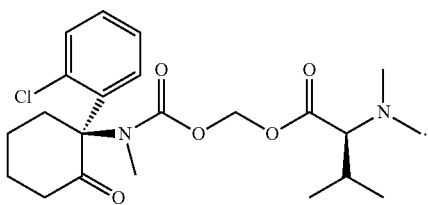 [SMILES: CC(C)[C@@H](C(=O)OCOC(=O)N(C)[C@]1(c2ccccc2Cl)CCCCC1=O)N(C)C]

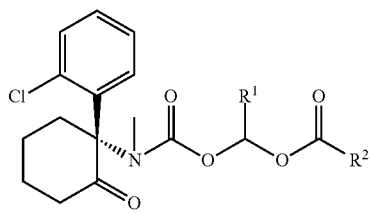

(1a)

or a pharmaceutically acceptable salt thereof, wherein,
$R^1$ is hydrogen;
$R^2$ is a moiety of Formula (2);
$R^3$ is isopropyl and the carbon atom to which $R^3$ is bonded is in the (S) configuration; and
each of $R^4$ and $R^5$ is methyl.

13. The method of claim 1, wherein administering comprises administering a pharmaceutical composition comprising the compound of Formula (1) or a pharmaceutically acceptable salt thereof.

14. The method of claim 1, wherein the psychiatric disease or disorder is an alcohol use disorder.

15. The method of claim 1, wherein the psychiatric disease or disorder is an obsessive compulsive disorder.

16. The method of claim 1, wherein the psychiatric disease or disorder is an opioid use disorder.

17. The method of claim 1, wherein the psychiatric disease or disorder is an anxiety disorder.

18. The method of claim 1, wherein the psychiatric disease or disorder is a post-traumatic stress disorder.

* * * * *